（12）United States Patent
Kitano et al.

(10) Patent No.: US 9,133,169 B2
(45) Date of Patent: Sep. 15, 2015

(54) HETEROCYCLIC COMPOUND, LIGHT-EMITTING ELEMENT, LIGHT-EMITTING DEVICE, ELECTRONIC DEVICE, AND LIGHTING DEVICE

(75) Inventors: Yasushi Kitano, Kanagawa (JP); Harue Osaka, Kanagawa (JP); Satoko Shitagaki, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 477 days.

(21) Appl. No.: 13/596,757

(22) Filed: Aug. 28, 2012

(65) Prior Publication Data

US 2013/0048971 A1 Feb. 28, 2013

(30) Foreign Application Priority Data

Aug. 31, 2011 (JP) .................................. 2011-189089

(51) Int. Cl.
*H01L 51/54* (2006.01)
*C07D 409/14* (2006.01)
(Continued)

(52) U.S. Cl.
CPC ............ *C07D 403/14* (2013.01); *C07D 405/14* (2013.01); *C07D 409/14* (2013.01); *H01L 51/0067* (2013.01); *H01L 51/5012* (2013.01); *H01L 2251/5384* (2013.01)

(58) Field of Classification Search
CPC .. C07D 403/14; C07D 405/14; C07D 409/14; H01L 2251/5384; H01L 51/0067; H01L 51/5012; H01L 51/50; C09K 11/06; H05B 33/14
See application file for complete search history.

(56) References Cited

U.S. PATENT DOCUMENTS 5,281,489 A * 1/1994 Mori et al. ..................... 428/690
6,723,445 B2 4/2004 Li et al.
(Continued)

FOREIGN PATENT DOCUMENTS

CN 101203968 A 6/2008
(Continued)

OTHER PUBLICATIONS

Machine translation for KR 10-2011-042004 (publication date Apr. 2011).*
(Continued)

*Primary Examiner* — Dawn Garrett
(74) *Attorney, Agent, or Firm* — Fish & Richardson P.C.

(57) ABSTRACT

Provided is a novel heterocyclic compound which can be used in a light-emitting layer of a light-emitting element as a host material in which a light-emitting substance is dispersed. A heterocyclic compound represented by a general formula (G1) is provided. Any one of $R^1$ to $R^{10}$ represents a substituent represented by a general formula (G1-1), another one of $R^1$ to $R^{10}$ represents a substituent represented by a general formula (G1-2), and the others separately represent hydrogen, an alkyl group having 1 to 6 carbon atoms, a substituted or unsubstituted phenyl group, or a substituted or unsubstituted biphenyl group. Further, $\alpha^1$ and $\alpha^2$ separately represent a substituted or unsubstituted phenylene group or a substituted or unsubstituted biphenyldiyl group, and $A^1$ and $A^2$ separately represent a substituted or unsubstituted carbazolyl group, a substituted or unsubstituted dibenzothiophenyl group, or a substituted or unsubstituted dibenzofuranyl group.

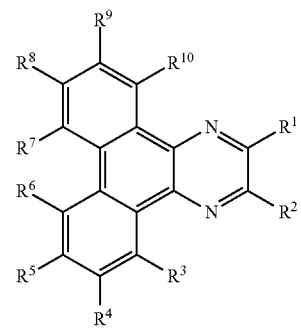

19 Claims, 28 Drawing Sheets

(51) Int. Cl.
*C07D 403/14* (2006.01)
*C07D 405/14* (2006.01)
*H01L 51/00* (2006.01)
*H01L 51/50* (2006.01)

(56) References Cited

U.S. PATENT DOCUMENTS

| | | |
|---|---|---|
| 7,355,340 B2 | 4/2008 | Shitagaki et al. |
| 7,601,435 B2 | 10/2009 | Shitagaki et al. |
| 7,927,720 B2 | 4/2011 | Nomura et al. |
| 7,931,974 B2 | 4/2011 | Egawa et al. |
| 8,084,146 B2 | 12/2011 | Murase et al. |
| 8,119,259 B2 | 2/2012 | Kadoma et al. |
| 8,138,303 B2 | 3/2012 | Chebotareva et al. |
| 8,178,216 B2 | 5/2012 | Nomura et al. |
| 8,231,984 B2 | 7/2012 | Shitagaki et al. |
| 8,252,433 B2 | 8/2012 | Egawa et al. |
| 8,314,101 B2 | 11/2012 | Kadoma et al. |
| 2009/0026922 A1 | 1/2009 | Iwaki et al. |
| 2009/0072718 A1 | 3/2009 | Nomura et al. |
| 2009/0140641 A1 | 6/2009 | Nomura et al. |
| 2009/0140642 A1 | 6/2009 | Kadoma et al. |
| 2009/0153041 A1 | 6/2009 | Kawakami et al. |
| 2009/0184633 A1 | 7/2009 | Kadoma et al. |
| 2009/0203704 A1 | 8/2009 | Kadoma et al. |
| 2010/0039024 A1 | 2/2010 | Wendeborn et al. |
| 2010/0090588 A1 | 4/2010 | Yokoyama et al. |
| 2010/0249349 A1 | 9/2010 | Chebotareva et al. |
| 2010/0289406 A1 | 11/2010 | Ma et al. |
| 2011/0089407 A1 | 4/2011 | Schmidhalter et al. |
| 2011/0210316 A1 | 9/2011 | Kadoma et al. |
| 2012/0138907 A1 | 6/2012 | Murase et al. |
| 2012/0193613 A1 | 8/2012 | Kadoma et al. |
| 2012/0197020 A1 | 8/2012 | Osaka et al. |
| 2012/0286257 A1 | 11/2012 | Shitagaki et al. |
| 2012/0313506 A1 | 12/2012 | Egawa et al. |
| 2013/0060033 A1 | 3/2013 | Seo et al. |
| 2013/0075704 A1 | 3/2013 | Takasu et al. |
| 2014/0034925 A1 | 2/2014 | Osaka et al. |

FOREIGN PATENT DOCUMENTS

| | | |
|---|---|---|
| CN | 101853923 A | 10/2010 |
| CN | 101867019 A | 10/2010 |
| CN | 101970448 A | 2/2011 |
| EP | 1616864 A1 | 1/2006 |
| EP | 1748045 A1 | 1/2007 |
| EP | 1905768 A1 | 4/2008 |
| EP | 1962354 A1 | 8/2008 |
| EP | 2055704 A1 | 5/2009 |
| EP | 2065378 A1 | 6/2009 |
| EP | 2236506 A1 | 10/2010 |
| EP | 2 363 398 A1 | 9/2011 |
| EP | 2450356 A1 | 5/2012 |
| JP | 2006-324650 A | 11/2006 |
| JP | 2007-189001 A | 7/2007 |
| JP | 2007-189001 A | 7/2007 |
| JP | 2008-106051 A | 5/2008 |
| JP | 2008-239613 A | 10/2008 |
| JP | 2009-149629 A | 7/2009 |
| JP | 2009-149631 A | 7/2009 |
| JP | 2009-149632 A | 7/2009 |
| JP | 2009-526111 A | 7/2009 |
| JP | 2011-511821 A | 4/2011 |
| JP | 2011-201869 A | 10/2011 |
| KR | 2008-0005441 A | 1/2008 |
| KR | 2010-0123716 A | 11/2010 |
| KR | 2011-0042004 A | 4/2011 |
| TW | 200940554 A | 10/2009 |
| WO | 03/058667 A1 | 7/2003 |
| WO | 2004/043937 A1 | 5/2004 |
| WO | 2004/094389 A1 | 11/2004 |
| WO | 2005/113531 A1 | 12/2005 |
| WO | 2006/115232 A1 | 11/2006 |
| WO | 2007/069569 A1 | 6/2007 |
| WO | 2007/090773 A1 | 8/2007 |
| WO | 2008/023628 A1 | 2/2008 |
| WO | 2008/031743 A1 | 3/2008 |
| WO | 2009/100991 A1 | 8/2009 |

OTHER PUBLICATIONS

Zhang, M et al., "Highly-efficient solution-processed OLEDs based on new bipolar emitters," Chemical Communications, 2010, vol. 46, pp. 3923-3925.

Christian R. Goldsmith et al.; "C-H Bond Activation by a Ferric Methoxide Complex: Modeling the Rate-Determining Step in the Mechanism of Lipoxygenase"; J. Am. Chem. Soc. (Journal of the American Chemical Society); 2002; pp. 83-96; vol. 124, No. 1.

T. Onishi et al.; "A Method of Measuring an Energy Level"; High Molecular EL Materials—Development of Light-Emitting High Molecular Compounds; Dec. 25, 2004; pp. 64-67; Kyoritsu Shuppan, with English translation.

European Search Report (European Patent Application No. 11155124.8) dated Jun. 24, 2011, 7 pages.

* cited by examiner

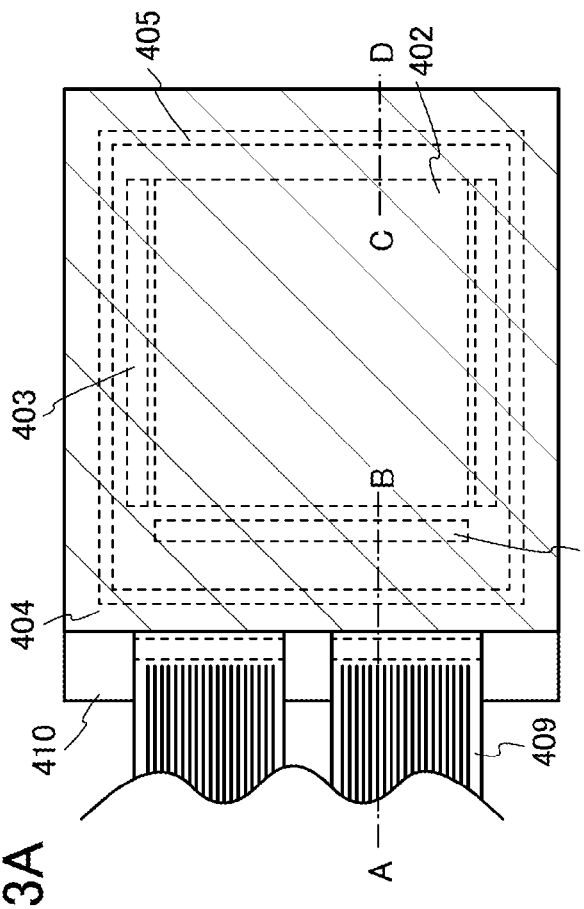
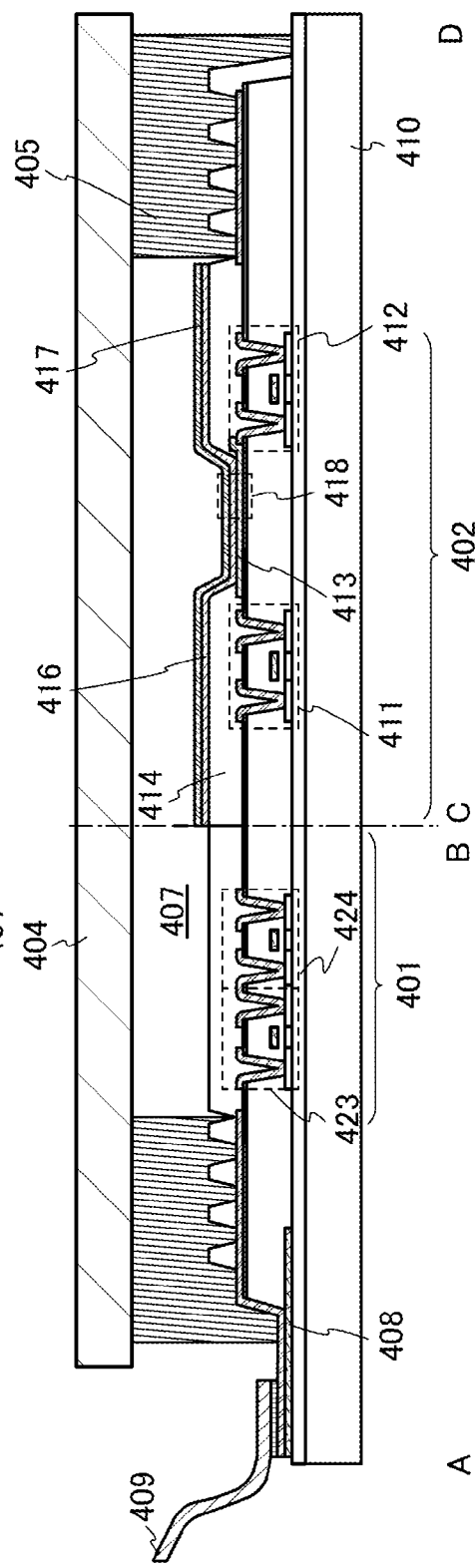
FIG. 3A
FIG. 3B

HETEROCYCLIC COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to a heterocyclic compound, a light-emitting element, a light-emitting device, an electronic device, and a lighting device.

2. Description of the Related Art

In recent years, research and development have been extensively conducted on light-emitting elements using electroluminescence (EL). In a basic structure of such a light-emitting element, a layer containing a light-emitting substance is interposed between a pair of electrodes. By applying voltage to this element, light emission from the light-emitting substance can be obtained.

Such a light-emitting element is of self-luminous type, and thus has advantages over a liquid crystal display in that visibility of pixels is high, backlight is not needed, and so on. Therefore, such a light-emitting element is regarded as being suitable as a flat panel display element. Besides, such a light-emitting element has advantages in that it can be manufactured to be thin and lightweight, and has very fast response speed.

Since such light-emitting elements can be formed in a film form, they make it possible to provide planar light emission. Thus, a large-area element can be easily formed. This is a feature that is difficult to obtain with point light sources typified by an incandescent lamp and an LED or linear light sources typified by a fluorescent lamp. Therefore, the light-emitting element is very effective for use as a surface light source applicable to a lighting device and the like.

Such light-emitting elements utilizing electroluminescence can be broadly classified according to whether a light-emitting substance is an organic compound or an inorganic compound. In the case of an organic EL element in which a layer containing an organic compound used as a light-emitting substance is provided between a pair of electrodes, application of voltage to the light-emitting element causes injection of electrons from a cathode and holes from an anode into the layer containing the organic compound having a light-emitting property and thus current flows. The injected electrons and holes then lead the organic compound having a light-emitting property to its excited state, whereby light emission is obtained from the excited organic compound having a light-emitting property.

Note that excited states of the organic compound include a singlet excited state and a triplet excited state. Light emission from the singlet excited state (S*) is referred to as fluorescence, and light emission from the triplet excited state (T*) is referred to as phosphorescence. The statistical generation ratio thereof in the light-emitting element is considered to be S*:T*=1:3.

At room temperature, a compound capable of converting a singlet excited state into luminescence (hereinafter, referred to as a fluorescent compound) exhibits only luminescence from the singlet excited state (fluorescence), and luminescence from the triplet excited state (phosphorescence) cannot be observed. Accordingly, the internal quantum efficiency (the ratio of the number of generated photons to the number of injected carriers) of a light-emitting element including the fluorescent compound is assumed to have a theoretical limit of 25%, on the basis of S*:T*=1:3.

In contrast, a compound capable of converting a triplet excited state into luminescence (hereinafter, referred to as a phosphorescent compound) exhibits luminescence from the triplet excited state (phosphorescence). Further, since intersystem crossing (i.e., transition from a singlet excited state to a triplet excited state) easily occurs in a phosphorescent compound, the internal quantum efficiency can be theoretically increased to 100%. That is, higher emission efficiency can be achieved than using a fluorescent compound. For this reason, light-emitting elements using a phosphorescent compound have been under active development recently so that high-efficiency light-emitting elements can be achieved.

When a light-emitting layer of a light-emitting element is formed using the phosphorescent compound described above, in order to suppress concentration quenching or quenching due to triplet-triplet annihilation of the phosphorescent compound, the light-emitting layer is usually formed such that the phosphorescent compound is dispersed in a matrix of another compound. Here, the compound serving as the matrix is called host material, and the compound dispersed in the matrix like the phosphorescent compound is called guest material.

When the phosphorescent compound is used as the guest material, the host material is required to have higher triplet excitation energy (larger difference in energy between the ground state and the triplet excited state) than the phosphorescent compound.

Since the singlet excitation energy (the difference in energy between the ground state and the singlet excited state) is greater than the triplet excitation energy, a substance that has high triplet excitation energy also has high singlet excitation energy. Therefore, the above substance that has high triplet excitation energy is also effective in a light-emitting element using a fluorescent compound as a light-emitting substance (guest material).

Studies have been conducted on compounds having a dibenzo[f,h]quinoxaline ring, which are examples of the host material used when a phosphorescent compound is a guest material (e.g., see Patent Documents 1 and 2).

REFERENCE

Patent Document

[Patent Document 1] PCT International Publication No. 03/058667
[Patent Document 2] Japanese Published Patent Application No. 2007-189001

SUMMARY OF THE INVENTION

The above compounds having a dibenzo[f,h]quinoxaline ring have a planar structure, thus being easily crystallized. A light-emitting element using a compound that is easily crystallized has a short lifetime. However, if another skeleton is directly bonded to the dibenzo[f,h]quinoxaline ring so that the compound has a sterically bulky structure, the conjugated system could possibly extend to cause a decrease in triplet excitation energy.

Further, in order to realize a light-emitting device, an electronic device, and a lighting device each having reduced power consumption and high reliability, a light-emitting element having low driving voltage, a light-emitting element having high emission efficiency, or a light-emitting element having a long lifetime has been demanded.

Therefore, an object of one embodiment of the present invention is to provide a novel heterocyclic compound which can be used in a light-emitting layer of a light-emitting element as a host material in which a light-emitting substance is dispersed, in particular, a novel heterocyclic compound which can be suitably used as a host material when a phosphorescent compound is used as a light-emitting substance.

Another object of one embodiment of the present invention is to provide a light-emitting element having low driving voltage. Yet another object of one embodiment of the present invention is to provide a light-emitting element having high emission efficiency. Another object of one embodiment of the present invention is to provide a light-emitting element having a long lifetime. Still another object of one embodiment of the present invention is to provide a light-emitting device, an electronic device, and a lighting device each having reduced power consumption by using the above light-emitting element.

One embodiment of the present invention is a compound in which two carrier-transport skeletons are bonded to a dibenzo[f,h]quinoxaline ring through respective arylene groups. Further, one embodiment of the present invention is a light-emitting element including the compound in which two carrier-transport skeletons are bonded to a dibenzo[f,h]quinoxaline ring through respective arylene groups.

An example of the carrier-transport skeleton is a π-electron rich heteroaromatic ring such as a carbazole ring, a dibenzofuran ring, or a dibenzothiophene ring.

A compound with a quinoxaline skeleton has a high electron-transport property, and use of such a compound for a light-emitting element enables the element to have low driving voltage. The compound according to one embodiment of the present invention includes two carrier-transport skeletons in addition to a dibenzo[f,h]quinoxaline ring, thus being able to accept carriers easily. Accordingly, use of the compound as a host material of a light-emitting layer enables electrons and holes to be surely recombined in the light-emitting layer, and therefore can suppress a decrease in lifetime of a light-emitting element, allowing the element to have a long lifetime.

Moreover, in this compound, a dibenzo[f,h]quinoxaline ring and a carrier-transport skeleton are bonded through an arylene group composed of a six-membered ring, such as a phenylene group or a biphenyldiyl group, so that conjugation is less likely to extend than in a compound in which a dibenzo[f,h]quinoxaline ring and a carrier-transport skeleton are directly bonded. This can prevent narrowing of the band gap between the highest occupied molecular orbital level (HOMO level) and the lowest unoccupied molecular orbital level (LUMO level) or a decrease in the triplet excitation energy level (T1 level) or the singlet excitation energy level (S1 level). Accordingly, the compound according to one embodiment of the present invention can be suitably used in a light-emitting layer as a host material in which a light-emitting substance is dispersed, especially as a host material in the case where a phosphorescent compound is used as a light-emitting substance. In addition, use of the compound for a light-emitting element enables the element to have a high emission efficiency.

Furthermore, this compound tends to have a steric structure because a dibenzo[f,h]quinoxaline ring and a carrier-transport skeleton are bonded through an arylene group. The steric structure makes a film of the compound less likely to be crystallized, thus preventing a decrease in the T1 level or the S1 level due to stacking. This also can prevent narrowing of the band gap between the HOMO level and the LUMO level or a decrease in the T1 level or the S1 level. Accordingly, use of the compound for a light-emitting element enables the element to have a high emission efficiency.

One embodiment of the present invention is a heterocyclic compound represented by the following general formula (G1).

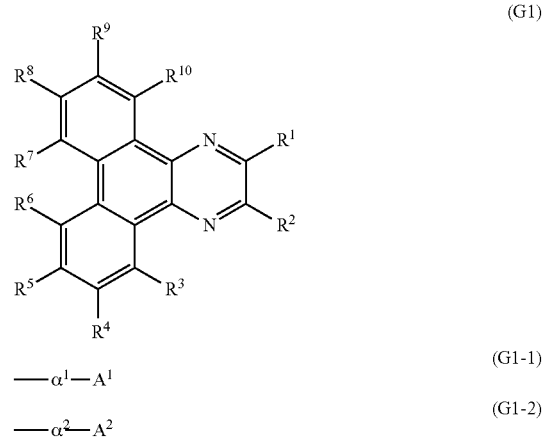

In the general formula (G1), any one of $R^1$ to $R^{10}$ represents a substituent represented by a general formula (G1-1), another one of $R^1$ to $R^{10}$ represents a substituent represented by a general formula (G1-2), and the others separately represent hydrogen, an alkyl group having 1 to 6 carbon atoms, a substituted or unsubstituted phenyl group, or a substituted or unsubstituted biphenyl group. Further, $\alpha^1$ in the general formula (G1-1) and $\alpha^2$ in the general formula (G1-2) separately represent a substituted or unsubstituted phenylene group or a substituted or unsubstituted biphenyldiyl group, and $A^1$ in the general formula (G1-1) and $A^2$ in the general formula (G1-2) separately represent a substituted or unsubstituted carbazolyl group, a substituted or unsubstituted dibenzothiophenyl group, or a substituted or unsubstituted dibenzofuranyl group.

In one embodiment of the present invention, when the phenylene group or the biphenyldiyl group in $\alpha^1$ and $\alpha^2$ has a substituent, the substituent is an alkyl group having 1 to 6 carbon atoms, a substituted or unsubstituted phenyl group, a substituted or unsubstituted biphenyl group, a substituted or unsubstituted carbazolyl group, a substituted or unsubstituted dibenzothiophenyl group, or a substituted or unsubstituted dibenzofuranyl group. Further, when the phenyl group, the biphenyl group, the carbazolyl group, the dibenzothiophenyl group, or the dibenzofuranyl group has a substituent, the substituent is an alkyl group having 1 to 6 carbon atoms, a phenyl group, or a biphenyl group.

In one embodiment of the present invention, when the carbazolyl group, the dibenzothiophenyl group, or the dibenzofuranyl group in $A^1$ and $A^2$ has a substituent, the substituent is an alkyl group having 1 to 6 carbon atoms, a phenyl group, or a biphenyl group.

In one embodiment of the present invention, when any of $R^1$ to $R^{10}$ represents a phenyl group or a biphenyl group, the phenyl group or the biphenyl group may include an alkyl group having 1 to 6 carbon atoms as a substituent.

Another embodiment of the present invention is a heterocyclic compound represented by the following general formula (G2-1).

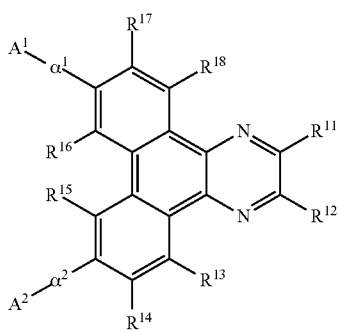

(G2-1)

In the general formula (G2-1), $R^{11}$ to $R^{18}$ separately represent hydrogen, an alkyl group having 1 to 6 carbon atoms, a substituted or unsubstituted phenyl group, or a substituted or unsubstituted biphenyl group, $\alpha^1$ and $\alpha^2$ separately represent a substituted or unsubstituted phenylene group or a substituted or unsubstituted biphenyldiyl group, and $A^1$ and $A^2$ separately represent a substituted or unsubstituted carbazolyl group, a substituted or unsubstituted dibenzothiophenyl group, or a substituted or unsubstituted dibenzofuranyl group.

When any of $R^{11}$ to $R^{18}$ in the general formula (G2-1) represents a phenyl group or a biphenyl group, the phenyl group or the biphenyl group may include an alkyl group having 1 to 6 carbon atoms as a substituent.

Another embodiment of the present invention is a heterocyclic compound represented by the following general formula (G2-2).

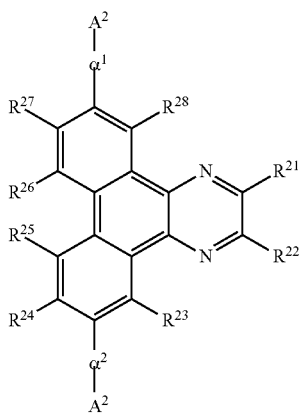

(G2-2)

In the general formula (G2-2), $R^{21}$ to $R^{28}$ separately represent hydrogen, an alkyl group having 1 to 6 carbon atoms, a substituted or unsubstituted phenyl group, or a substituted or unsubstituted biphenyl group, $\alpha^1$ and $\alpha^2$ separately represent a substituted or unsubstituted phenylene group or a substituted or unsubstituted biphenyldiyl group, and $A^1$ and $A^2$ separately represent a substituted or unsubstituted carbazolyl group, a substituted or unsubstituted dibenzothiophenyl group, or a substituted or unsubstituted dibenzofuranyl group.

When any of $R^{21}$ to $R^{28}$ in the general formula (G2-2) represents a phenyl group or a biphenyl group, the phenyl group or the biphenyl group may include an alkyl group having 1 to 6 carbon atoms as a substituent.

It is preferable that $\alpha^1$ in the general formula (G1-1), $\alpha^2$ in the general formula (G1-2), and $\alpha^1$ and $\alpha^2$ in the general formulae (G2-1) and (G2-2) be separately represented by a general formula ($\alpha$-1) or a general formula ($\alpha$-2).

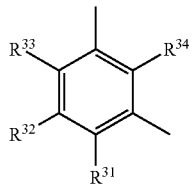

($\alpha$-1)

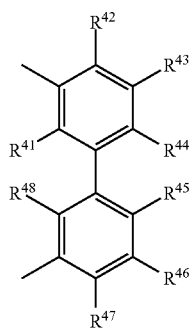

($\alpha$-2)

$R^{31}$ to $R^{34}$ in the general formula ($\alpha$-1) and $R^{41}$ to $R^{48}$ in the general formula ($\alpha$-2) separately represent hydrogen, an alkyl group having 1 to 6 carbon atoms, a substituted or unsubstituted phenyl group, a substituted or unsubstituted biphenyl group, a substituted or unsubstituted carbazolyl group, a substituted or unsubstituted dibenzothiophenyl group, or a substituted or unsubstituted dibenzofuranyl group.

When any of $R^{31}$ to $R^{34}$ in the general formula ($\alpha$-1) and $R^{41}$ to $R^{48}$ in the general formula ($\alpha$-2) represents a phenyl group, a biphenyl group, a carbazolyl group, a dibenzothiophenyl group, or a dibenzofuranyl group, the phenyl group, the biphenyl group, the carbazolyl group, the dibenzothiophenyl group, or the dibenzofuranyl group may include an alkyl group having 1 to 6 carbon atoms, a phenyl group, or a biphenyl group as a substituent.

It is preferable that $A^1$ in the general formula (G1-1), $A^2$ in the general formula (G1-2), and $A^1$ and $A^2$ in the general formulae (G2-1) and (G2-2) be separately represented by any one of general formulae (I-1) to (I-3).

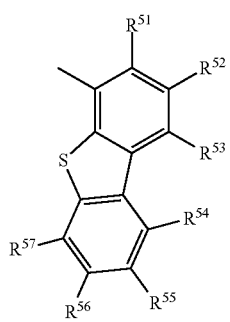

(I-1)

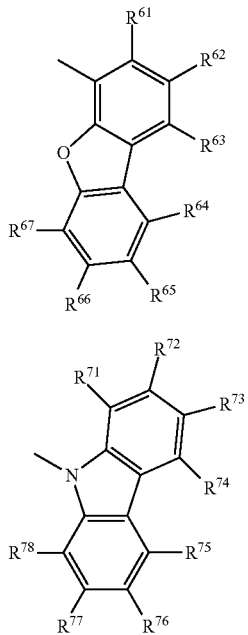

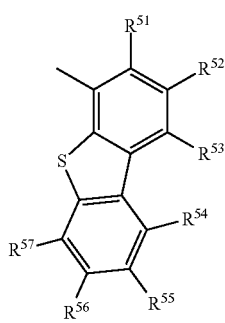

$R^{51}$ to $R^{57}$ in the general formula (1-1), $R^{61}$ to $R^{67}$ in the general formula (1-2), and $R^{71}$ to $R^{78}$ in the general formula (1-3) separately represent hydrogen, an alkyl group having 1 to 6 carbon atoms, a substituted or unsubstituted phenyl group, or a substituted or unsubstituted biphenyl group.

When any of $R^{51}$ to $R^{57}$ in the general formula (1-1), $R^{61}$ to $R^{67}$ in the general formula (1-2), and $R^{71}$ to $R^{78}$ in the general formula (1-3) represents a phenyl group or a biphenyl group, the phenyl group or the biphenyl group may include an alkyl group having 1 to 6 carbon atoms as a substituent.

It is particularly preferable that $A^1$ in the general formula (G1-1), $A^2$ in the general formula (G1-2), and $A^1$ and $A^2$ in the general formulae (G2-1) and (G2-2) each be represented by the general formula (I-1).

$R^{51}$ to $R^{57}$ in the general formula (1-1) separately represent hydrogen, an alkyl group having 1 to 6 carbon atoms, a substituted or unsubstituted phenyl group, or a substituted or unsubstituted biphenyl group.

It is particularly preferable that $A^1$ in the general formula (G1-1), $A^2$ in the general formula (G1-2), and $A^1$ and $A^2$ in the general formulae (G2-1) and (G2-2) each be represented by the general formula (1-2).

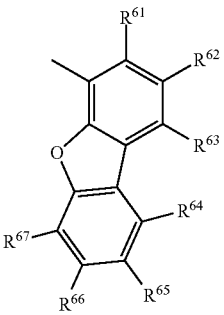

$R^{61}$ to $R^{67}$ in the general formula (1-2) separately represent hydrogen, an alkyl group having 1 to 6 carbon atoms, a substituted or unsubstituted phenyl group, or a substituted or unsubstituted biphenyl group.

It is particularly preferable that $A^1$ in the general formula (G1-1), $A^2$ in the general formula (G1-2), and $A^1$ and $A^2$ in the general formulae (G2-1) and (G2-2) each be represented by the general formula (1-3).

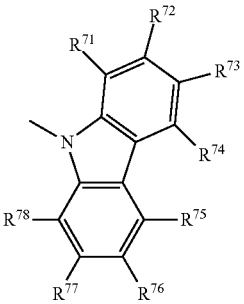

$R^{71}$ to $R^{78}$ in the general formula (1-3) separately represent hydrogen, an alkyl group having 1 to 6 carbon atoms, a substituted or unsubstituted phenyl group, or a substituted or unsubstituted biphenyl group.

Another embodiment of the present invention is a light-emitting element including the above-described heterocyclic compound. Particularly preferred is a light-emitting element including a light-emitting layer between an anode and a cathode, in which the light-emitting layer contains a light-emitting substance and the heterocyclic compound according to one embodiment of the present invention.

Further preferred is a light-emitting element including a light-emitting layer between an anode and a cathode, in which the light-emitting layer contains a light-emitting substance, an electron-transport compound, and a hole-transport compound. The electron-transport compound is a heterocyclic compound according to one embodiment of the present invention. The hole-transport compound has a higher hole-transport property than the electron-transport compound and includes a carbazole skeleton, a triarylamine skeleton, a dibenzothiophene skeleton, or a dibenzofuran skeleton.

Here, a layer in contact with the light-emitting layer on the anode side preferably contains the same hole-transport compound as the light-emitting layer.

In the above light-emitting element, a layer in contact with the light-emitting layer on the cathode side preferably contains the heterocyclic compound according to one embodiment of the present invention.

Another embodiment of the present invention is a light-emitting device including the above-described light-emitting element in a light-emitting portion. Another embodiment of the present invention is an electronic device including the light-emitting device in a display portion. Another embodiment of the present invention is a lighting device including the light-emitting device in a light-emitting portion.

A light-emitting element including the heterocyclic compound according to one embodiment of the present invention has low driving voltage, high emission efficiency, or a long lifetime, and thus can provide a light-emitting device with low power consumption. For a similar reason, an electronic device and a lighting device with low power consumption can be provided by employing one embodiment of the present invention.

The light-emitting device in this specification covers an image display device using a light-emitting element and also the following devices: a module including a light-emitting element to which a connector such as an anisotropic conductive film, a TAB (tape automated bonding) tape, or a TCP (tape carrier package) is attached; a module in which the top of a TAB tape or a TCP is provided with a printed wiring board; a module in which an IC (integrated circuit) is directly mounted on a light-emitting element by a COG (chip on glass) technique; and further a light-emitting device used for a lighting device and the like.

One embodiment of the present invention provides a novel heterocyclic compound which can be used in a light-emitting layer of a light-emitting element as a host material in which a light-emitting substance is dispersed. Another embodiment of the present invention provides a light-emitting element having low driving voltage. Yet another embodiment of the present invention provides a light-emitting element having high emission efficiency. Still another embodiment of the present invention provides a light-emitting element having a long lifetime. By using the light-emitting element, another embodiment of the present invention provides a light-emitting device, an electronic device, and a lighting device each having reduced power consumption.

BRIEF DESCRIPTION OF THE DRAWINGS

FIGS. 3A and 3B illustrate a light-emitting device according to one embodiment of the present invention.

DETAILED DESCRIPTION OF THE INVENTION

Figure 1A:
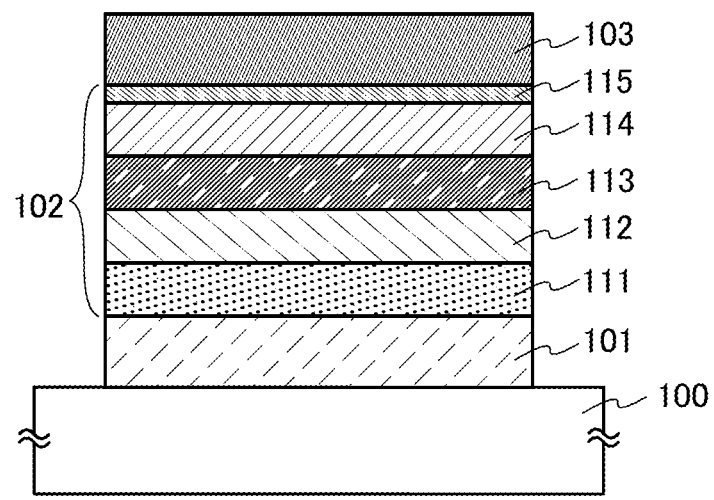
FIGS. 1A and 1B each illustrate a light-emitting element according to one embodiment of the present invention.

Hereinafter, embodiments and examples of the present invention will be described in detail with reference to the accompanying drawings. Note that the present invention is not limited to the following description, and it will be easily understood by those skilled in the art that various changes and modifications can be made without departing from the spirit and scope of the present invention. Therefore, the present invention should not be construed as being limited to the description in the following embodiments and examples.

(Embodiment 1)

In this embodiment, a heterocyclic compound according to one embodiment of the present invention is described.

One embodiment of the present invention is a heterocyclic compound represented by the general formula (G1).

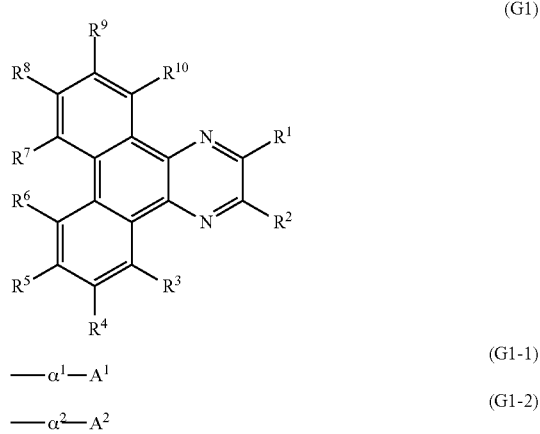

In the general formula (G1), any one of $R^1$ to $R^{10}$ represents a substituent represented by the general formula (G1-1), another one of $R^1$ to $R^{10}$ represents a substituent represented by the general formula (G1-2), and the others separately represent hydrogen, an alkyl group having 1 to 6 carbon atoms, a substituted or unsubstituted phenyl group, or a substituted or unsubstituted biphenyl group. Further, $\alpha^1$ in the general formula (G1-1) and $\alpha^2$ in the general formula (G1-2) separately represent a substituted or unsubstituted phenylene group or a substituted or unsubstituted biphenyldiyl group, and $A^1$ in the general formula (G1-1) and $A^2$ in the general formula (G1-2) separately represent a substituted or unsubstituted carbazolyl group, a substituted or unsubstituted dibenzothiophenyl group, or a substituted or unsubstituted dibenzofuranyl group.

When the phenylene group or the biphenyldiyl group in $\alpha^1$ in the general formula (G1-1) and $\alpha^2$ in the general formula (G1-2) has a substituent, the substituent is an alkyl group having 1 to 6 carbon atoms, a substituted or unsubstituted phenyl group, a substituted or unsubstituted biphenyl group, a substituted or unsubstituted carbazolyl group, a substituted or unsubstituted dibenzothiophenyl group, or a substituted or unsubstituted dibenzofuranyl group. Further, when the phenyl group, the biphenyl group, the carbazolyl group, the dibenzothiophenyl group, or the dibenzofuranyl group has a substituent, the substituent is an alkyl group having 1 to 6 carbon atoms, a phenyl group, or a biphenyl group.

When the carbazolyl group, the dibenzothiophenyl group, or the dibenzofuranyl group in $A^1$ in the general formula (G1-1) and $A^2$ in the general formula (G1-2) has a substituent, the substituent is an alkyl group having 1 to 6 carbon atoms, a phenyl group, or a biphenyl group.

When any of $R^1$ to $R^{10}$ in the general formula (G1) represents a phenyl group or a biphenyl group, the phenyl group or the biphenyl group may include an alkyl group having 1 to 6 carbon atoms as a substituent.

Heterocyclic compounds represented by the following general formulae (G2-1) and (G2-2) are easily synthesized and thus particularly preferred among heterocyclic compounds represented by the general formula (G1).

That is, another embodiment of the present invention is a heterocyclic compound represented by the general formula (G2-1). This structure is preferred because, as in the heterocyclic compound represented by the general formula (G2-1), substitution at the 7- and 10-positions of the dibenzo[f,h]quinoxaline ring (specifically, a substituent represented by the general formula (G1-1) is bonded to one of the 7- and 10-positions and a substituent represented by the general formula (G1-2) is bonded to the other of the 7- and 10-positions) results in a steric structure, leading to increase in amorphousness.

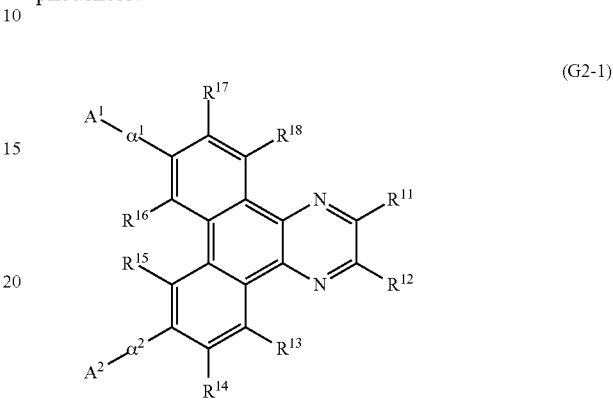

In the general formula (G2-1), $R^{11}$ to $R^{18}$ separately represent hydrogen, an alkyl group having 1 to 6 carbon atoms, a substituted or unsubstituted phenyl group, or a substituted or unsubstituted biphenyl group, $\alpha^1$ and $\alpha^2$ separately represent a substituted or unsubstituted phenylene group or a substituted or unsubstituted biphenyldiyl group, and $A^1$ and $A^2$ separately represent a substituted or unsubstituted carbazolyl group, a substituted or unsubstituted dibenzothiophenyl group, or a substituted or unsubstituted dibenzofuranyl group.

When any of $R^{11}$ to $R^{18}$ in the general formula (G2-1) represents a phenyl group or a biphenyl group, the phenyl group or the biphenyl group may include an alkyl group having 1 to 6 carbon atoms as a substituent.

Another embodiment of the present invention is a heterocyclic compound represented by the general formula (G2-2).

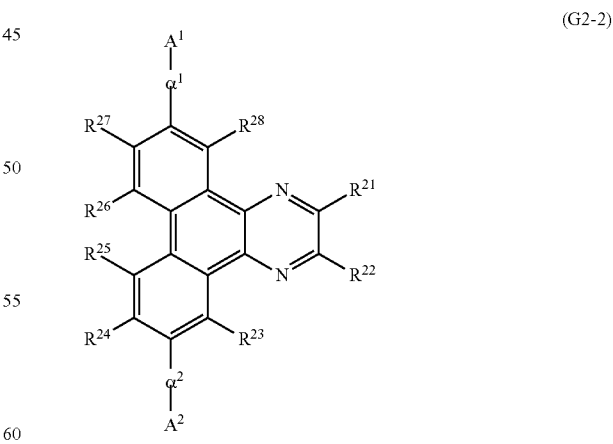

In the general formula (G2-2), $R^{21}$ to $R^{28}$ separately represent hydrogen, an alkyl group having 1 to 6 carbon atoms, a substituted or unsubstituted phenyl group, or a substituted or unsubstituted biphenyl group, $\alpha^1$ and $\alpha^2$ separately represent a substituted or unsubstituted phenylene group or a substituted or unsubstituted biphenyldiyl group, and $A^1$ and $A^2$ separately represent a substituted or unsubstituted carbazolyl group, a substituted or unsubstituted dibenzothiophenyl group, or a substituted or unsubstituted dibenzofuranyl group.

When any of $R^{21}$ to $R^{28}$ in the general formula (G2-2) represents a phenyl group or a biphenyl group, the phenyl group or the biphenyl group may include an alkyl group having 1 to 6 carbon atoms as a substituent.

In each of $\alpha^1$ in the general formula (G1-1), $\alpha^2$ in the general formula (G1-2), and $\alpha^1$ and $\alpha^2$ in the general formulae (G2-1) and (G2-2), the benzene skeleton is preferably para-substituted, in which case the carrier-transport property can be improved.

Alternatively, in each of $\alpha^1$ in the general formula (G1-1), $\alpha^2$ in the general formula (G1-2), and $\alpha^1$ and $\alpha^2$ in the general formulae (G2-1) and (G2-2), the benzene skeleton is preferably meta-substituted, in which case conjugation is less likely to extend between substituents linked by the benzene skeleton (the dibenzo[f,h]quinoxaline ring and the carrier-transport skeleton), which results in a high T1 level, a high S1 level, or a wide bandgap between the HOMO level and the LUMO level.

Therefore, it is preferable that $\alpha^1$ in the general formula (G1-1), $\alpha^2$ in the general formula (G1-2), and $\alpha^1$ and $\alpha^2$ in the general formulae (G2-1) and (G2-2) be separately represented by the general formula ($\alpha$-1) or the general formula ($\alpha$-2).

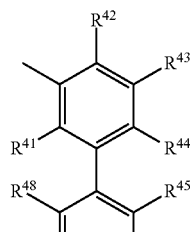

($\alpha$-1)

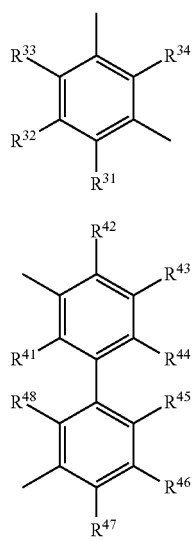

($\alpha$-2)

$R^{31}$ to $R^{34}$ in the general formula ($\alpha$-1) and $R^{41}$ to $R^{48}$ in the general formula ($\alpha$-2) separately represent hydrogen, an alkyl group having 1 to 6 carbon atoms, a substituted or unsubstituted phenyl group, a substituted or unsubstituted biphenyl group, a substituted or unsubstituted carbazolyl group, a substituted or unsubstituted dibenzothiophenyl group, or a substituted or unsubstituted dibenzofuranyl group.

When any of $R^{31}$ to $R^{34}$ in the general formula ($\alpha$-1) and $R^{41}$ to $R^{48}$ in the general formula ($\alpha$-2) represents a phenyl group, a biphenyl group, a carbazolyl group, a dibenzothiophenyl group, or a dibenzofuranyl group, the phenyl group, the biphenyl group, the carbazolyl group, the dibenzothiophenyl group, or the dibenzofuranyl group may include an alkyl group having 1 to 6 carbon atoms, a phenyl group, or a biphenyl group as a substituent.

It is preferable that $A^1$ in the general formula (G1-1), $A^2$ in the general formula (G1-2), and $A^1$ and $A^2$ in the general formulae (G2-1) and (G2-2) be separately represented by any one of the general formulae (1-1) to (1-3).

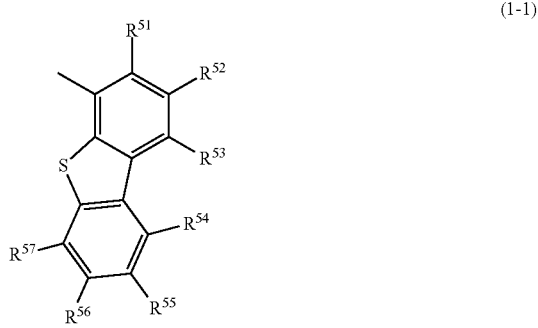

(1-1)

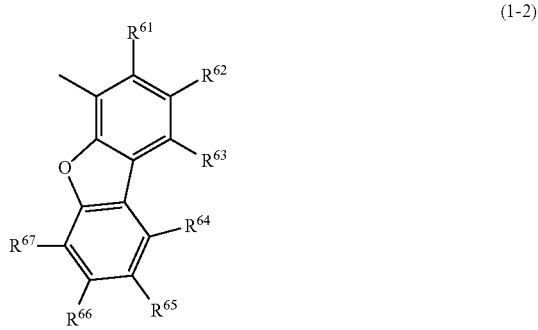

(1-2)

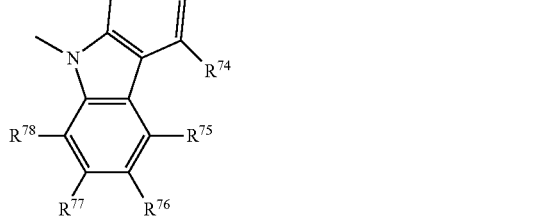

(1-3)

In the general formulae (1-1) to (1-3), $R^{51}$ to $R^{57}$, $R^{61}$ to $R^{67}$, and $R^{71}$ to $R^{78}$ separately represent hydrogen, an alkyl group having 1 to 6 carbon atoms, a substituted or unsubstituted phenyl group, or a substituted or unsubstituted biphenyl group.

$A^1$ or $A^2$ is preferably bonded to $\alpha^1$ or $\alpha^2$ through the 4-position of the dibenzothiophene skeleton, the 4-position of the dibenzofuran skeleton, or the 9-position of the carbazole skeleton, as in the general formulae (1-1) to (1-3), because conjugation is less likely to extend than in cases where $A^1$ or $A^2$ is bonded to $\alpha^1$ or $\alpha^2$ through other substitution sites, and also because the heterocyclic compound according to one embodiment of the present invention can be easily synthesized. In particular, the heterocyclic compound according to one embodiment of the present invention and employing the structure in the general formula (1-1) or the general formula (1-2) is electrochemically stable and thus preferred. In particular, the heterocyclic compound according to one embodiment of the present invention and employing the structure in the general formula (1-3) has a high hole-transport property, and therefore is preferred.

$A^1$ in the general formula (G1-1) and $A^2$ in the general formula (G1-2) preferably have the same structure, in which case synthesis is especially facilitated. It is thus preferable that $A^1$ in the general formula (G1-1) and $A^2$ in the general formula (G1-2) each be represented by the general formula (1-1) below.

Further, in the general formulae (G2-1) and (G2-2), $A^1$ and $A^2$ preferably have the same structure, in which case synthesis is especially facilitated. It is thus preferable that $A^1$ and $A^2$ in the general formulae (G2-1) and (G2-2) each be represented by the following general formula (1-1).

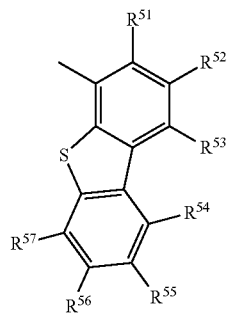

(1-1)

$R^{51}$ to $R^{57}$ in the general formula (1-1) separately represent hydrogen, an alkyl group having 1 to 6 carbon atoms, a substituted or unsubstituted phenyl group, or a substituted or unsubstituted biphenyl group.

Alternatively, $A^1$ in the general formula (G1-1) and $A^2$ in the general formula (G1-2) are each preferably represented by the general formula (I-2). Further, $A^1$ and $A^2$ in the general formulae (G2-1) and (G2-2) are each preferably represented by the general formula (1-2).

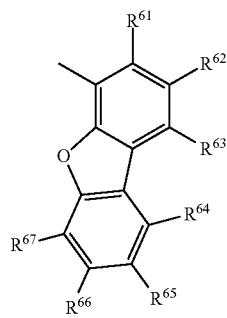

(1-2)

$R^{61}$ to $R^{67}$ in the general formula (1-2) separately represent hydrogen, an alkyl group having 1 to 6 carbon atoms, a substituted or unsubstituted phenyl group, or a substituted or unsubstituted biphenyl group.

Alternatively, $A^1$ in the general formula (G1-1) and $A^2$ in the general formula (G1-2) are each preferably represented by the general formula (1-3). Further, $A^1$ and $A^2$ in the general formulae (G2-1) and (G2-2) are each preferably represented by the general formula (1-3).

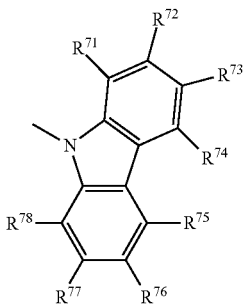

(1-3)

$R^{71}$ to $R^{78}$ in the general formula (1-3) separately represent hydrogen, an alkyl group having 1 to 6 carbon atoms, a substituted or unsubstituted phenyl group, or a substituted or unsubstituted biphenyl group.

In the general formulae given above, $R^1$ to $R^{18}$, $R^{21}$ to $R^{28}$, $R^{51}$ to $R^{57}$, $R^{61}$ to $R^{67}$, and $R^{71}$ to $R^{78}$ separately represent hydrogen, an alkyl group having 1 to 6 carbon atoms, a substituted or unsubstituted phenyl group, or a substituted or unsubstituted biphenyl group. Examples of specific structures of $R^1$ to $R^{18}$, $R^{21}$ to $R^{28}$, $R^{51}$ to $R^{57}$, $R^{61}$ to $R^{67}$, and $R^{71}$ to $R^{78}$ include substituents represented by structural formulae (2-1) to (2-17).

(2-1)

(2-2)

(2-3)

(2-4)

(2-5)

(2-6)

(2-7)

(2-8)

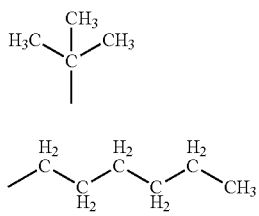
(2-9)

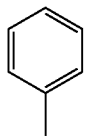
(2-10)

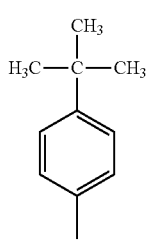
(2-11)

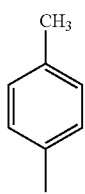
(2-12)

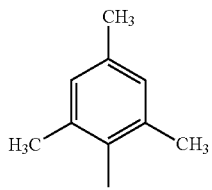
(2-13)

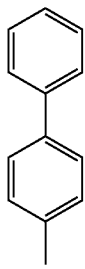
(2-14)

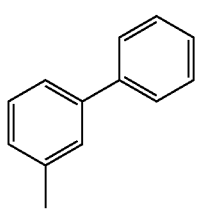
(2-15)

(2-16)

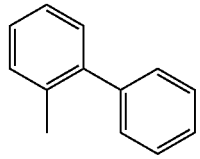
(2-17)

In the general formulae given above, $R^{31}$ to $R^{34}$ and $R^{41}$ to $R^{48}$ separately represent hydrogen, an alkyl group having 1 to 6 carbon atoms, a substituted or unsubstituted phenyl group, a substituted or unsubstituted biphenyl group, a substituted or unsubstituted carbazolyl group, a substituted or unsubstituted dibenzothiophenyl group, or a substituted or unsubstituted dibenzofuranyl group. Examples of specific structures of $R^{31}$ to $R^{34}$ and $R^{41}$ to $R^{48}$ include substituents represented by structural formulae (2-1) to (2-20).

(2-1)

(2-2)

(2-3)

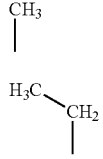
(2-4)

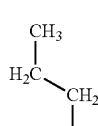
(2-5)

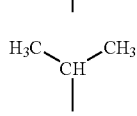
(2-6)

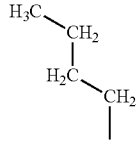
(2-7)

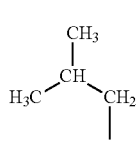
(2-8)

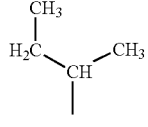
(2-9)

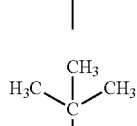

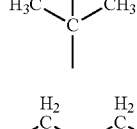
(2-9)

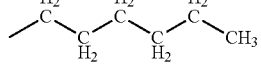
(2-10)

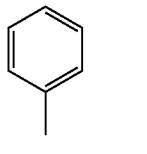 (2-11)

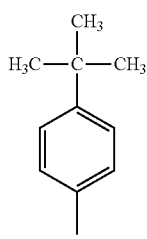 (2-12)

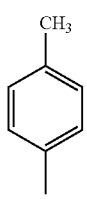 (2-13)

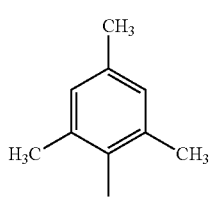 (2-14)

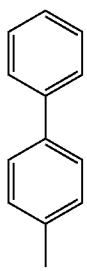 (2-15)

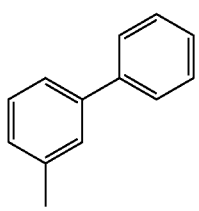 (2-16)

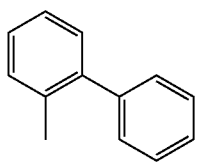 (2-17)

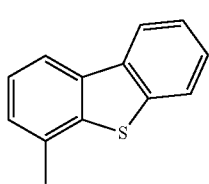 (2-18)

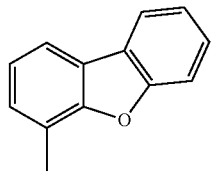 (2-19)

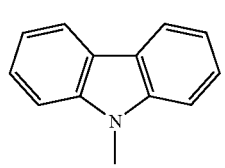 (2-20)

In the general formulae given above, $\alpha^1$ and $\alpha^2$ separately represent a substituted or unsubstituted phenylene group or a substituted or unsubstituted biphenyldiyl group. The phenylene group and the biphenyldiyl group may include an alkyl group having 1 to 6 carbon atoms, a substituted or unsubstituted phenyl group, a substituted or unsubstituted biphenyl group, a substituted or unsubstituted carbazolyl group, a substituted or unsubstituted dibenzothiophenyl group, or a substituted or unsubstituted dibenzofuranyl group as a substituent.

All the phenylene groups included in $\alpha^1$ and $\alpha^2$ are preferably meta-substituted, in which case the heterocyclic compound according to one embodiment of the present invention has a high T1 level. Alternatively, all the phenylene groups included in $\alpha^1$ and $\alpha^2$ are preferably para-substituted, in which case a light-emitting element including the heterocyclic compound according to one embodiment of the present invention can have low driving voltage.

Examples of specific structures of $\alpha^1$ and $\alpha^2$ are represented by structural formulae (3-1) to (3-9).

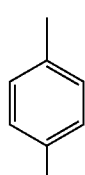 (3-1)

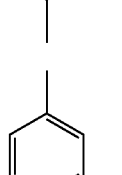 (3-2)

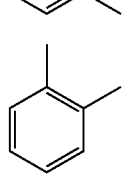 (3-3)

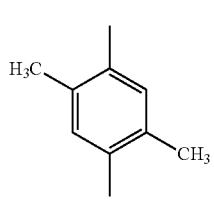 (3-4)

-continued
(3-5)
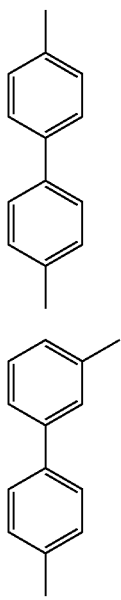
(3-6)
(3-7)
(3-8)
(3-9)
(100)
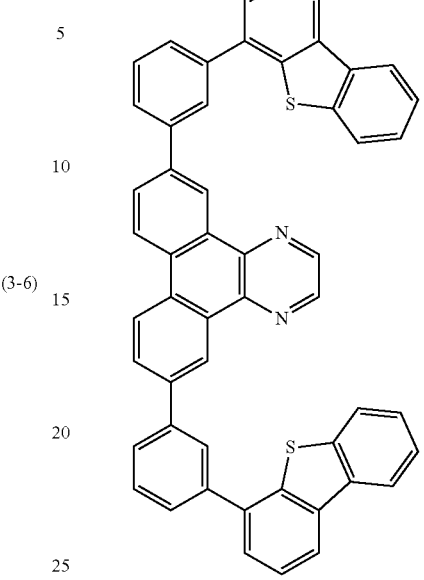
(101)
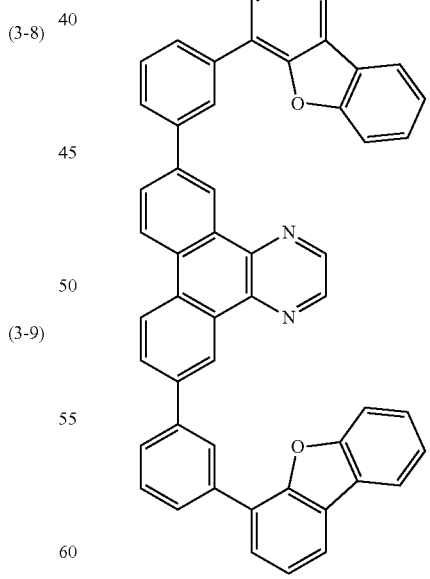
Examples of the heterocyclic compound represented by the general formula (G1) specifically include, but are not limited to, heterocyclic compounds represented by structural formulae (100) to (116), (120) to (123), (130) to (143), and (150) to (153).

(102)
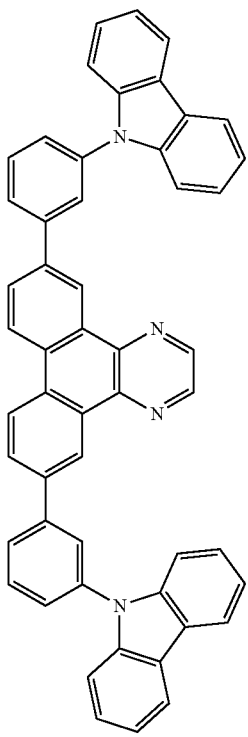
(103)
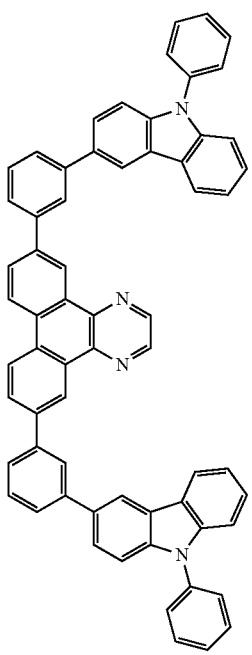
(104)
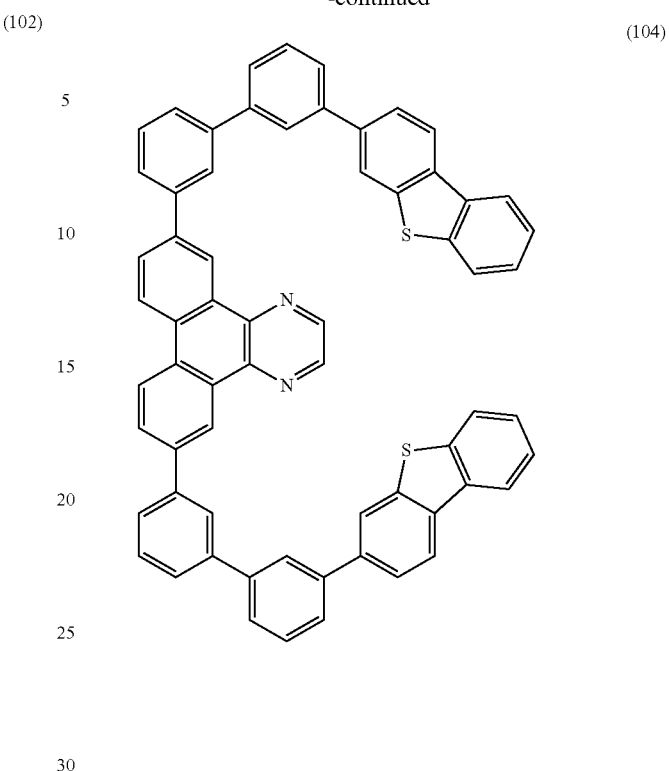
(105)
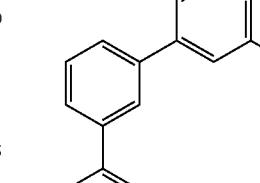

(106)
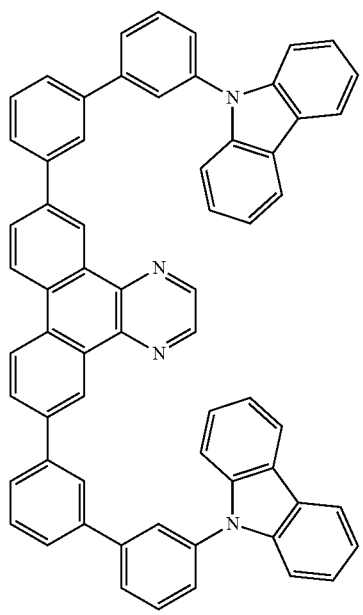
(107)
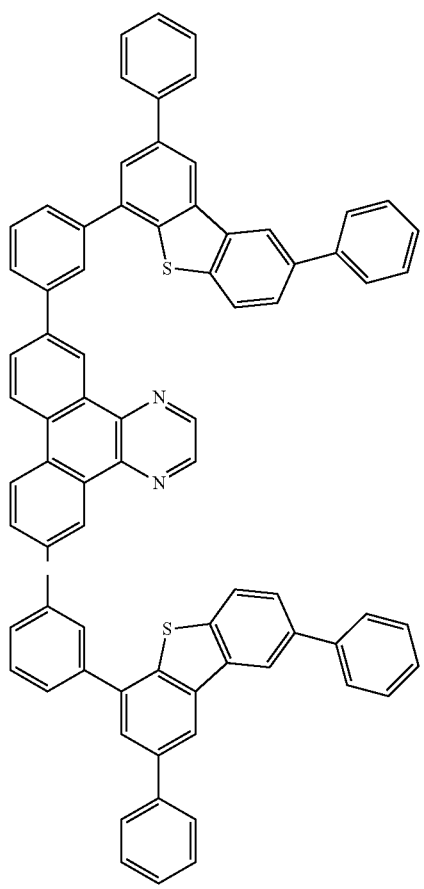
(108)
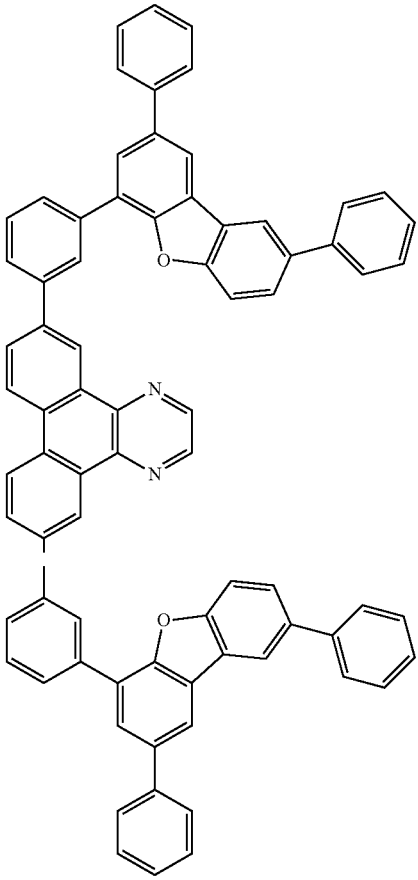
(109)
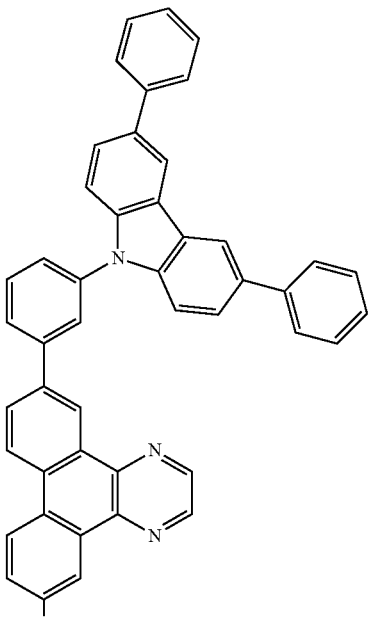

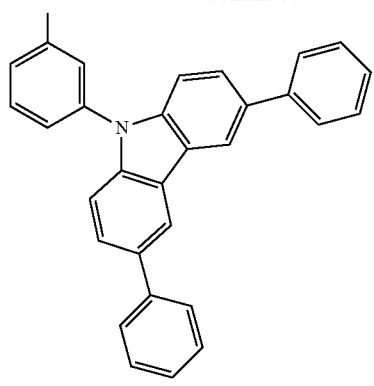
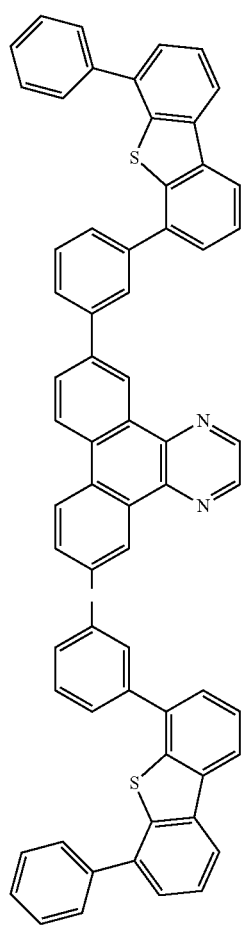
(110)
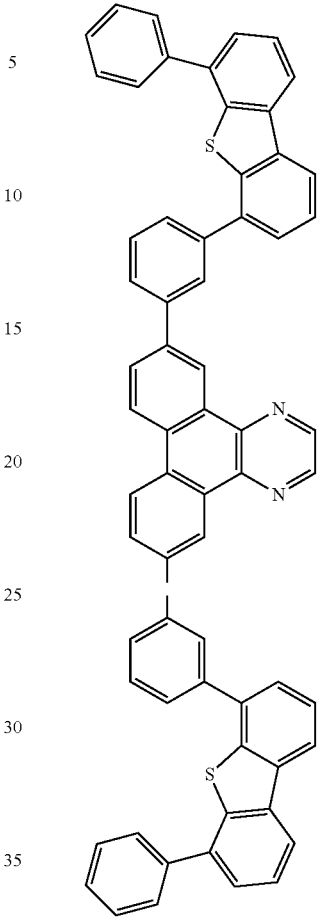
(111)
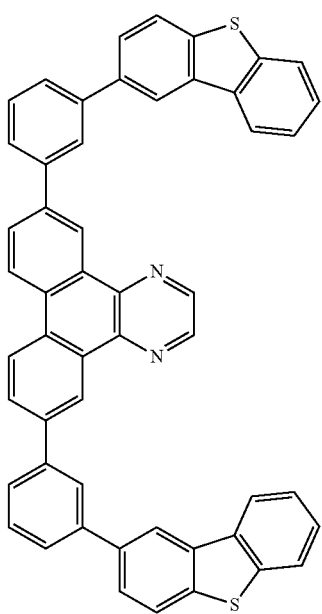
(112)

(113)
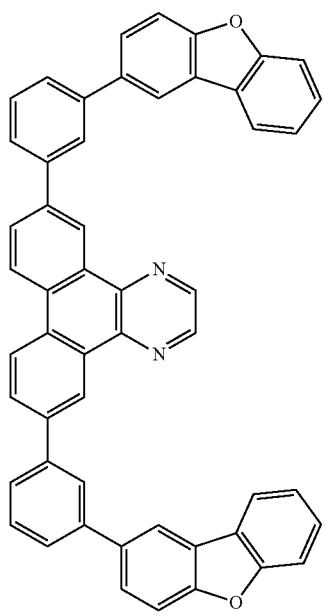
(115)
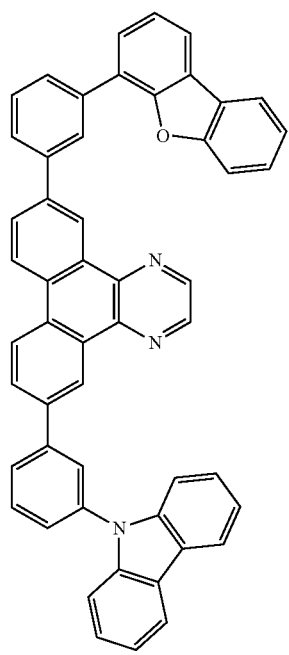
(114)
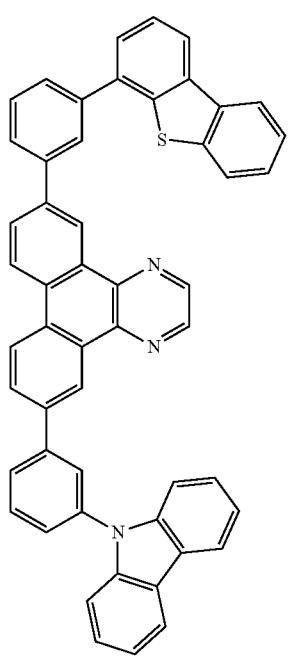
(116)
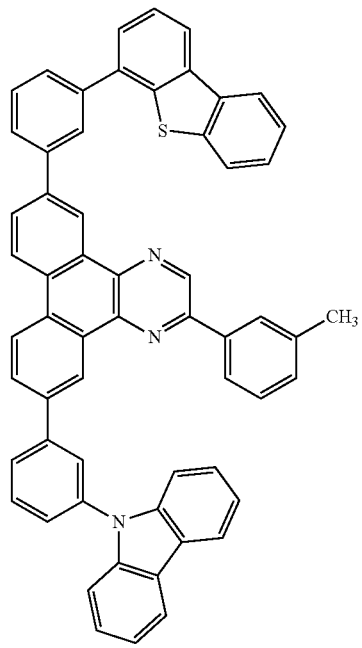

-continued
(120)
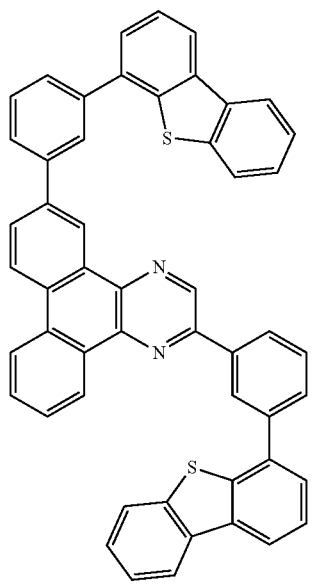
(121)
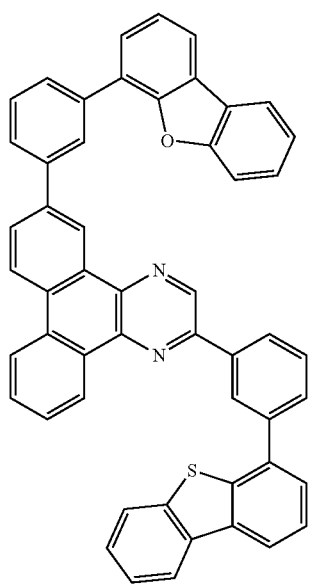
(122)
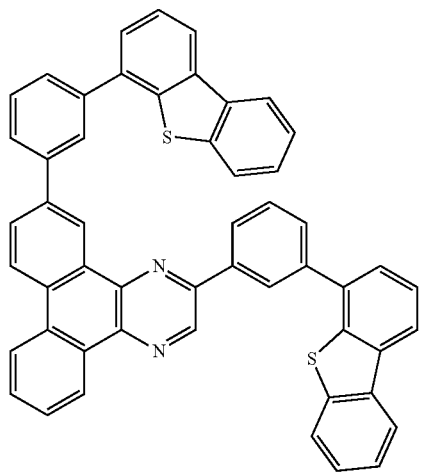
-continued
(123)
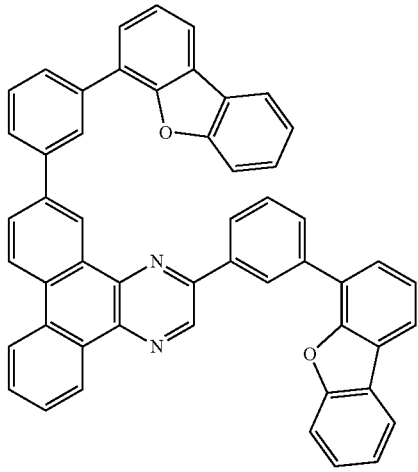
(130)
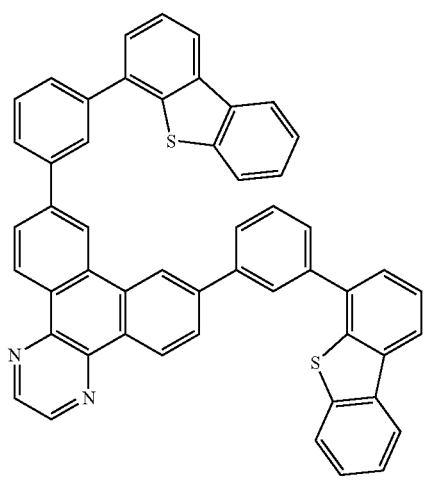
(131)
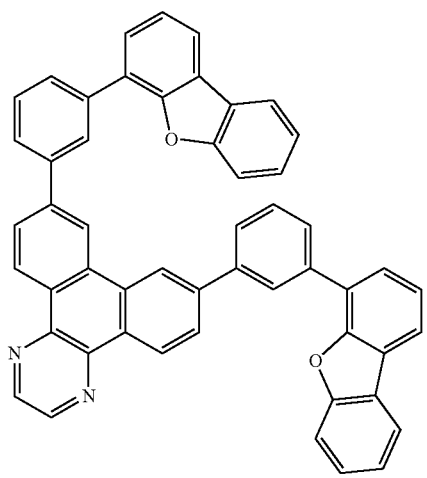

(132)
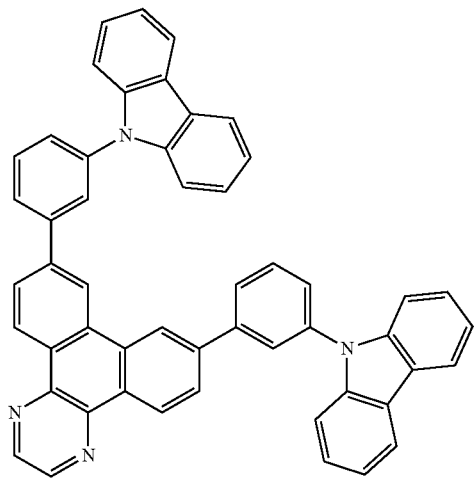
(133)
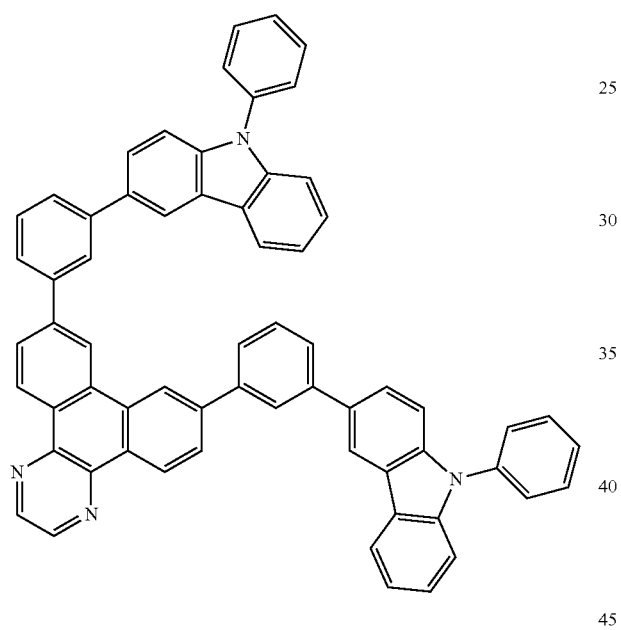
(134)
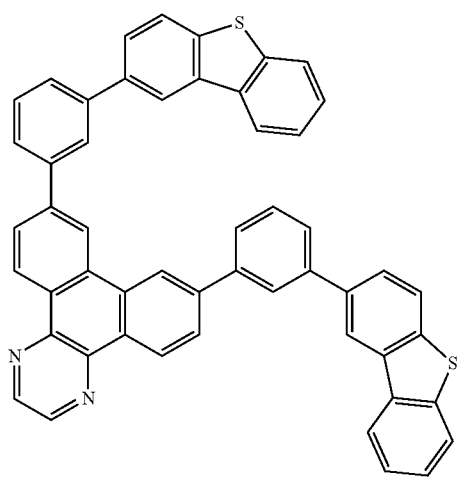
(135)
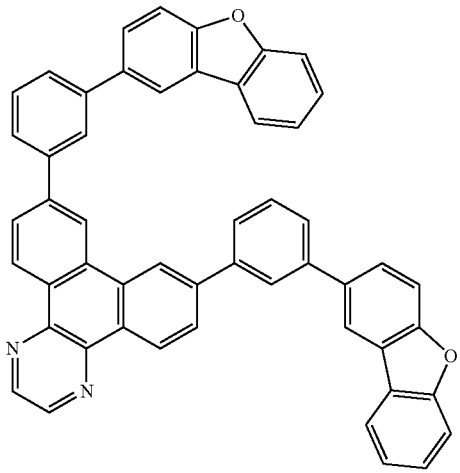
(136)
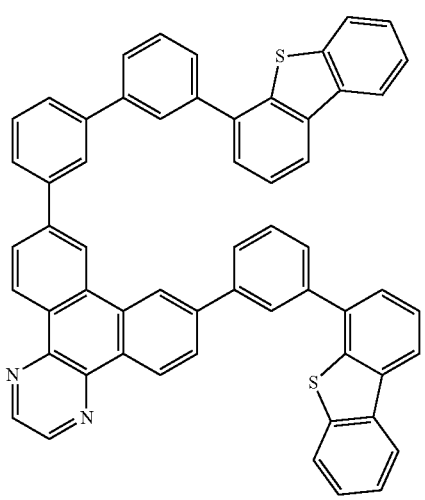
(137)
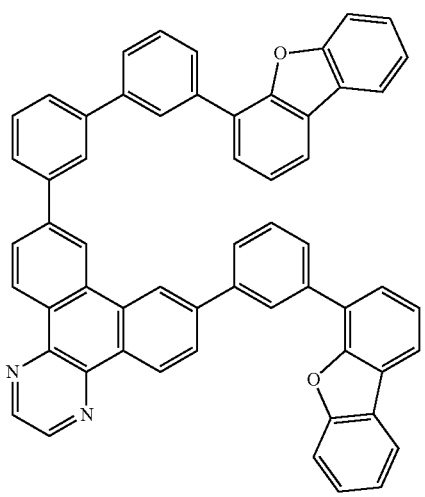

(138)
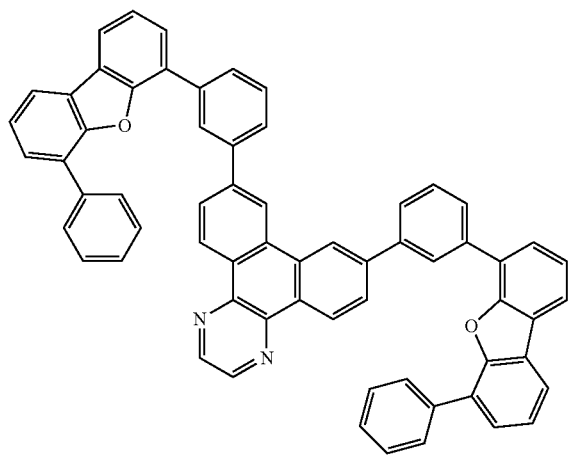
(139)
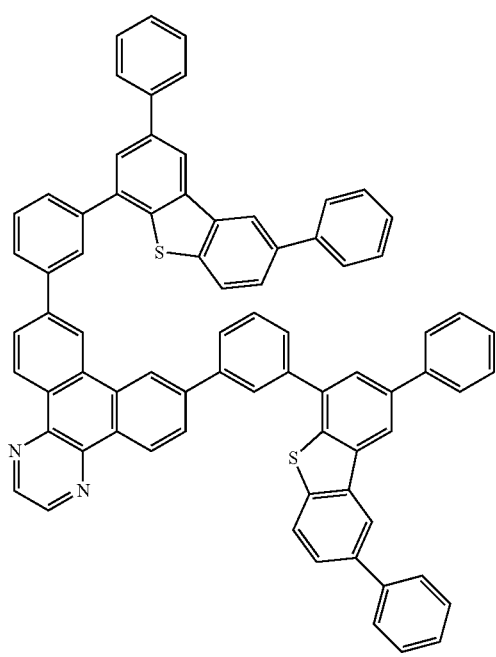
(140)
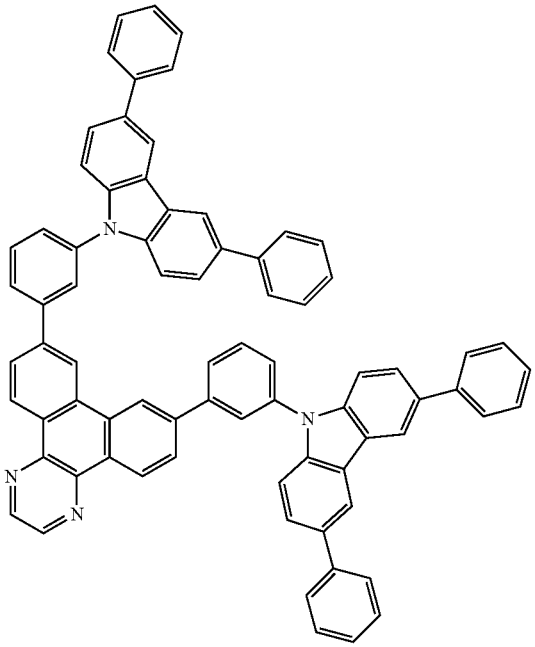
(141)
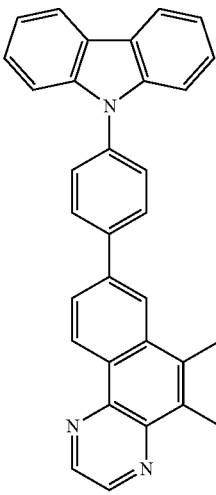
(142)
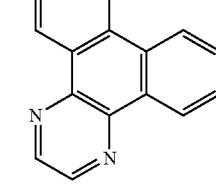

(143)

(150)

(151)

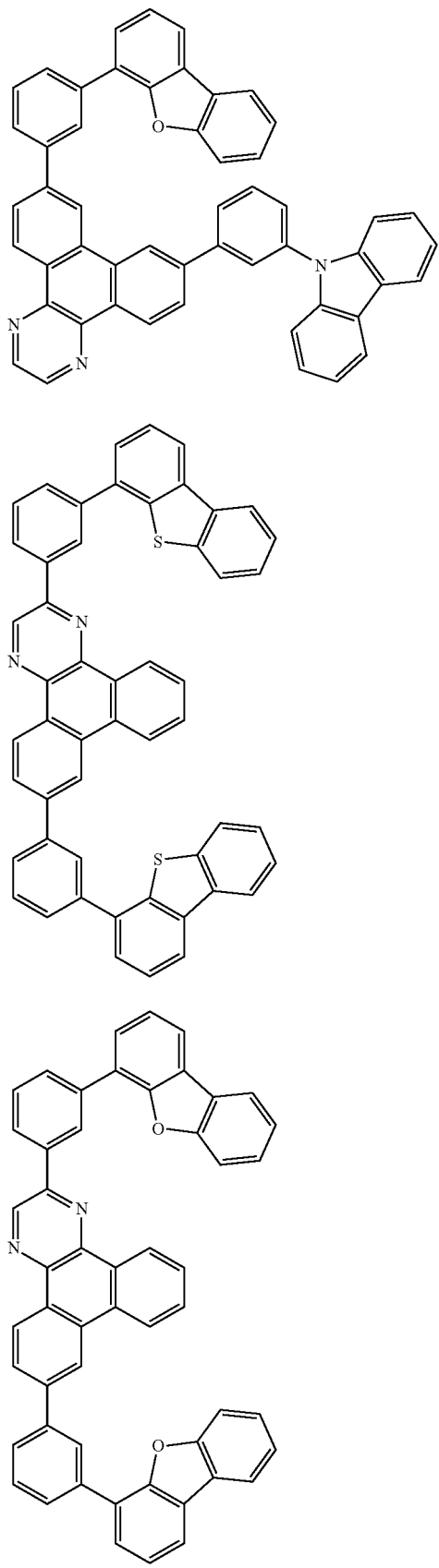

(152)

(153)

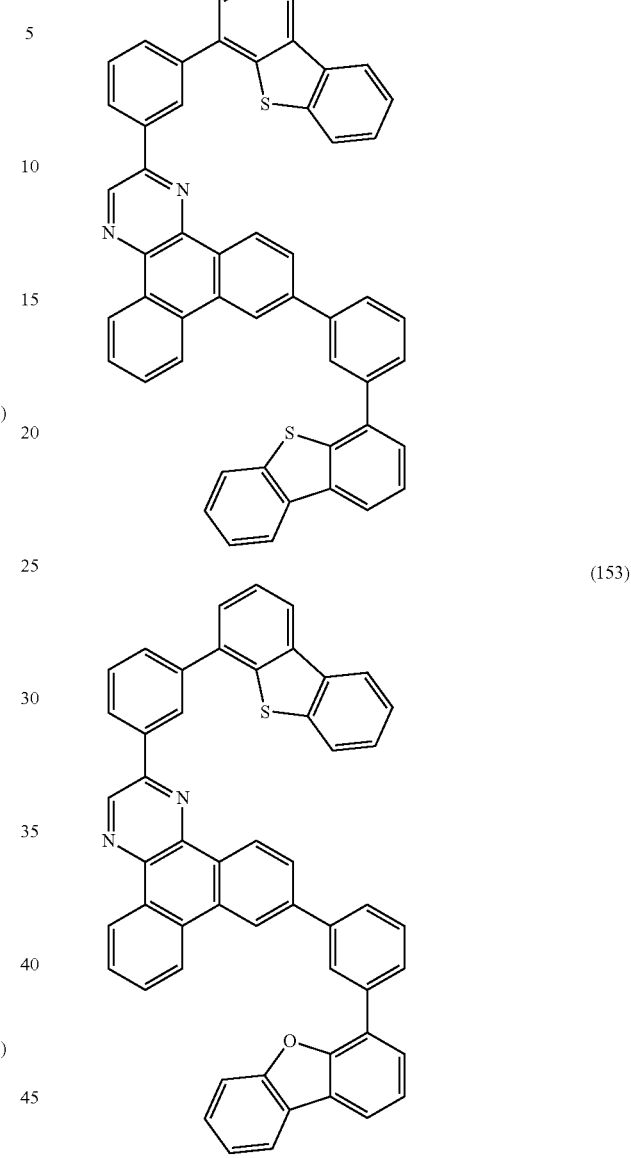

A variety of reactions can be applied as a method of synthesizing any of the heterocyclic compounds according to one embodiment of the present invention. For example, synthesis reactions described below enable the synthesis of the heterocyclic compound according to one embodiment of the present invention represented by the general formula (G1). Note that the methods of synthesizing the heterocyclic compound according to one embodiment of the present invention are not limited to the synthesis methods below.

(Method 1 of Synthesizing Heterocyclic Compound Represented by General Formula (G1))

As illustrated in the following synthesis scheme (A-1), a halogenated dibenzoquinoxaline compound (a1) is reacted with an aryl boron compound (a2) and an aryl boron compound (a3), so that the heterocyclic compound represented by the general formula (G1) can be synthesized. The synthesis scheme (A-1) is shown below.

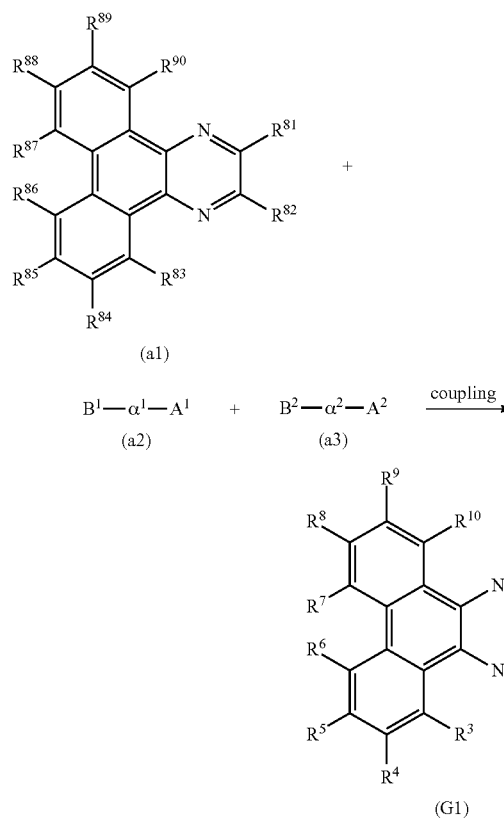

In the synthesis scheme (A-1), α¹ and α² separately represent a substituted or unsubstituted phenylene group or a substituted or unsubstituted biphenyldiyl group, and A¹ and A² separately represent a substituted or unsubstituted carbazolyl group, a substituted or unsubstituted dibenzothiophenyl group, or a substituted or unsubstituted dibenzofuranyl group. B¹ and B² separately represent a boronic acid or dialkoxyborane.

In the synthesis scheme (A-1), any one of $R^{81}$ to $R^{90}$ represents a substituent represented by the following general formula (a1-1), another one of $R^{81}$ to $R^{90}$ represents a substituent represented by the following general formula (a1-2), and the others separately represent hydrogen, an alkyl group having 1 to 6 carbon atoms, a substituted or unsubstituted phenyl group, or a substituted or unsubstituted biphenyl group.

In the synthesis scheme (A-1), any one of $R^1$ to $R^{10}$ represents a substituent represented by the following general formula (G1-1), another one of $R^1$ to $R^{10}$ represents a substituent represented by the following general formula (G1-2), and the others separately represent hydrogen, an alkyl group having 1 to 6 carbon atoms, a substituted or unsubstituted phenyl group, or a substituted or unsubstituted biphenyl group.

—X¹            (a1-1)

—X²            (a1-2)

—α¹—A¹            (G1-1)

—α²—A²            (G1-2)

$X^1$ in the general formula (a1-1) and $X^2$ in the general formula (a1-2) separately represent chlorine, bromine, or iodine. $X^1$ and $X^2$ preferably represent bromine or iodine, which has high reactivity, more preferably iodine. Further, α¹ in the general formula (G1-1) and α² in the general formula (G1-2) separately represent a substituted or unsubstituted phenylene group or a substituted or unsubstituted biphenyldiyl group, and A¹ in the general formula (G1-1) and A² in the general formula (G1-2) separately represent a substituted or unsubstituted carbazolyl group, a substituted or unsubstituted dibenzothiophenyl group, or a substituted or unsubstituted dibenzofuranyl group.

In the synthesis scheme (A-1), α¹ is bonded to a position where $X^1$ has been bonded, and α² is bonded to a position where $X^2$ has been bonded.

Note that a variety of reaction conditions can be employed for the coupling reaction in the synthesis scheme (A-1). As an example thereof, a synthesis method using a metal catalyst in the presence of a base can be employed.

The case where a Suzuki-Miyaura reaction is used in the synthesis scheme (A-1) is described.

A palladium catalyst can be used as the metal catalyst, and a mixture of a palladium complex and a ligand thereof can be used as the palladium catalyst. As examples of the palladium complex, palladium(II) acetate, tetrakis(triphenylphosphine)palladium(0), bis(triphenylphosphine)palladium(II)dichloride, and the like are given. As examples of the ligand, tri(ortho-tolyl)phosphine, triphenylphosphine, tricyclohexylphosphine, and the like are given.

Examples of a substance which can be used for the base include organic bases such as sodium tert-butoxide and inorganic bases such as sodium carbonate and potassium carbonate.

The reaction is preferably performed in a solution. Examples of a solvent which can be used include a mixed solvent of acetonitrile and water; a mixed solvent of an aromatic hydrocarbon solvent such as toluene or xylene and water; a ternary mixed solvent of toluene or xylene, an alcohol such as ethanol, and water; a mixed solvent of an organic polar solvent such as 1,3-dimethyl-3,4,5,6-tetrahydro-2(1H)-pyrimidinone (DMPU) and water; a mixed solvent of an ether such as ethylene glycol dimethyl ether and water; and the like.

Note that the catalyst, ligand, base, and solvent which can be used are not limited to the above.

In the synthesis scheme (A-1), instead of the aryl boron compound (a2), an aryl aluminum, an aryl zirconium, an aryl zinc, an aryl tin, or the like may be used. In addition, the reaction is preferably performed under an inert atmosphere of nitrogen, argon, or the like. Further, heating may be performed with electromagnetic waves.

In particular, the synthesis method represented by the above synthesis scheme (A-1) is preferred when α¹ and α² are the same and A¹ and A² are the same, because the heterocyclic compound represented by the general formula (G1) can be synthesized with high purity and high yield. In other words, this synthesis method is convenient when α¹ and α² are the same and A¹ and A² are the same, because 2 equivalents of one of the compound (a2) and the compound (a3) can be reacted with the compound (a1).

In the above halogenated dibenzoquinoxaline compound (a1), $X^1$ and $X^2$ are preferably positioned at the 6- and 11-positions or the 7- and 10-positions of the dibenzo[f,h]quinoxaline ring, because a halide having bonds at these positions can be easily synthesized.

Thus, the heterocyclic compound of this embodiment can be synthesized.

(Method 2 of Synthesizing Heterocyclic Compound Represented by General Formula (G1))

Another method of synthesizing the heterocyclic compound represented by the general formula (G1) is described below. As illustrated in the following synthesis scheme (B-1), a halogenated dibenzoquinoxaline compound (a4) and 2 equivalents of the aryl boron compound (a2) are coupled, so that the heterocyclic compound represented by the general formula (G1) can be synthesized. The synthesis scheme (B-1) is shown below.

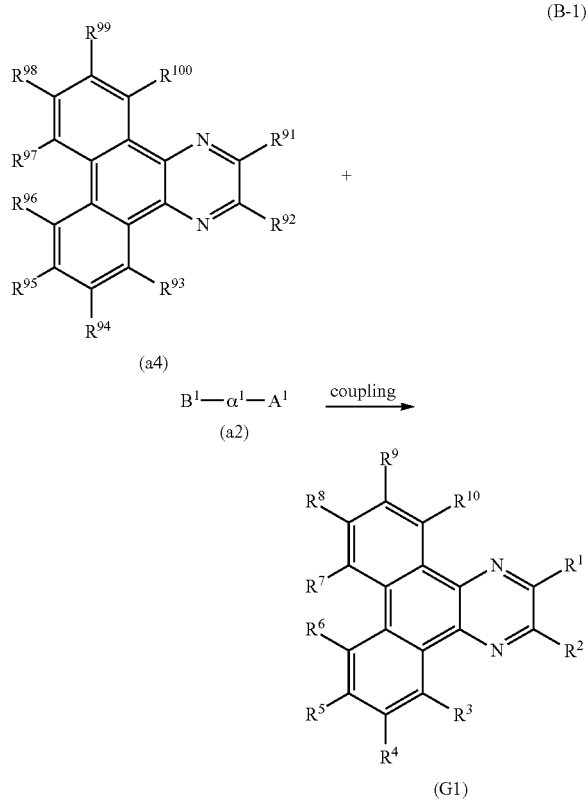

In the synthesis scheme (B-1), $\alpha^1$ represents a substituted or unsubstituted phenylene group or a substituted or unsubstituted biphenyldiyl group, and $A^1$ represents a substituted or unsubstituted carbazolyl group, a substituted or unsubstituted dibenzothiophenyl group, or a substituted or unsubstituted dibenzofuranyl group. $B^1$ represents a boronic acid or dialkoxyborane.

In the synthesis scheme (B-1), any one of $R^{91}$ to $R^{100}$ represents a substituent represented by the following general formula (a4-1), another one of $R^{91}$ to $R^{100}$ represents a substituent represented by the following general formula (a4-2), and the others separately represent hydrogen, an alkyl group having 1 to 6 carbon atoms, a substituted or unsubstituted phenyl group, or a substituted or unsubstituted biphenyl group.

In the synthesis scheme (B-1), any one of $R^1$ to $R^{10}$ represents a substituent represented by the following general formula (G1-1), another one of $R^1$ to $R^{10}$ represents a substituent represented by the following general formula (G1-2), and the others separately represent hydrogen, an alkyl group having 1 to 6 carbon atoms, a substituted or unsubstituted phenyl group, or a substituted or unsubstituted biphenyl group.

In the general formula (a4-1), $X^1$ represents chlorine, bromine, or iodine. $X^1$ preferably represents bromine or iodine, which has high reactivity, more preferably iodine. In the general formula (G1-1), $\alpha^1$ represents a substituted or unsubstituted phenylene group or a substituted or unsubstituted biphenyldiyl group, and $A^1$ represents a substituted or unsubstituted carbazolyl group, a substituted or unsubstituted dibenzothiophenyl group, or a substituted or unsubstituted dibenzofuranyl group. In the general formulae (a4-2) and (G1-2), $\alpha^2$ represents a substituted or unsubstituted phenylene group or a substituted or unsubstituted biphenyldiyl group, and $A^2$ represents a substituted or unsubstituted carbazolyl group, a substituted or unsubstituted dibenzothiophenyl group, or a substituted or unsubstituted dibenzofuranyl group.

In the synthesis scheme (B-1), $\alpha^1$ is bonded to a position where $X^1$ has been bonded.

A variety of reaction conditions can be employed for the coupling reaction in the synthesis scheme (B-1). As an example thereof, a synthesis method using a metal catalyst in the presence of a base can be employed.

In the synthesis scheme (B-1), a Suzuki-Miyaura reaction can be employed. Details are omitted because the above synthesis scheme (A-1) can be referred to.

As described above, the synthesis method represented by the scheme (B-1), which allows stepwise introduction of the substituents to the dibenzo[f,h]quinoxaline ring, is preferred when $\alpha^1$ and $\alpha^2$ are different and/or $A^1$ and $A^2$ are different, because the compound according to one embodiment of the present invention can be synthesized with high purity and high yield.

Thus, the heterocyclic compound of this embodiment can be synthesized.

Since the heterocyclic compound of this embodiment has a wide band gap, high emission efficiency can be obtained by using the heterocyclic compound in a light-emitting layer of a light-emitting element as a host material in which a light-emitting substance is dispersed. In particular, the heterocyclic compound of this embodiment is suitably used as a host material in which a phosphorescent compound is dispersed. Further, owing to a high electron-transport property, the heterocyclic compound of this embodiment can be suitably used as a material of an electron-transport layer in a light-emitting element. By the use of the heterocyclic compound of this embodiment, a light-emitting element having low driving voltage, a light-emitting element having high emission efficiency, or a light-emitting element having a long lifetime can be achieved. Furthermore, by use of this light-emitting element, a light-emitting device, an electronic device, and a lighting device each having reduced power consumption can be obtained.

Further, the heterocyclic compound of this embodiment can be used for an organic thin-film solar cell. Specifically, the heterocyclic compound according to one embodiment of the present invention can be used for a carrier-transport layer or a carrier-injection layer owing to its carrier-transport property. Furthermore, the heterocyclic compound according to one embodiment of the present invention can be photoexcited and hence can be used for a power generation layer.

(Embodiment 2)

In this embodiment, as one embodiment of the present invention, a light-emitting element in which any of the heterocyclic compounds described in Embodiment 1 is used is described with reference to FIGS. 1A and 1B. This embodiment shows a light-emitting element in which the heterocyclic compound is used for a light-emitting layer.

In the light-emitting element of this embodiment, an EL layer having at least a light-emitting layer is interposed between a pair of electrodes. The EL layer may also have a plurality of layers in addition to the light-emitting layer. The plurality of layers is a combination of layers containing a substance with a high carrier-injection property and a substance with a high carrier-transport property, which are stacked so that a light-emitting region is formed in a region away from the electrodes, that is, so that the carriers are recombined in an area away from the electrodes. In this specification, the layer containing a substance with a high carrier-injection property or a substance with a high carrier-transport property is also called functional layer which functions, for instance, to inject or transport carriers. As the functional layer, a hole-injection layer, a hole-transport layer, an electron-injection layer, an electron-transport layer, or the like can be used.

In the light-emitting element of this embodiment illustrated in FIG. 1A, an EL layer 102 having a light-emitting layer 113 is provided between a pair of electrodes, a first electrode 101 and a second electrode 103. The EL layer 102 includes a hole-injection layer 111, a hole-transport layer 112, the light-emitting layer 113, an electron-transport layer 114, and an electron-injection layer 115. The light-emitting element in FIG. 1A includes the first electrode 101 formed over a substrate 100; the hole-injection layer 111, the hole-transport layer 112, the light-emitting layer 113, the electron-transport layer 114, and the electron-injection layer 115 which are stacked over the first electrode 101 in this order; and the second electrode 103 provided over the electron-injection layer 115. Note that, in the light-emitting element described in this embodiment, the first electrode 101 functions as an anode and the second electrode 103 functions as a cathode.

The substrate 100 is used as a support of the light-emitting element. For example, glass, quartz, plastic, or the like can be used for the substrate 100. Furthermore, a flexible substrate may be used. The flexible substrate is a substrate that can be bent (is flexible), such as a plastic substrate made of polycarbonate, polyarylate, or poly(ether sulfone). Alternatively, a film (made of polypropylene, a polyester, poly(vinyl fluoride), poly(vinyl chloride), or the like), an inorganic film formed by evaporation, or the like can be used. Note that materials other than the above materials can be used as long as they can function as a support of a light-emitting element.

For the first electrode 101, a metal, an alloy, an electrically conductive compound, a mixture thereof, or the like which has a high work function (specifically, a work function of 4.0 eV or more) is preferably used. Specific examples are indium oxide-tin oxide (ITO: indium tin oxide), indium oxide-tin oxide containing silicon or silicon oxide, indium oxide-zinc oxide (indium zinc oxide), indium oxide containing tungsten oxide and zinc oxide (IWZO), and the like. Films of these conductive metal oxides are usually formed by sputtering; however, a sol-gel method or the like may also be used. For example, a film of indium oxide-zinc oxide can be formed by a sputtering method using a target in which zinc oxide is added to indium oxide at 1 wt % to 20 wt %. A film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Further, gold, platinum, nickel, tungsten, chromium, molybdenum, iron, cobalt, copper, palladium, nitrides of metal materials (e.g., titanium nitride), and the like can be used.

Note that, in the EL layer 102, when a layer in contact with the first electrode 101 is formed using a composite material of an organic compound and an electron acceptor (acceptor) described later, the first electrode 101 can be formed using any of a variety of metals, alloys, and electrically conductive compounds, a mixture thereof, and the like regardless of the work function. For example, aluminum, silver, an alloy containing aluminum (e.g., Al—Si), or the like can be used.

The EL layer 102 formed over the first electrode 101 includes at least the light-emitting layer 113, and part of the EL layer 102 is formed using the heterocyclic compound which is one embodiment of the present invention. For the part of the EL layer 102, a known substance can be used, and either a compound with a low molecular weight or a polymeric compound can be used. Note that the EL layer 102 may have not only a structure formed of only an organic compound but also a structure in which an inorganic compound is partially contained.

Figure 1B:
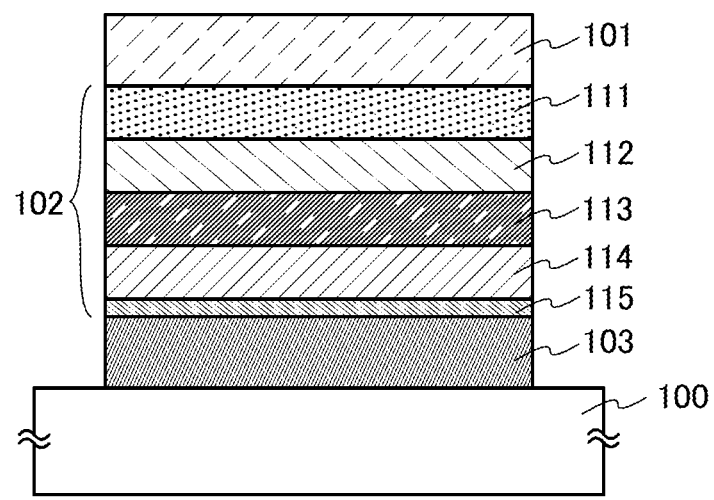

As illustrated in FIGS. 1A and 1B, the EL layer 102 is formed by stacking as appropriate the hole-injection layer 111, the hole-transport layer 112, the electron-transport layer 114, the electron-injection layer 115, and the like in combination, in addition to the light-emitting layer 113.

The hole-injection layer 111 is a layer containing a substance with a high hole-injection property. As the substance with a high hole-injection property, for example, metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide can be used. A phthalocyanine-based compound such as phthalocyanine (abbreviation: $H_2Pc$), or copper(II) phthalocyanine (abbreviation: CuPc) can also be used.

Alternatively, any of the following aromatic amine compounds which are organic compounds with a low molecular weight can be used: 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis [N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Further alternatively, any of polymers (including oligomers and dendrimers) can be used. For example, a polymer such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation:

PTPDMA), or poly[N,N'-bis(4-butylphenyl)-N,N'-bis(phenyl)benzidine (abbreviation: poly-TPD) can be used. Further, a polymer to which acid is added, such as poly(3,4-ethylenedioxythiophene)/poly(styrenesulfonic acid) (PEDOT/PSS) or polyaniline/poly(styrenesulfonic acid) (PAni/PSS), can be used.

A composite material in which an organic compound and an electron acceptor (acceptor) are mixed may be used for the hole-injection layer 111. Such a composite material has an excellent hole-injection and hole-transport properties because holes are generated in the organic compound by the electron acceptor.

As the organic compound for the composite material, various compounds such as an aromatic amine compound, a carbazole derivative, an aromatic hydrocarbon, and a polymer (including oligomer and dendrimer) can be used. The organic compound used for the composite material is preferably an organic compound with a high hole-transport property. Specifically, a substance having a hole mobility of $10^{-6}$ cm$^2$/V·s or higher is preferably used. However, substances other than the above substances may be used as long as they are substances with a hole-transport property higher than an electron-transport property. The organic compounds which can be used for the composite material are specifically shown below.

Examples of the organic compounds that can be used for the composite material include aromatic amine compounds such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), and N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BPAFLP); and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl]-2,3,5,6-tetraphenylbenzene.

Alternatively, it is possible to use an aromatic hydrocarbon compound such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, or 2,3,6,7-tetramethyl-9,10-di(1-naphthyl)anthracene.

Further alternatively, it is possible to use an aromatic hydrocarbon compound such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), or 9,10-bis[4-(2,2-diphenylvinyl)phenyl]anthracene (abbreviation: DPVPA).

As the electron acceptor, organic compounds such as 7,7,8,8-tetracyano-2,3,5,6-tetrafluoroquinodimethane (abbreviation: F$_4$-TCNQ) and chloranil; and transition metal oxides can be used. For example, oxides of metals belonging to Groups 4 to 8 in the periodic table can be used. Specifically, vanadium oxide, niobium oxide, tantalum oxide, chromium oxide, molybdenum oxide, tungsten oxide, manganese oxide, and rhenium oxide are preferable because their electron-accepting property is high. Among these, molybdenum oxide is especially preferable because it is stable in the air, has a low hygroscopic property, and is easily treated.

Note that the hole-injection layer 111 may be formed using a composite material of the above-described polymer, such as PVK, PVTPA, PTPDMA, or Poly-TPD, and the above-described electron acceptor.

The hole-transport layer 112 is a layer that contains a substance with a high hole-transport property. Examples of the substance with a high hole-transport property include a substance having a carbazole skeleton, a substance having a triarylamine skeleton, a substance having a dibenzothiophene skeleton, and a substance having a dibenzofuran skeleton. Specifically, for example, it is possible to use an aromatic amine compound such as NPB, TPD, BPAFLP, 4,4'-bis[N-(9,9-dimethylfluoren-2-yl)-N-phenylamino]biphenyl (abbreviation: DFLDPBi), or 4,4'-bis[N-(spiro-9,9'-bifluoren-2-yl)-N-phenylamino]biphenyl (abbreviation: BSPB). The substances mentioned here are mainly ones that have a hole mobility of $10^{-6}$ cm$^2$/V·s or higher. However, substances other than the above substances may be used as long as they are substances with a hole-transport property higher than an electron-transport property. The layer containing a substance with a high hole-transport property is not limited to a single layer, and two or more layers containing the above substances may be stacked.

For the hole-transport layer 112, a carbazole derivative such as CBP, CzPA, or PCzPA or an anthracene derivative such as t-BuDNA, DNA, or DPAnth may also be used.

For the hole-transport layer 112, a polymer such as PVK, PVTPA, PTPDMA, or Poly-TPD can also be used.

The light-emitting layer 113 is a layer that contains a light-emitting substance. In this embodiment, the light-emitting layer contains the heterocyclic compound described in Embodiment 1.

The heterocyclic compound of one embodiment of the present invention is a light-emitting organic compound, and thus can be used as the light-emitting substance.

In the light-emitting layer in which a light-emitting substance (guest material) is dispersed in another substance (host material), the heterocyclic compound can be used as the host material. The guest material which is a light-emitting substance is dispersed in the heterocyclic compound, so that light emission from the guest material can be obtained. In this manner, the heterocyclic compound according to one embodiment of the present invention is effectively used as the host material in the light-emitting layer.

In addition, plural types of substances (host materials) can be used as substances in which the light-emitting substance (guest material) is dispersed.

The light-emitting layer may contain a different material in addition to the heterocyclic compound according to one embodiment of the present invention and the guest material.

As the light-emitting substance, for example, a fluorescent compound which emits fluorescence or a phosphorescent compound which emits phosphorescence can be used. Examples of the fluorescent compound that can be used for the light-emitting layer 113 include the following. Examples of a material that emits blue light include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA), and the like.

Examples of a material that emits green light include N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. Examples of a material that emits yellow light include rubrene, 5,12-bis(1,1'-biphenyl-4-yl)-6,11-diphenyltetracene (abbreviation: BPT), and the like. Examples of a material that emits red light include N,N,N',N'-tetrakis(4-methylphenyl)tetracene-5,11-diamine (abbreviation: p-mPhTD), 7,14-diphenyl-N,N,N',N'-tetrakis (4-methylphenyl)acenaphtho[1,2-α]fluoranthene-3,10-diamine (abbreviation: p-mPhAFD), and the like.

Examples of the phosphorescent compound that can be used for the light-emitting layer 113 include the following. Examples of a material that emits green light include tris(2-phenylpyridinato-N, $C^{2'}$)iridium(III) (abbreviation: [Ir(ppy)$_3$]), bis(2-phenylpyridinato-N, $C^{2'}$)iridium(III)acetylacetonate (abbreviation: [Ir(ppy)$_2$(acac)]), bis(1,2-diphenyl-1H-benzimidazolato)iridium(III)acetylacetonate (abbreviation: [Ir(pbi)$_2$(acac)]), bis(benzo[h]quinolinato)iridium(III)acetylacetonate (abbreviation: [Ir(bzq)$_2$(acac)]), tris(benzo[h]quinolinato)iridium(III) (abbreviation: [Ir(bzq)$_3$]), and the like. Examples of a material that emits yellow light include bis(2,4-diphenyl-1,3-oxazolato-N,$C^{2'}$)iridium(III)acetylacetonate (abbreviation: [Ir(dpo)$_2$(acac)]), bis[2-(4'-(perfluorophenylphenyl)pyridinato]iridium(III)acetylacetonate (abbreviation: [Ir(p-PF-ph)$_2$(acac)]), bis(2-phenylbenzothiazolato-N, $C^{2'}$)iridium(III)acetylacetonate (abbreviation: [Ir(bt)$_2$(acac)]), (acetylacetonato)bis[2,3-bis(4-fluorophenyl)-5-methylpyrazinato]iridium(III) (abbreviation: [Ir(Fdppr-Me)$_2$(acac)]), (acetylacetonato)bis[2-(4-methoxyphenyl)-3,5-dimethylpyrazinato]iridium(III) (abbreviation: [Ir(dmmoppr)$_2$(acac)]), and the like. Examples of a material that emits orange light include tris(2-phenylquinolinato-N, $C^{2'}$)iridium(III) (abbreviation: [Ir(pq)$_3$]), bis(2-phenylquinolinato-N,$C^{2'}$)iridium(III)acetylacetonate (abbreviation: [Ir(pq)$_2$(acac)]), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), and the like. Examples of a material that emits red light include organometallic complexes such as bis[2-(2'-benzo[4,5-a]thienyl)pyridinato-N,$C^{3'}$)iridium(III) acetylacetonate (abbreviation: [Ir(btp)$_2$(acac)]), bis(1-phenylisoquinolinato-N,$C^{2'}$)iridium(III)acetylacetonate (abbreviation: [Ir(piq)$_2$(acac)]), (acetylacetonato)bis[2,3-bis(4-fluorophenyl)quinoxalinato]iridium(III) (abbreviation: [Ir(Fdpq)$_2$(acac)]), (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and 2,3,7,8,12,13,17,18-octaethyl-21H,23H-porphyrin platinum(II) (abbreviation: PtOEP). In addition, a rare earth metal complex such as tris(acetylacetonato)(monophenanthroline)terbium(III) (abbreviation: [Tb(acac)$_3$(Phen)]), tris(1,3-diphenyl-1,3-propanedionato)(monophenanthroline)europium(III) (abbreviation: [Eu(DBM)$_3$(Phen)]), or tris[1-(2-thenoyl)-3,3,3-trifluoroacetonato](monophenanthroline)europium(III) (abbreviation: [Eu(TTA)$_3$(Phen)]) exhibits light emission from a rare earth metal ion (electron transition between different multiplicities); therefore, such a rare earth metal complex can be used as a phosphorescent compound.

Note that the dibenzo[f,h]quinoxaline skeleton is considered to predominantly determine the LUMO level of the heterocyclic compound according to one embodiment of the present invention. Further, as described below, the compound has a deep LUMO level of at least −2.8 eV or less, specifically −2.9 eV or less, on the basis of cyclic voltammetry (CV) measurements. For example, according to Example 1, the LUMO level of 6,11mDBTPDBq-II based on CV measurements is −2.90 eV. Further, the LUMO level of the above-described phosphorescent compound having a pyrazine skeleton, such as [Ir(mppr-Me)$_2$(acac)], [Ir(mppr-iPr)$_2$(acac)], [Ir(tppr)$_2$(acac)], or [Ir(tppr)$_2$(dpm)], is substantially equally deep. Accordingly, in a light-emitting layer where the heterocyclic compound according to one embodiment of the present invention is used as the host material and the phosphorescent compound having a pyrazine skeleton is used as the guest material, electron traps in the light-emitting layer can be reduced as much as possible, so that the light-emitting element can be driven at an extremely low voltage.

Note that the host material preferably has a deeper HOMO level and a shallower LUMO level than the guest material (light-emitting substance). Such a structure allows carriers injected to the host material to be efficiently transferred to the guest material. The heterocyclic compound according to one embodiment of the present invention has a relatively deep HOMO level (the value thereof is relatively small), and thus is preferable as the host material. Hence, the HOMO level of the guest material is preferably higher than or equal to −6.0 eV and lower than or equal to −5.0 eV. Note that the LUMO level of the guest material is preferably higher than or equal to −3.5 eV and lower than or equal to −2.5 eV.

As the light-emitting substance, a polymer can also be used. Specifically, as a material that emits blue light, poly(9,9-dioctylfluorene-2,7-diyl)(abbreviation: PFO), poly[(9,9-dioctylfluorene-2,7-diyl)-co-(2,5-dimethoxybenzene-1,4-diyl)] (abbreviation: PF-DMOP), poly{(9,9-dioctylfluorene-2,7-diyl)-co-[N,N'-di-(p-butylphenyl)-1,4-diaminobenzene]} (abbreviation: TAB-PFH), or the like can be used. As a material that emits green light, poly(p-phenylenevinylene) (abbreviation: PPV), poly[(9,9-dihexylfluorene-2,7-diyl)-alt-co-(benzo[2,1,3]thiadiazole-4,7-diyl)] (abbreviation: PFBT), poly[(9,9-dioctyl-2,7-divinyleneifluorenylene)-alt-co-(2-methoxy-5-(2-ethylhexyloxy)-1,4-phenylene)], or the like can be used. As a material that emits orange to red light, poly[2-methoxy-5-(2'-ethylhexyloxy)-1,4-phenylenevinylene] (abbreviation: MEH-PPV), poly(3-butylthiophene-2,5-diyl) (abbreviation: R4-PAT), poly{[9,9-dihexyl-2,7-bis(1-cyanovinylene)fluorenylene]-alt-co-[2,5-bis(N,N'-diphenylamino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD), or the like can be used.

The following shows another embodiment of the light-emitting layer 113 described in this embodiment. The light-emitting layer 113 can contain a phosphorescent compound, a first organic compound, and a second organic compound. The phosphorescent compound is the guest material (light-emitting substance) in the light-emitting layer 113. One of the first organic compound and the second organic compound, the content of which is higher than that of the other in the light-emitting layer 113, is the host material in the light-emitting layer 113. The heterocyclic compound according to one embodiment of the present invention can be used as the first organic compound or the second organic compound.

By dispersing the guest material in the host material in the light-emitting layer 113, it is possible to suppress concentration quenching of the guest material, and thus the light-emitting element can have higher emission efficiency.

It is preferable that the T1 level of each of the first and second organic compounds be higher than that of the phosphorescent compound. This is because, when the T1 level of the first organic compound (or the second organic compound) is lower than that of the phosphorescent compound, the triplet excitation energy of the phosphorescent compound, which is to contribute to light emission, is quenched by the first organic compound (or the second organic compound) and accordingly the emission efficiency is decreased.

As the phosphorescent compound, a phosphorescent organometallic iridium complex or the like can be used. As the first and second organic compounds, a compound which easily accepts electrons (electron-transport compound) and a compound which easily accepts holes (hole-transport compound) are preferably combined.

The heterocyclic compound according to one embodiment of the present invention can be used as an electron-transport compound.

As a hole-transport compound, a compound with a higher hole-transport property than the heterocyclic compound according to one embodiment of the present invention, which is used as the electron-transport compound, is used. For example, it is possible to use any of the compounds given above as compounds that can be used for the hole-transport layer 112, such as a substance having a carbazole skeleton, a substance having a triarylamine skeleton, a substance having a dibenzothiophene skeleton, and a substance having a dibenzofuran skeleton. Note that a compound having a higher T1 level than a phosphorescent compound to be used is selected from these compounds. Further, the difference between the HOMO level of the hole-transport compound and the HOMO level of the phosphorescent compound is preferably within 0.2 eV in which case the phosphorescent compound does not strongly trap holes so that the light-emitting region expands. Specifically, for example, it is possible to use any of the following: 4-phenyl-4'-(9-phenyl-9H-carbazol-3-yl)triphenylamine (abbreviation: PCBA1BP), PCzPCN1,4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-N',N'-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), TPD, DPAB, N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), PCzPCA1, 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), DNTPD, 3,6-bis[N-(4-diphenylaminophenyl)-N-(1-naphthyl)amino]-9-phenylcarbazole (abbreviation: PCzTPN2), and PCzPCA2.

Note that in the case where a compound which easily accepts electrons and a compound which easily accepts holes are used as the first organic compound and the second organic compound, carrier balance can be controlled by the mixture ratio of the compounds. Specifically, the ratio of the first organic compound to the second organic compound is preferably 1:9 to 9:1.

The electron-transport layer 114 is a layer containing a substance with a high electron-transport property. For example, as the substance with a high electron-transport property, a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq), can be used. Alternatively, a metal complex or the like including an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances mentioned here are mainly ones that have an electron mobility of $10^{-6}$ cm$^2$/V·s or higher. Furthermore, the electron-transport layer is not limited to a single layer, and two or more layers made of the above substances may be stacked.

The electron-injection layer 115 is a layer containing a substance which has a high electron-injection property or promotes electron-injection from the cathode. For the electron-injection layer 115, an alkali metal, an alkaline earth metal, or a compound thereof, such as lithium, cesium, calcium, lithium fluoride, cesium fluoride, calcium fluoride, or lithium oxide, can be used. Alternatively, a rare earth metal compound such as erbium fluoride can be used. Further alternatively, the above substances for forming the electron-transport layer 114 can be used.

Further alternatively, a composite material in which an organic compound and an electron donor (donor) are mixed may be used for the electron-injection layer 115. Such a composite material has an excellent electron-injection and electron-transport properties because electrons are generated in the organic compound by the electron donor. In this case, the organic compound is preferably a material excellent in transporting the generated electrons. Specifically, the above substances for forming the electron-transport layer 114 (e.g., a metal complex or a heteroaromatic compound) can be used, for example. As the electron donor, a substance exhibiting an electron-donating property to the organic compound may be used. Specifically, it is preferable to use an alkali metal, an alkaline earth metal, or a rare earth metal, such as lithium, cesium, magnesium, calcium, erbium, or ytterbium. Further, an alkali metal oxide or an alkaline earth metal oxide is preferable, such as lithium oxide, calcium oxide, or barium oxide. Alternatively, Lewis base such as magnesium oxide can be used. Further alternatively, an organic compound such as tetrathiafulvalene (abbreviation: TTF) can be used.

Note that each of the above-described hole-injection layer 111, hole-transport layer 112, light-emitting layer 113, electron-transport layer c114, and electron-injection layer 115 can be formed by a method such as an evaporation method (e.g., a vacuum evaporation method), an inkjet method, or a coating method.

When the second electrode 103 functions as a cathode, it is preferably formed using a metal, an alloy, an electrically conductive compound, a mixture thereof, or the like having a low work function (preferably, a work function of 3.8 eV or less). Specifically, any of the following can be used: aluminum or silver; an element belonging to Group 1 or 2 of the periodic table, that is, an alkali metal such as lithium or cesium or an alkaline earth metal such as calcium or strontium; magnesium (Mg); an alloy thereof (e.g., Mg—Ag or Al—Li); a rare earth metal such as europium or ytterbium; an alloy thereof; and the like.

However, when a layer which is in contact with the second electrode 103 and included in the EL layer 102 is formed using a composite material containing an organic compound and an electron donor (donor) described above, a variety of conductive materials such as aluminum, silver, ITO, and indium oxide-tin oxide containing silicon or silicon oxide can be used regardless of work function.

Note that the second electrode 103 can be formed by a vacuum evaporation method or a sputtering method. Alternatively, in the case of using a silver paste or the like, a coating method, an inkjet method, or the like can be used.

In the above-described light-emitting element, current flows due to a potential difference applied between the first electrode 101 and the second electrode 103, and holes and electrons recombine in the EL layer 102, whereby light is emitted. Then, this emitted light is extracted out through one or both of the first electrode 101 and the second electrode 103. Therefore, one or both of the first electrode 101 and the second electrode 103 is/are an electrode with a property of transmitting visible light.

Further, the structure of a layer provided between the first electrode 101 and the second electrode 103 is not limited to the above-described structure. A structure other than the above may alternatively be employed as long as a light-emitting region in which holes and electrons recombine is provided in a portion away from the first electrode 101 and the second electrode 103 in order to prevent quenching due to proximity of the light-emitting region to a metal.

In other words, the stacked structure of the layers may be freely formed by, without particular limitation, combining a layer containing a substance with a high electron-transport property, a substance with a high hole-transport property, a substance with a high electron-injection property, a substance with a high hole-injection property, a bipolar substance (substance with a high electron-transport property and a high hole-transport property), a hole-blocking material, or the like and a light-emitting layer containing the heterocyclic compound according to one embodiment of the present invention as a host material.

The heterocyclic compound according to one embodiment of the present invention is a substance with a high electron-transport property, and thus can be used for the electron-transport layer.

By use of the heterocyclic compound according to one embodiment of the present invention for both the light-emitting layer (particularly as the host material in the light-emitting layer) and the electron-transport layer, materials having close LUMO levels are in contact with each other, so that electrons can be easily injected to the light-emitting layer from the electron-transport layer. Accordingly, the light-emitting element can be driven at an extremely low voltage.

In a light-emitting element illustrated in FIG. 1B, the EL layer 102 is provided between the pair of electrodes, the first electrode 101 and the second electrode 103, over the substrate 100. The EL layer 102 includes the hole-injection layer 111, the hole-transport layer 112, the light-emitting layer 113, the electron-transport layer 114, and the electron-injection layer 115. The light-emitting element in FIG. 1B includes the second electrode 103 functioning as a cathode over the substrate 100; the electron-injection layer 115, the electron-transport layer 114, the light-emitting layer 113, the hole-transport layer 112, and the hole-injection layer 111 which are stacked over the second electrode 103 in this order; and the first electrode 101 functioning as an anode over the hole-injection layer 111.

The following shows a specific formation method of the light emitting element.

The light-emitting element of Embodiment 2 has a structure in which the EL layer is interposed between the pair of electrodes. The EL layer has at least the light-emitting layer, and the light-emitting layer is formed using the heterocyclic compound according to one embodiment of the present invention as a host material. Further, the EL layer may include a functional layer (e.g., a hole-injection layer, a hole-transport layer, an electron-transport layer, or an electron-injection layer) in addition to the light-emitting layer. Each electrode (the first electrode or the second electrode), the light-emitting layer, and each functional layer may be formed by any of the wet processes such as a droplet discharging method (inkjet method), a spin coating method, or a printing method, or by a dry process such as a vacuum evaporation method, a CVD method, or a sputtering method. The use of a wet process enables the formation at atmospheric pressure using a simple device and process, thereby simplifying the process and improving the productivity. In contrast, in a dry process, dissolution of a material is not needed, and thus, a material that has low solubility in a solution can be used to expand the range of material choices.

All the thin films included in the light-emitting element may be formed by a wet method. In this case, the light-emitting element can be manufactured with only facilities needed for a wet process. Alternatively, formation of the stacked layers up to formation of the light-emitting layer may be performed by a wet process whereas the functional layer, the second electrode, and the like which are stacked over the light-emitting layer may be formed by a dry process. Further alternatively, the first electrode and the functional layer may be formed by a dry process before the formation of the light-emitting layer whereas the light-emitting layer, the functional layer stacked thereover, and the second electrode may be formed by a wet process. Needless to say, this embodiment is not limited to the aforementioned methods, and the light-emitting element can be formed by appropriate selection from a wet method and a dry method depending on a material to be used, necessary film thickness, and the interface state.

In this embodiment, the light-emitting element is formed over a substrate made of glass, plastic, or the like. A plurality of such light-emitting elements is formed over one substrate, thereby forming a passive matrix light-emitting device. In addition, for example, a thin film transistor (TFT) may be formed over a substrate formed of glass, plastic, or the like, and a light-emitting element may be manufactured over an electrode electrically connected to the TFT. In this manner, an active matrix light-emitting device in which the TFT controls the drive of the light-emitting element can be manufactured. Note that there is no particular limitation on the structure of the TFT. Either a staggered TFT or an inverted staggered TFT may be employed. In addition, there is no particular limitation on crystallinity of a semiconductor used for the TFT; an amorphous semiconductor or a crystalline semiconductor may be used. Furthermore, a driver circuit formed over a TFT substrate may be formed with both n-channel TFTs and p-channel TFTs or may be formed with either n-channel TFTs or p-channel TFTs.

Thus, a light-emitting element can be manufactured using the heterocyclic compound according to one embodiment of the present invention. By use of the heterocyclic compound according to one embodiment of the present invention for a light-emitting element, a light-emitting element that is driven at a low voltage can be obtained. Alternatively, a light-emitting element with high emission efficiency can be obtained. Further alternatively, a light-emitting element with a long lifetime can be obtained.

Furthermore, a light-emitting device (such as an image display device) using this light-emitting element according to one embodiment of the present invention, which is obtained as above, can have low power consumption.

Note that by use of the light-emitting element described in this embodiment, a passive matrix light-emitting device or an active matrix light-emitting device in which the drive of the light-emitting element is controlled by a thin film transistor (TFT) can be manufactured.

This embodiment can be implemented in appropriate combination with the other embodiments.

(Embodiment 3)

In Embodiment 3, a mode of a light-emitting element having a structure in which a plurality of light-emitting units is stacked (hereinafter, referred to as stacked-type element) is described with reference to FIGS. 2A and 2B. This light-emitting element includes the plurality of light-emitting units between a first electrode and a second electrode.

Figure 2A:
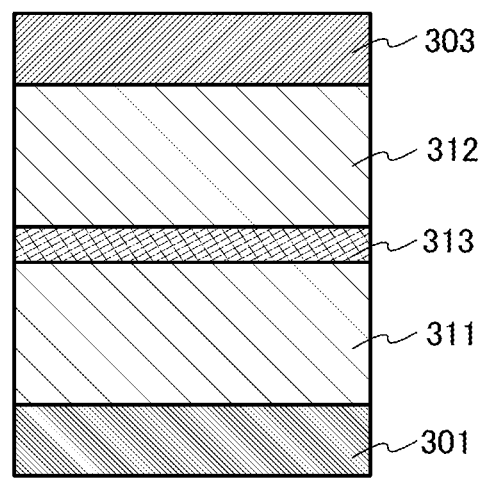
FIGS. 2A and 2B each illustrate a light-emitting element according to one embodiment of the present invention.

In FIG. 2A, a first light-emitting unit 311 and a second light-emitting unit 312 are stacked between a first electrode 301 and a second electrode 303. In this embodiment, the first electrode 301 functions as an anode and the second electrode 303 functions as a cathode. The first electrode 301 and the second electrode 303 can be the same as those in Embodiment 2. Further, the first light-emitting unit 311 and the second light-emitting unit 312 may have the same or different structures. The first light-emitting unit 311 and the second light-emitting unit 312 may be the same as those in Embodiment 2, or either of the units may be the same as that in Embodiment 2.

A charge generation layer 313 is provided between the first light-emitting unit 311 and the second light-emitting unit 312. The charge generation layer 313 functions so that electrons are injected into one light-emitting unit and holes are injected into the other light-emitting unit by application of voltage between the first electrode 301 and the second electrode 303. In this embodiment, when voltage is applied to the first electrode 301 so that the potential thereof is higher than that of the second electrode 303, the charge generation layer 313 injects electrons into the first light-emitting unit 311 and injects holes into the second light-emitting unit 312.

Note that the charge generation layer 313 preferably has the property of transmitting visible light in terms of light extraction efficiency. Further, the charge generation layer 313 functions even when it has lower conductivity than the first electrode 301 or the second electrode 303.

The charge generation layer 313 may have either a structure containing an organic compound with a high hole-transport property and an electron acceptor (acceptor) or a structure containing an organic compound with a high electron-transport property and an electron donor (donor). Alternatively, these structures may be stacked.

In the case of the structure in which an electron acceptor is added to an organic compound with a high hole-transport property, any of the following substances can be used as the organic compound with a high hole-transport property, for example: the heterocyclic compounds of embodiments of the present invention; aromatic amine compounds such as NPB, TPD, TDATA, MTDATA, and 4,4'-bis[N-(spiro-9,9'-bifluoren-2-yl)-N-phenylamino]biphenyl (abbreviation: BSPB); and the like. The substances mentioned here are mainly ones that have a hole mobility of $10^{-6}$ cm$^2$/V·s or higher. However, substances other than the above substances may be used as long as they are organic compounds with a hole-transport property higher than an electron-transport property.

Further, as the electron acceptor, 7,7,8,8-tetracyano-2,3,5,6-tetrafluoroquinodimethane (abbreviation: F$_4$-TCNQ), chloranil, and the like can be given. In addition, a transition metal oxide can be given. For example, an oxide of metals that belong to Groups 4 to 8 of the periodic table can be given. Specifically, vanadium oxide, niobium oxide, tantalum oxide, chromium oxide, molybdenum oxide, tungsten oxide, manganese oxide, and rhenium oxide are preferable because their electron-accepting property is high. Among these, molybdenum oxide is especially preferable because it is stable in the air, has a low hygroscopic property, and is easily treated.

In contrast, in the case of the structure in which an electron donor is added to an organic compound with a high electron-transport property, as the organic compound with a high electron-transport property, a metal complex having a quinoline skeleton or a benzoquinoline skeleton, such as Alq, Almq$_3$, BeBq$_2$, or BAlq, or the like can be used, for example. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, BPhen, BCP, or the like can be used. The substances mentioned here are mainly ones that have an electron mobility of $10^{-6}$ cm$^2$/V·s or higher. Note that substances other than the above substances may be used as long as they are organic compounds with an electron-transport property higher than a hole-transport property.

As the electron donor, an alkali metal, an alkaline earth metal, a rare earth metal, a metal belonging to Group 13 of the periodic table, or an oxide or carbonate thereof can be used. Specifically, lithium, cesium, magnesium, calcium, ytterbium, indium, lithium oxide, cesium carbonate, or the like is preferably used. Alternatively, an organic compound such as tetrathianaphthacene may be used as the electron donor.

Note that by formation of the charge generation layer 313 with the use of any of the above materials, it is possible to suppress the increase in drive voltage caused by the charge generation layer 313.

Figure 2B:
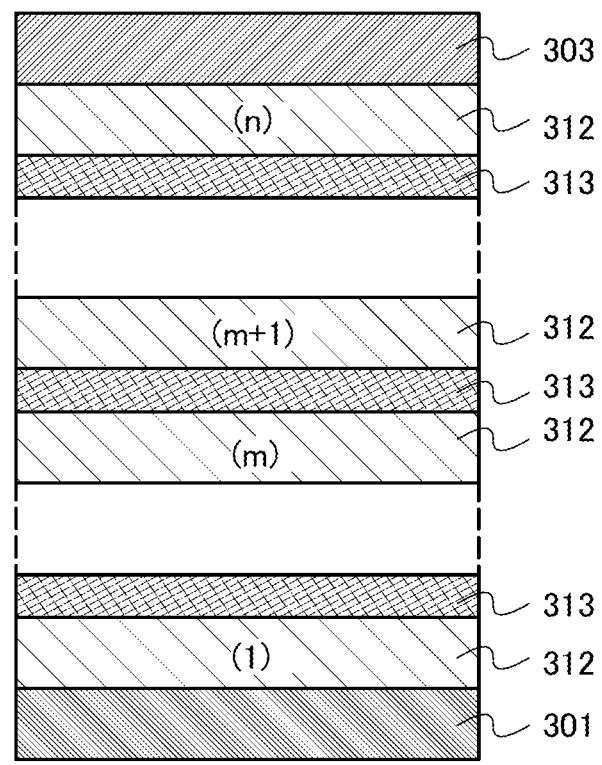

In this embodiment, the light-emitting element having two light-emitting units is described, and one embodiment of the present invention also includes a light-emitting element having a stack of three or more light-emitting units as illustrated in FIG. 2B. A plurality of light-emitting units which is partitioned by a charge generation layer is arranged between a pair of electrodes, as in the light-emitting element according to this embodiment, whereby it is possible to achieve an element which has a long lifetime and can emit light with a high luminance while current density is kept low.

The light-emitting units emit light having different colors from each other, thereby obtaining light emission of a desired color. For example, in a light-emitting element having two light-emitting units, the emission colors of the first light-emitting unit and the second light-emitting unit are made complementary, so that the light-emitting element which emits white light can be obtained. Note that the word "complementary" means color relationship in which an achromatic color is obtained when colors are mixed. That is, when complementarily colored light emitted from substances is mixed, white light emission can be obtained. Further, the same can be applied to a light-emitting element having three light-emitting units. For example, when a first light-emitting unit emits red light, a second light-emitting unit emits green light, and a third light-emitting unit emits blue light, white light can be obtained.

This embodiment can be implemented in appropriate combination with the other embodiments.

(Embodiment 4)

In Embodiment 4, a light-emitting device including a light-emitting element of one embodiment of the present invention is described with reference to FIGS. 3A and 3B. FIG. 3A is a top view illustrating the light-emitting device while FIG. 3B is a cross-sectional view taken along lines A-B and C-D of FIG. 3A.

The light-emitting device of this embodiment includes a source side driver circuit 401 and a gate side driver circuit 403 which are driver circuit portions, a pixel portion 402, a sealing substrate 404, a sealant 405, a flexible printed circuit (FPC) 409, and an element substrate 410. A portion enclosed by the sealant 405 is a space 407.

Note that a lead wiring 408 is a wiring for transmitting signals that are to be input to the source side driver circuit 401 and the gate side driver circuit 403, and receives a video signal, a clock signal, a start signal, a reset signal, and the like from the flexible printed circuit (FPC) 409 which serves as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

The driver circuit portion and the pixel portion are formed over the element substrate 410 illustrated in FIG. 3A. In FIG. 3B, the source side driver circuit 401 which is the driver circuit portion and one pixel in the pixel portion 402 are illustrated.

Note that as the source side driver circuit 401, a CMOS circuit which is obtained by combining an n-channel TFT 423 and a p-channel TFT 424 is formed. The driver circuit may be any of a variety of circuits formed with TFTs, such as a CMOS circuit, a PMOS circuit, or an NMOS circuit. Although this embodiment illustrates a driver-integrated type where the driver circuit is formed over the element substrate, the present invention is not limited to this structure, and the driver circuit may be formed outside the element substrate, not over the element substrate.

The pixel portion 402 includes a plurality of pixels having a switching TFT 411, a current control TFT 412, and a first electrode 413 electrically connected to a drain of the current control TFT 412. An insulator 414 is formed to cover an end portion of the first electrode 413. Here, the insulator 414 is formed using a positive type photosensitive resin film.

In order to improve the coverage, the insulator 414 is provided such that either an upper end portion or a lower end portion of the insulator 414 has a curved surface. For example, when a positive type photosensitive acrylic resin is used as a material for the insulator 414, the insulator 414 preferably has a curved surface with a curvature radius (0.2 µm to 3 µm) only at the upper end. The insulator 414 can be formed using either a negative photosensitive resin or a positive photosensitive resin.

A light-emitting layer 416 and a second electrode 417 are formed over the first electrode 413. Here, as a material for forming the first electrode 413 functioning as the anode, it is preferable to use a material having a high work function. For example, it is possible to use a single layer of an ITO film, an indium tin oxide film containing silicon, an indium oxide film containing 2 wt % to 20 wt % of zinc oxide, a titanium nitride film, a chromium film, a tungsten film, a Zn film, a Pt film, or the like, a stacked layer of a titanium nitride film and a film that mainly contains aluminum, a three-layer structure of a titanium nitride film, a film that mainly contains aluminum, and a titanium nitride film, or the like. Note that, when a stacked structure is employed, resistance of a wiring is low and a favorable ohmic contact is obtained.

In addition, the light-emitting layer 416 is formed by any of various methods such as an evaporation method using an evaporation mask, a droplet discharging method like an inkjet method, a printing method, and a spin coating method. The light-emitting layer 416 includes the heterocyclic compound described in Embodiment 1. Further, the light-emitting layer 416 may contain another material such as a material with a low molecular weight, an oligomer, a dendrimer, or a polymer.

As a material used for the second electrode 417 which is formed over the light-emitting layer 416 and functions as a cathode, it is preferable to use a material having a low work function (e.g., Al, Mg, Li, Ca, or an alloy or compound thereof such as Mg—Ag, Mg—In, or Al—Li). In order that light generated in the light-emitting layer 416 be transmitted through the second electrode 417, a stack of a thin metal film having a reduced thickness and a transparent conductive film (e.g., ITO, indium oxide containing 2 wt % to 20 wt % of zinc oxide, indium oxide-tin oxide containing silicon or silicon oxide, or zinc oxide) is preferably used for the second electrode 417.

The sealing substrate 404 is attached to the element substrate 410 with the sealant 405; thus, a light-emitting element 418 is provided in the space 407 enclosed by the element substrate 410, the sealing substrate 404, and the sealant 405. Note that the space 407 is filled with a filler such as an inert gas (e.g., nitrogen or argon) or the sealant 405.

Note that as the sealant 405, an epoxy-based resin is preferably used. A material used as the sealant 405 is desirably a material which does not transmit moisture or oxygen as much as possible. As a material for the sealing substrate 404, a glass substrate, a quartz substrate, or a plastic substrate including fiberglass-reinforced plastics (FRP), polyvinyl fluoride) (PVF), a polyester, an acrylic resin, or the like can be used.

As described above, the active matrix light-emitting device having the light-emitting element of one embodiment of the present invention can be obtained.

Figure 4A:
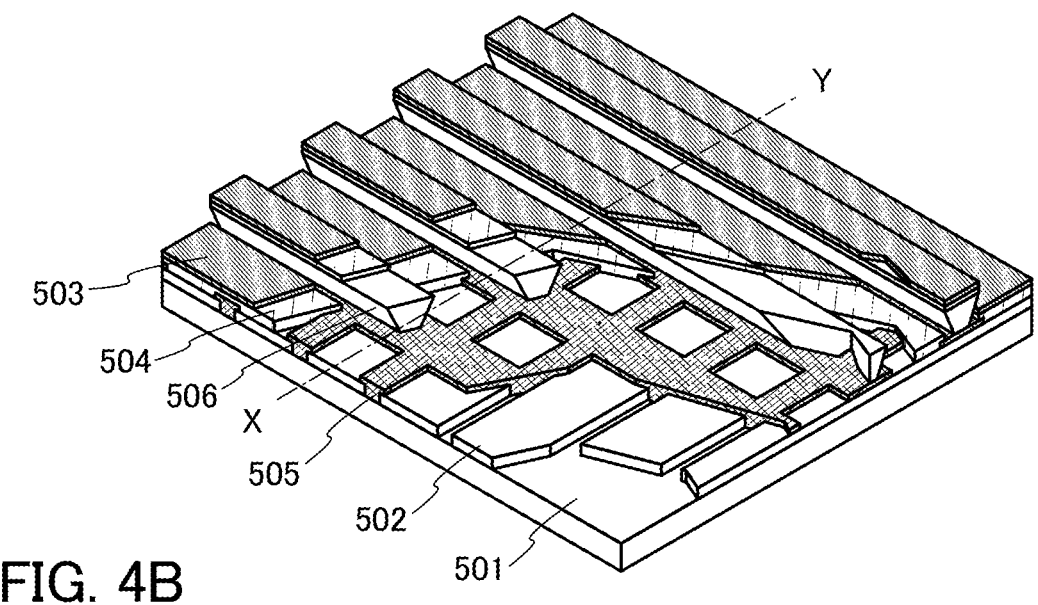
FIGS. 4A and 4B illustrate a light-emitting device according to one embodiment of the present invention.
Figure 4B:
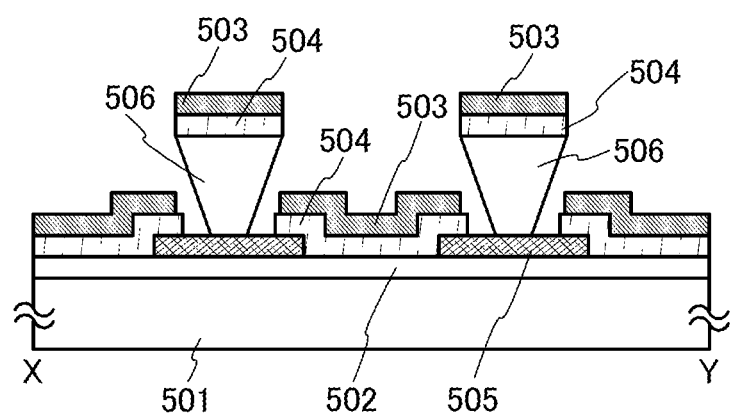

Further, the light-emitting element of one embodiment of the present invention can be used for a passive matrix light-emitting device instead of the above active matrix light-emitting device. FIGS. 4A and 4B illustrate a perspective view and a cross-sectional view of a passive matrix light-emitting device using the light-emitting element of one embodiment of the present invention. FIG. 4A is the perspective view of the light-emitting device, and FIG. 4B is the cross-sectional view taken along line X-Y in FIG. 4A.

In FIGS. 4A and 4B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 slope so that the distance between one sidewall and the other sidewall gradually decreases toward the surface of the substrate. In other words, a cross section taken along the direction of the short side of the partition layer 506 is trapezoidal, and the lower side (a side in contact with the insulating layer 505 which is one of a pair of parallel sides of the trapezoidal cross section) is shorter than the upper side (a side not in contact with the insulating layer 505 which is the other of the pair of parallel sides). By providing the partition layer 506 in such a manner, a defect of the light-emitting element due to crosstalk or the like can be prevented.

Thus, the passive matrix light-emitting device having the light-emitting element of one embodiment of the present invention can be obtained.

The light-emitting devices described in this embodiment (the active matrix light-emitting device and the passive matrix light-emitting device) are both formed using the light-emitting element of one embodiment of the present invention, thereby having low power consumption.

This embodiment can be implemented in appropriate combination with the other embodiments.

(Embodiment 5)

In this embodiment, electronic devices and lighting devices including the light-emitting device described in Embodiment 4, which is one embodiment of the present invention, are described with reference to FIGS. 5A to 5D, FIG. 6, FIG. 7, FIG. 8, and FIGS. 9A to 9C.

Examples of the electronic devices include cameras such as video cameras and digital cameras, goggle type displays, navigation systems, audio reproducing devices (e.g., car audio systems and audio systems), computers, game machines, portable information terminals (e.g., mobile computers, cellular phones, portable game machines, and electronic book readers), image reproducing devices in which a recording medium is provided (specifically, devices that are capable of reproducing recording media such as digital versatile discs (DVDs) and provided with a display device that can display an image), and the like.

Figure 5A:
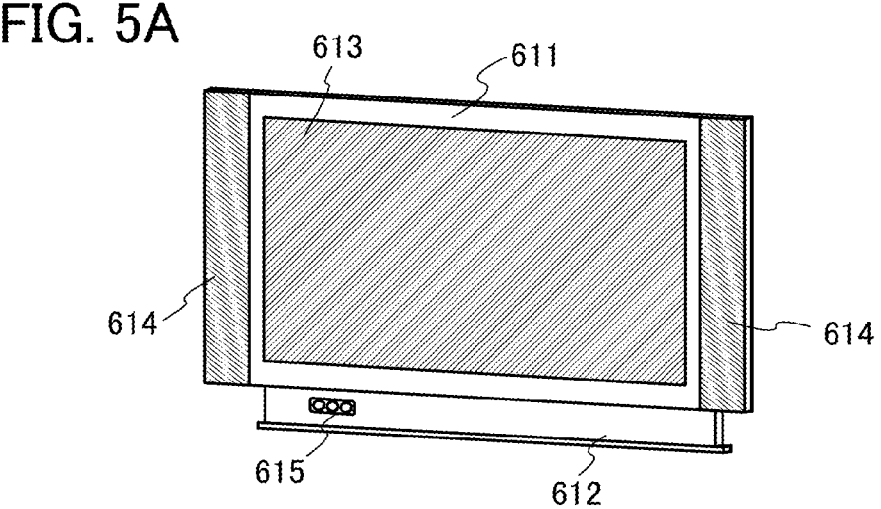
FIGS. 5A to 5D each illustrate an electronic device according to one embodiment of the present invention.

FIG. 5A illustrates a television set according to one embodiment of the present invention, which includes a housing 611, a supporting base 612, a display portion 613, speaker portions 614, video input terminals 615, and the like. In this television set, the light-emitting device of one embodiment of the present invention can be applied to the display portion 613. Since the light-emitting device of one embodiment of the present invention has low driving voltage, high emission efficiency, and a long lifetime, by the application of the light-emitting device of one embodiment of the present invention, a television set having high reliability and low power consumption can be obtained.

Figure 5B:
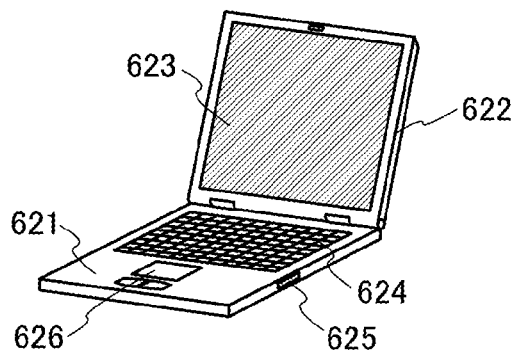

FIG. 5B illustrates a computer according to one embodiment of the present invention, which includes a main body 621, a housing 622, a display portion 623, a keyboard 624, an external connection port 625, a pointing device 626, and the like. In this computer, the light-emitting device of one embodiment of the present invention can be applied to the display portion 623. Since the light-emitting device of one embodiment of the present invention has low driving voltage, high emission efficiency, and a long lifetime, by the application of the light-emitting device of one embodiment of the present invention, a computer having high reliability and low power consumption can be obtained.

Figure 5C:
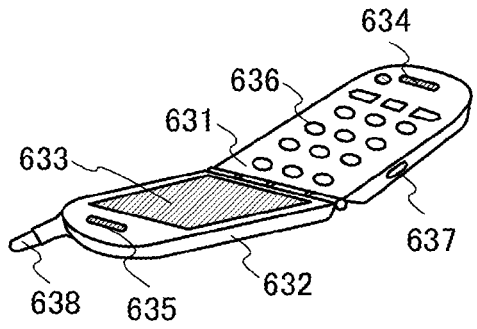

FIG. 5C illustrates a cellular phone according to one embodiment of the present invention, which includes a main body 631, a housing 632, a display portion 633, an audio input portion 634, an audio output portion 635, operation keys 636, an external connection port 637, an antenna 638, and the like. In this cellular phone, the light-emitting device of one embodiment of the present invention can be applied to the display portion 633. Since a light-emitting device of one embodiment of the present invention has low driving voltage, high emission efficiency, and a long lifetime, by the application of the light-emitting device of one embodiment of the present invention, a cellular phone having high reliability and low power consumption can be obtained.

Figure 5D:
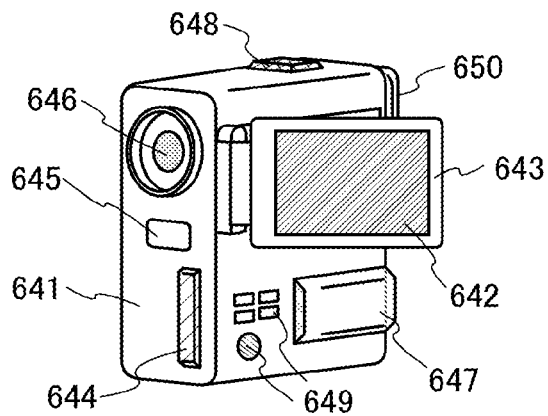

FIG. 5D illustrates a camera according to one embodiment of the present invention, which includes a main body 641, a display portion 642, a housing 643, an external connection port 644, a remote control receiving portion 645, an image receiving portion 646, a battery 647, an audio input portion 648, operation keys 649, an eyepiece portion 650, and the like. In this camera, the light-emitting device of one embodiment of the present invention can be applied to the display portion 642. Since the light-emitting device of one embodiment of the present invention has low driving voltage, high emission efficiency, and a long lifetime, by the application of the light-emitting device of one embodiment of the present invention, a camera having high reliability and low power consumption can be obtained.

As described above, the applicable range of the light-emitting device of one embodiment of the present invention is so wide that the light-emitting device can be applied to electronic devices in a variety of fields. With use of a light-emitting device of one embodiment of the present invention, an electronic device having high reliability and low power consumption can be obtained.

Figure 6:
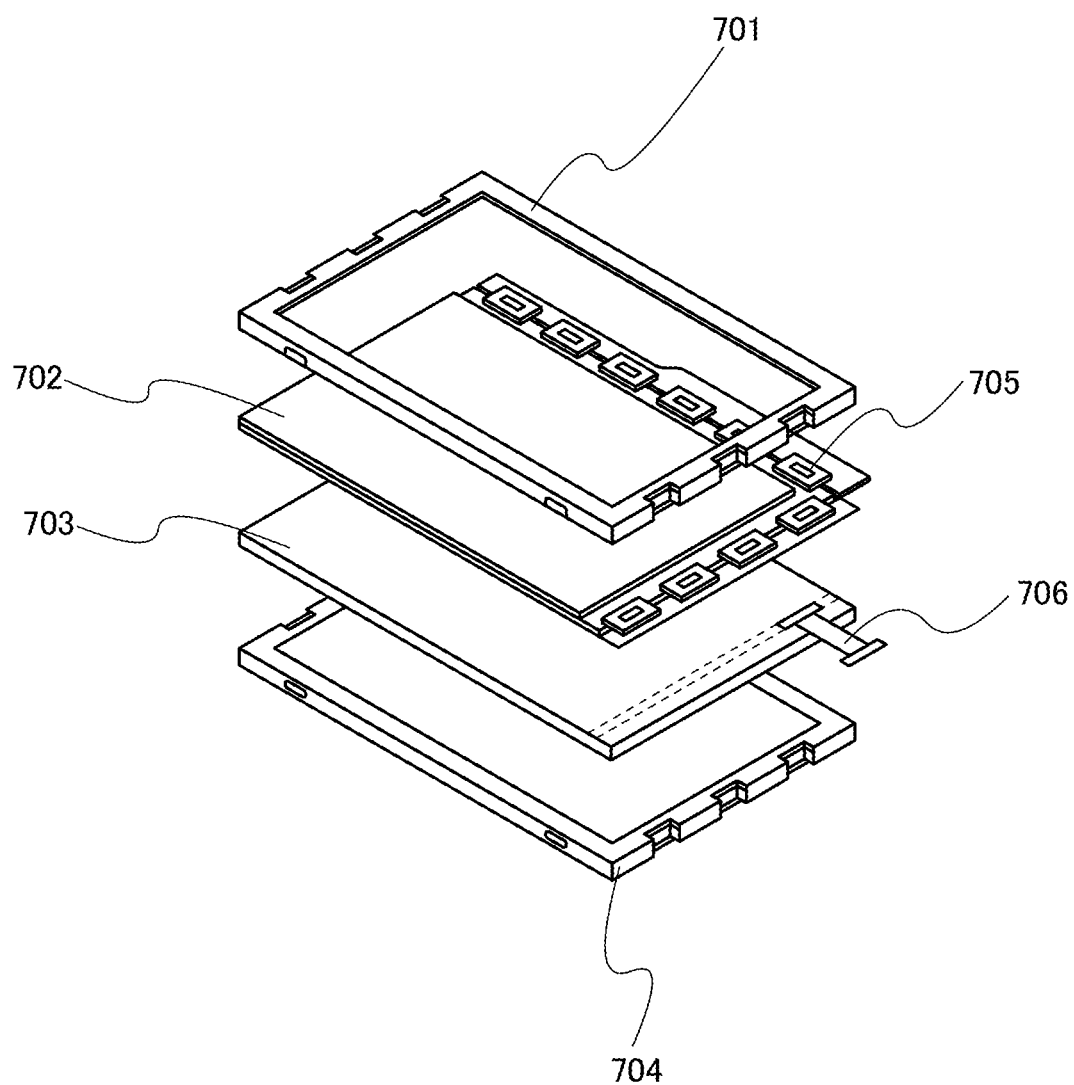
FIG. 6 illustrates a liquid crystal display device according to one embodiment of the present invention.

The light-emitting device of one embodiment of the present invention can also be used as a lighting device. FIG. 6 illustrates an example of a liquid crystal display device using the light-emitting device of one embodiment of the present invention as a backlight. The liquid crystal display device illustrated in FIG. 6 includes a housing 701, a liquid crystal layer 702, a backlight 703, and a housing 704. The liquid crystal layer 702 is connected to a driver IC 705. The light-emitting device of one embodiment of the present invention is used as the backlight 703, and current is supplied through a terminal 706.

By use of the light-emitting device according to one embodiment of the present invention as a backlight of a liquid crystal display device as described above, a backlight having low power consumption can be obtained. Moreover, since the light-emitting device of one embodiment of the present invention is a lighting device for surface light emission and the enlargement of the light-emitting device is possible, the backlight can be made larger. Accordingly, a larger-area liquid crystal display device having low power consumption can be obtained.

Figure 7:
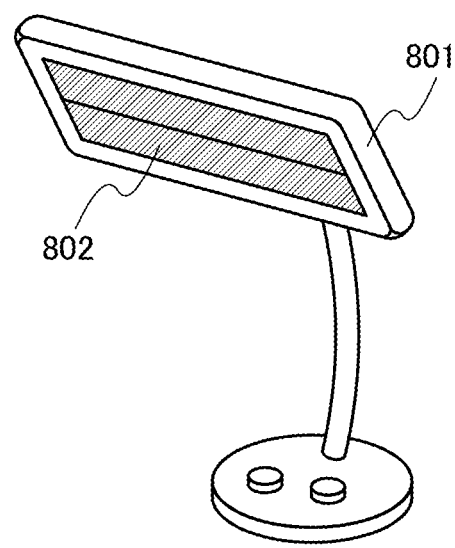
FIG. 7 illustrates a lighting device according to one embodiment of the present invention.

FIG. 7 illustrates an example in which the light-emitting device of one embodiment of the present invention is used for a desk lamp which is a lighting device. The desk lamp in FIG. 7 has a housing 801 and a light source 802, and the light-emitting device of one embodiment of the present invention is used as the light source 802. Since the light-emitting device of one embodiment of the present invention has low driving voltage, high emission efficiency, and a long lifetime, by the application of the light-emitting device of one embodiment of the present invention, a desk lamp having high reliability and low power consumption can be obtained.

Figure 8:
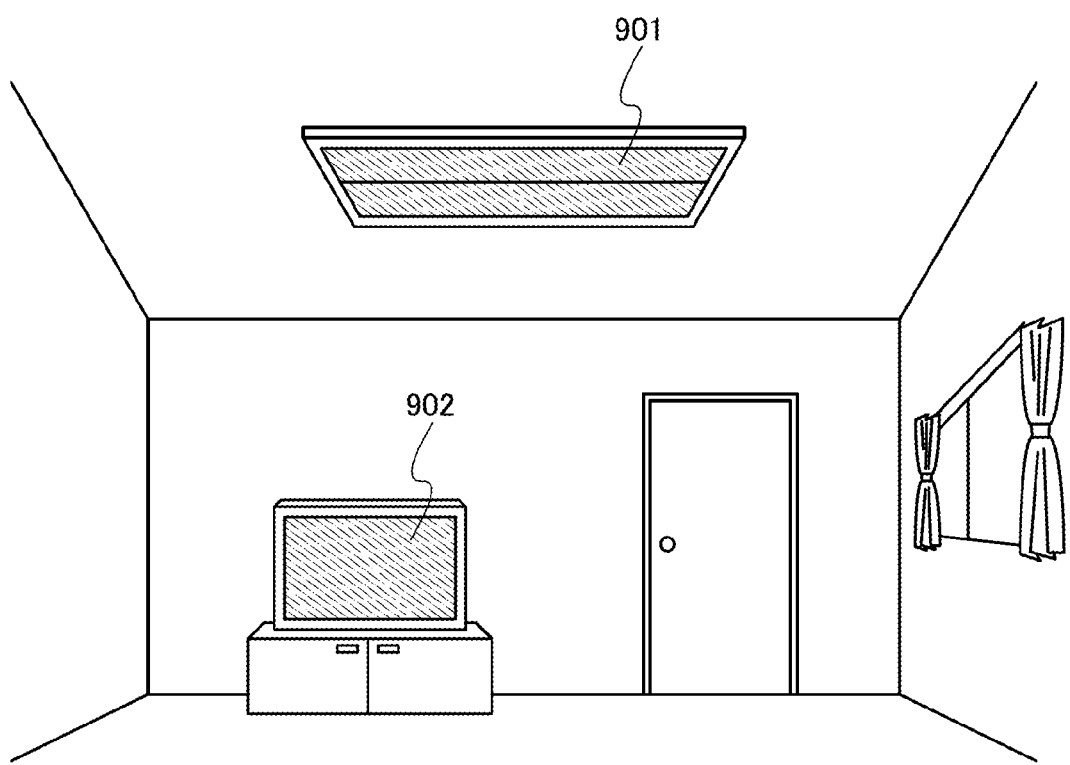
FIG. 8 illustrates a lighting device according to one embodiment of the present invention.

FIG. 8 illustrates an example in which the light-emitting device of one embodiment of the present invention is used for an indoor lighting device 901. Since the light-emitting device of one embodiment of the present invention can have a larger area, the light-emitting device of one embodiment of the present invention can be used as a lighting system having a large area. Further, since the light-emitting device of one embodiment of the present invention has low driving voltage, high emission efficiency, and a long lifetime, by the application of the light-emitting device of one embodiment of the present invention, a lighting device having high reliability and low power consumption can be obtained. In a room where the light-emitting device of one embodiment of the present invention is used as the indoor lighting device 901 as above, a television set 902 of one embodiment of the present invention as described referring to FIG. 5A can be installed so that public broadcasting and movies can be watched.

Figure 9A:
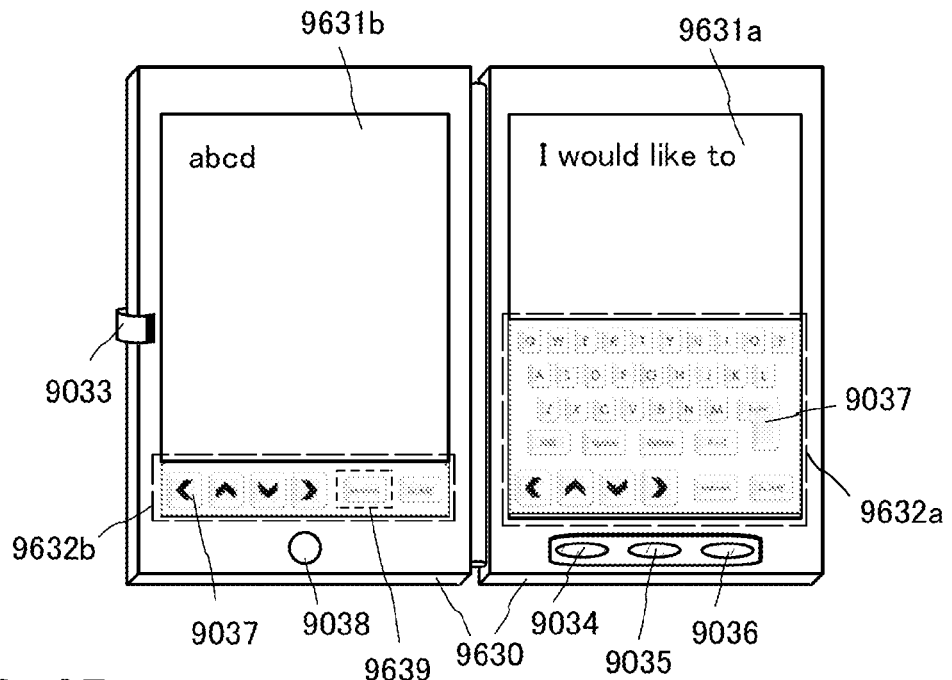
FIGS. 9A to 9C illustrate an electronic device according to one embodiment of the present invention.
Figure 9B:
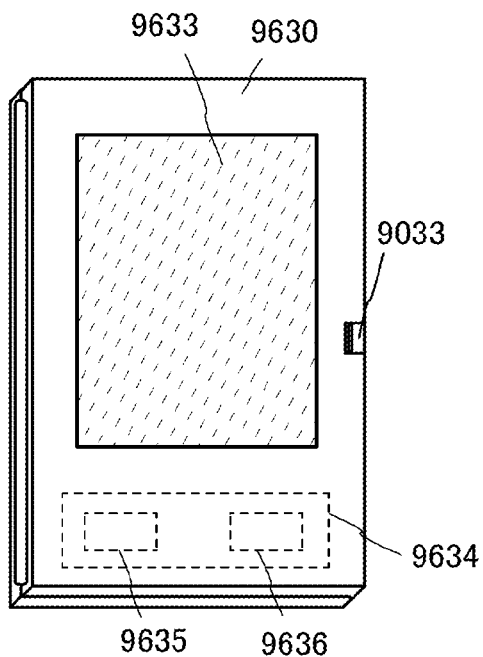

FIGS. 9A and 9B illustrate a tablet terminal that can be folded. In FIG. 9A, the tablet terminal is opened, and includes a housing 9630, a display portion 9631*a*, a display portion 9631*b*, a display-mode switching button 9034, a power button 9035, a power-saving-mode switching button 9036, a clip 9033, and an operation button 9038.

The tablet terminal is manufactured using the light-emitting device of one embodiment of the present invention for one or both of the display portion 9631a and the display portion 9631b.

A touch panel area 9632a can be provided in part of the display portion 9631a, in which area, data can be input by touching displayed operation keys 9037. Note that half of the display portion 9631a has only a display function and the other half has a touch panel function. However, one embodiment of the present invention is not limited to this structure, and the entire display portion 9631a may have a touch panel function. For example, a keyboard can be displayed on the entire display portion 9631a to be used as a touch panel, and the display portion 9631b can be used as a display screen.

A touch panel area 9632b can be provided in part of the display portion 9631b like in the display portion 9631a. When a keyboard display switching button 9639 displayed on the touch panel is touched with a finger, a stylus, or the like, a keyboard can be displayed on the display portion 9631b.

The touch panel area 9632a and the touch panel area 9632b can be controlled by touch input at the same time.

The display-mode switching button 9034 allows switching between a landscape mode and a portrait mode, color display and black-and-white display, and the like. The power-saving-mode switching button 9036 allows optimizing the display luminance in accordance with the amount of external light in use, which is detected by an optical sensor incorporated in the tablet terminal. In addition to the optical sensor, other detecting devices such as sensors for detecting inclination, like a gyroscope or an acceleration sensor, may be incorporated in the tablet terminal.

Although the display portion 9631a and the display portion 9631b have the same display area in FIG. 9A, one embodiment of the present invention is not limited to this example. The display portion 9631a and the display portion 9631b may have different areas or different display quality. For example, higher definition images may be displayed on one of the display portions 9631a and 9631b.

FIG. 9B illustrates the tablet terminal folded, which includes the housing 9630, a solar battery 9633, a charge and discharge control circuit 9634, a battery 9635, and a DCDC converter 9636. Note that FIG. 9B shows an example in which the charge and discharge control circuit 9634 includes the battery 9635 and the DCDC converter 9636.

Since the tablet terminal can be folded, the housing 9630 can be closed when not in use. Thus, the display portions 9631a and 9631b can be protected, which makes it possible to provide a tablet terminal with high durability and improved reliability for long-term use.

The tablet terminal illustrated in FIGS. 9A and 9B can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs).

The solar battery 9633, which is attached on the surface of the tablet terminal, supplies electric power to a touch panel, a display portion, an image signal processor, and the like. Note that a structure in which the solar battery 9633 is provided on one or both surfaces of the housing 9630 is preferable because the battery 9635 can be charged efficiently. The use of a lithium ion battery as the battery 9635 is advantageous in downsizing or the like.

Figure 9C:
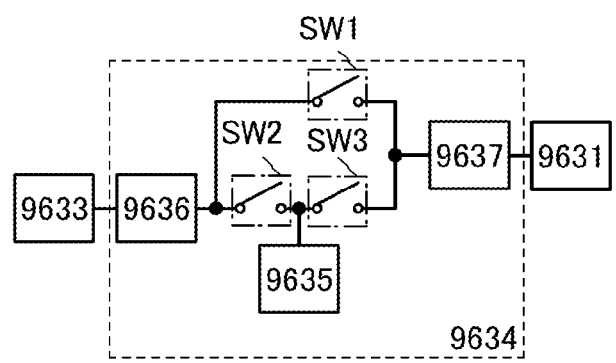

The structure and operation of the charge and discharge control circuit 9634 illustrated in FIG. 9B are described with reference to a block diagram of FIG. 9C. FIG. 9C illustrates the solar battery 9633, the battery 9635, the DCDC converter 9636, a converter 9637, switches SW1 to SW3, and the display portion 9631. The battery 9635, the DCDC converter 9636, the converter 9637, and the switches SW1 to SW3 correspond to the charge and discharge control circuit 9634 in FIG. 9B.

First, description is made on an example of the operation in the case where power is generated by the solar battery 9633 using external light. The voltage of power generated by the solar battery 9633 is raised or lowered by the DCDC converter 9636 so that a voltage for charging the battery 9635 is obtained. When the display portion 9631 is operated with the power from the solar battery 9633, the switch SW1 is turned on and the voltage of the power is raised or lowered by the converter 9637 to a voltage needed for operating the display portion 9631. When display is not performed on the display portion 9631, the switch SW1 is turned off and the switch SW2 is turned on so that the battery 9635 can be charged.

Although the solar battery 9633 is shown as an example of a power generation means, there is no particular limitation and the battery 9635 may be charged with another power generation means such as a piezoelectric element or a thermoelectric conversion element (Peltier element). For example, the battery 9635 may be charged with a non-contact power transmission module which is capable of charging by transmitting and receiving power wirelessly (without contact), or another charge means used in combination.

This embodiment can be implemented in appropriate combination with the other embodiments.

EXAMPLE 1

Synthesis Example 1

This example shows a method of synthesizing 6,11-bis[3-(dibenzothiophen-4-yl)phenyl]dibenzo[f,h]quinoxaline (abbreviation: 6,11 mDBTPDBq-II) represented by the following structural formula (100).

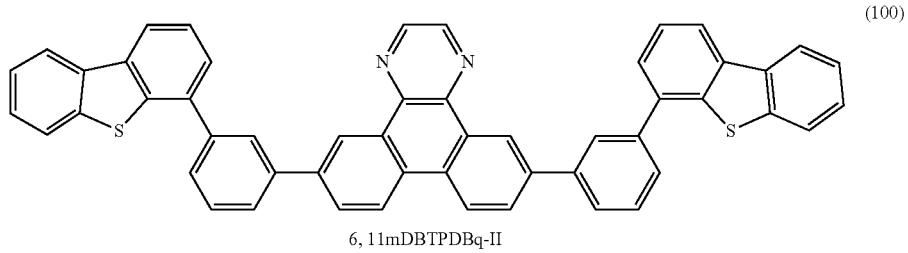 [SMILES: c1cc(-c2ccc3c4ccc(-c5cccc(-c6cccc7c6sc6ccccc67)c5)cc4c4nccnc4c3c2)cc(-c2cccc3c2sc2ccccc23)c1]

6,11mDBTPDBq-II

Synthesis of 6,11mDBTPDBq-II

A scheme for the synthesis of 6,11mDBTPDBq-II is illustrated in (C-1).

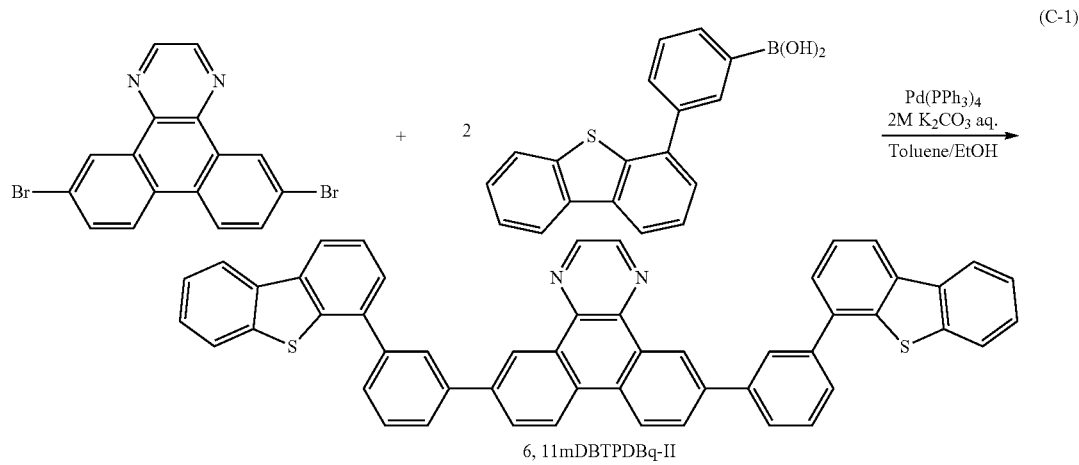

(C-1)

In a 100-mL three-neck flask were put 0.6 g (2.0 mmol) of 6,11-dibromodibenzo[f,h]quinoxaline, 1.3 g (4.2 mmol) of 3-(dibenzothiophen-4-yl)phenylboronic acid, 30 mL of toluene, 3 mL of ethanol, and 3 mL of a 2M aqueous solution of potassium carbonate. The mixture was degassed by being stirred under reduced pressure, and the air in the flask was replaced with nitrogen. To this mixture was added 46 mg (0.4 mmol) of tetrakis(triphenylphosphine)palladium(0). The mixture was stirred under a nitrogen stream at 80° C. for 15 hours. After the reaction, a solid precipitated in the system was subjected to suction filtration to give a filtrate and a residue.

Water was added to the obtained residue, the mixture was irradiated with ultrasonic waves, and a solid was collected by suction filtration. Ethanol was added to this solid, the mixture was irradiated with ultrasonic waves, and a solid was collected by suction filtration. The obtained solid was dissolved in toluene. This solution was suction-filtered through alumina and Celite (produced by Wako Pure Chemical Industries, Ltd., Catalog No. 531-16855) and the obtained filtrate was concentrated to give a solid (solid A).

Further, organic substances were extracted with toluene from the aqueous layer of the filtrate obtained in the first suction filtration. The solution of the extracted organic substances and the organic layer of the above filtrate were combined and washed with a saturated aqueous solution of sodium hydrogen carbonate and then with saturated brine, and magnesium sulfate was added thereto so as to adsorb moisture. The obtained mixture was gravity-filtered, and the filtrate was concentrated to give a solid (solid B).

The obtained solids were combined (Solid A+Solid B) and purified by silica gel column chromatography. A mixed solvent of toluene and hexane (toluene:hexane=1:20) was used as a developing solvent. The obtained fraction was concentrated to give 1.5 g of a white solid in a yield of 75%.

The Rf values of the objective substance and 6,11-dibromodibenzo[f,h]quinoxaline were respectively 0.20 and 0.55, which were found by silica gel thin layer chromatography (TLC) (with a developing solvent of ethyl acetate and hexane in a ratio of 1:10).

This compound was identified as 6,11mDBTPDBq-II, which was the objective substance, by nuclear magnetic resonance (NMR) spectroscopy.

$^1$H NMR data of the obtained substance are as follows: $^1$H NMR (CDCl$_3$, 300 MHz): δ (ppm)=7.48-7.51 (m, 4H), 7.62-7.73 (m, 6H), 7.80-7.88 (m, 4H), 7.98 (d, J=9.3 Hz, 2H), 8.18-8.26 (m, 8H), 8.78 (d, J=8.7 Hz, 2H), 8.93 (d, J=3.9 Hz, 2H), 9.60 (d, J=1.8 Hz, 2H).

Figure 10A:
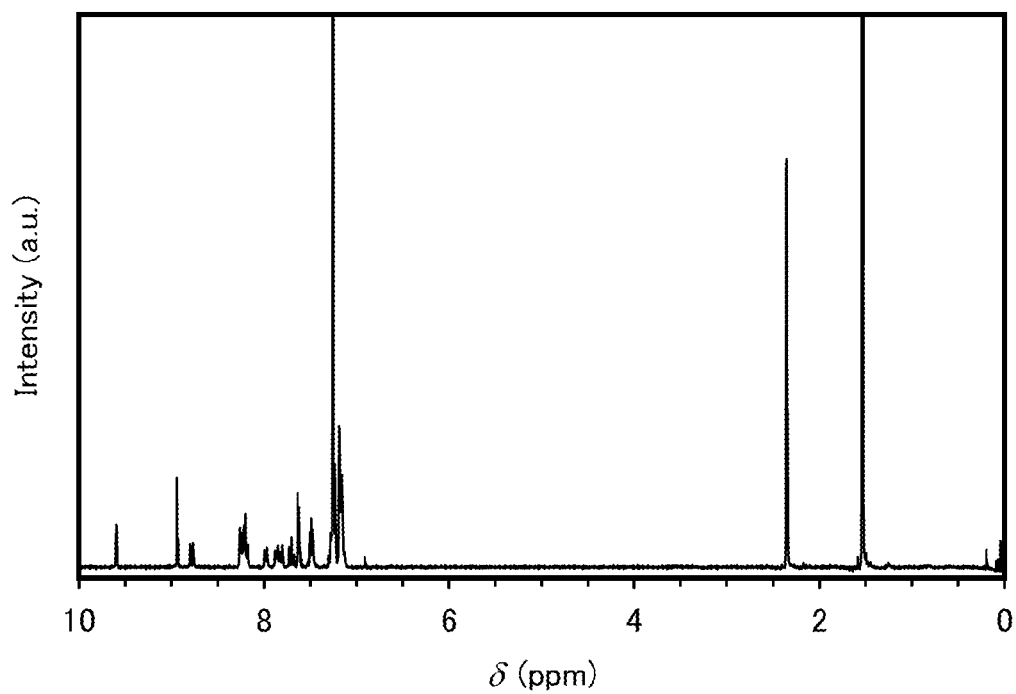
FIGS. 10A and 10B show $^1$H NMR charts of 6,11-bis[3-(dibenzothiophen-4-yl)phenyl]dibenzo[f,h]quinoxaline (abbreviation: 6,11 mDBTPDBq-II).
Figure 10B:
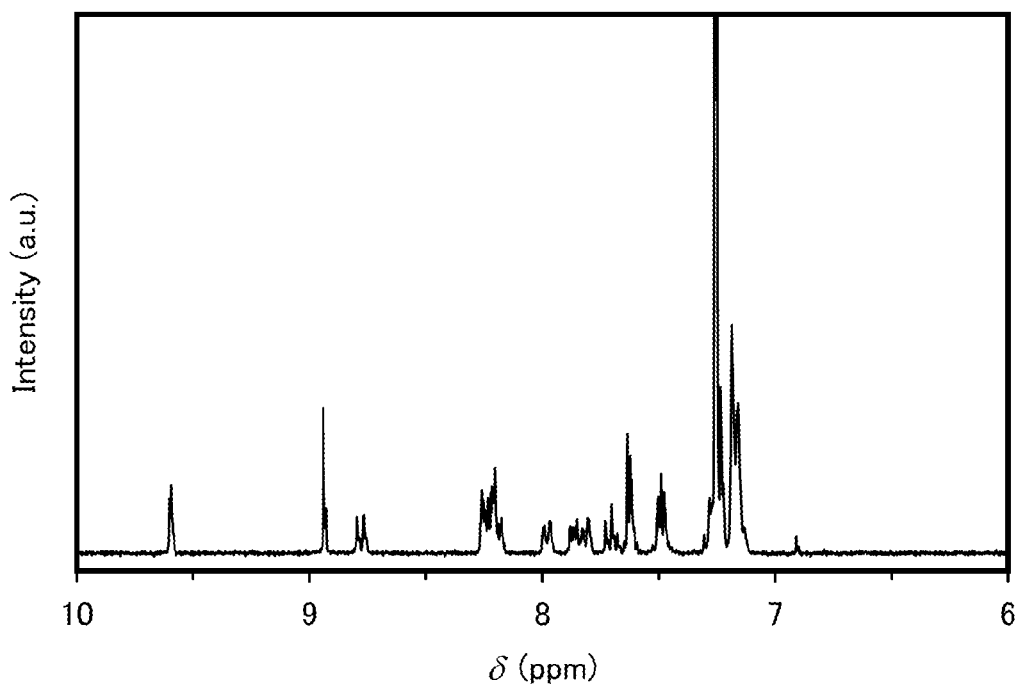

FIGS. 10A and 10B are $^1$H NMR charts. Note that FIG. 10B is a chart showing an enlarged part of FIG. 10A in the range of 6.00 ppm to 10.0 ppm.

Figure 11A:
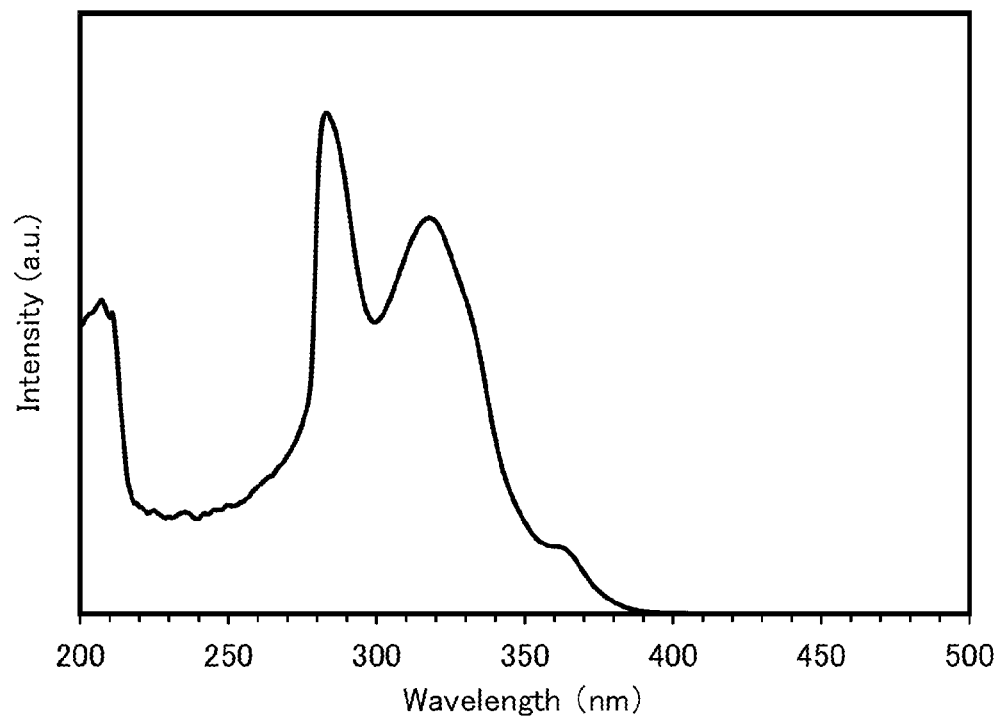
FIGS. 11A and 11B show an absorption spectrum and an emission spectrum of a toluene solution of 6,11mDBTPDBq-II.
Figure 11B:
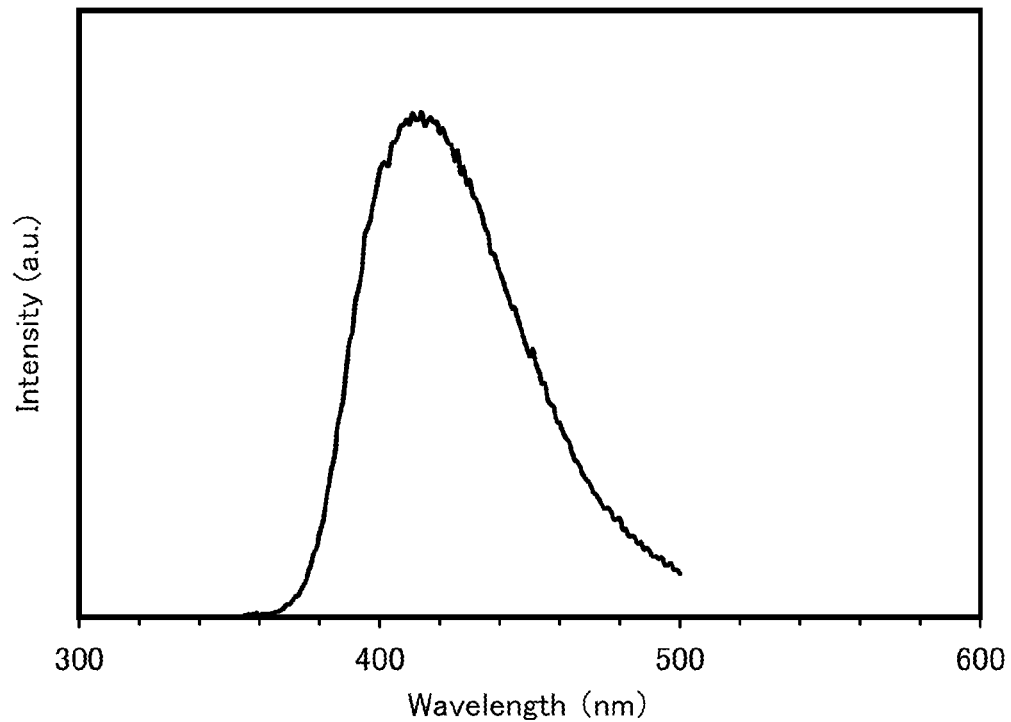
Figure 12A:
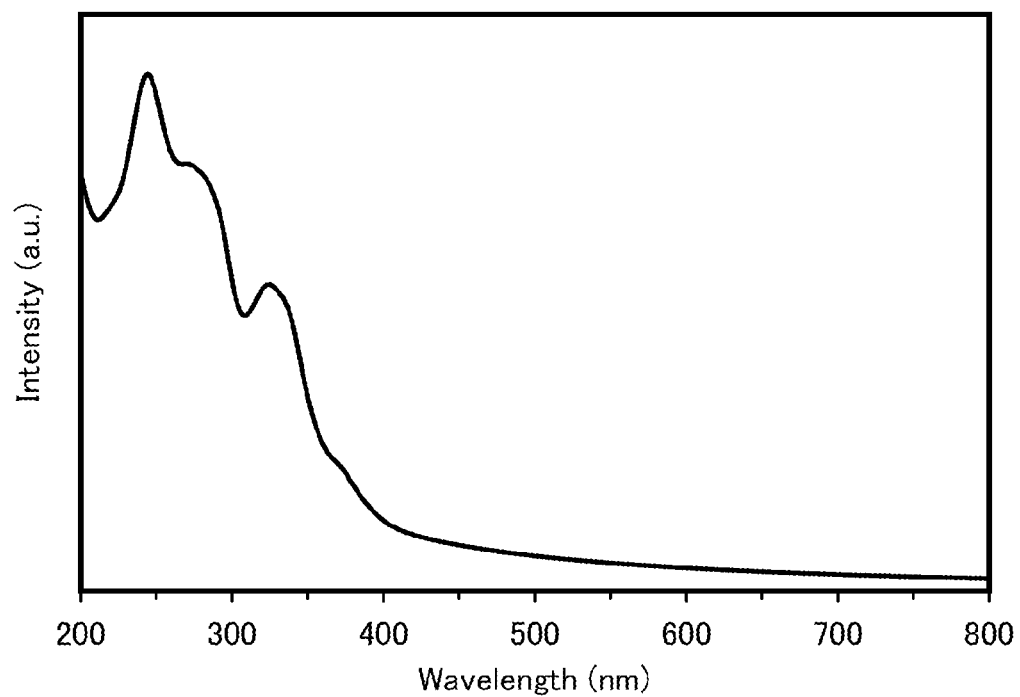
FIGS. 12A and 12B show an absorption spectrum and an emission spectrum of a thin film of 6,11mDBTPDBq-II.
Figure 12B:
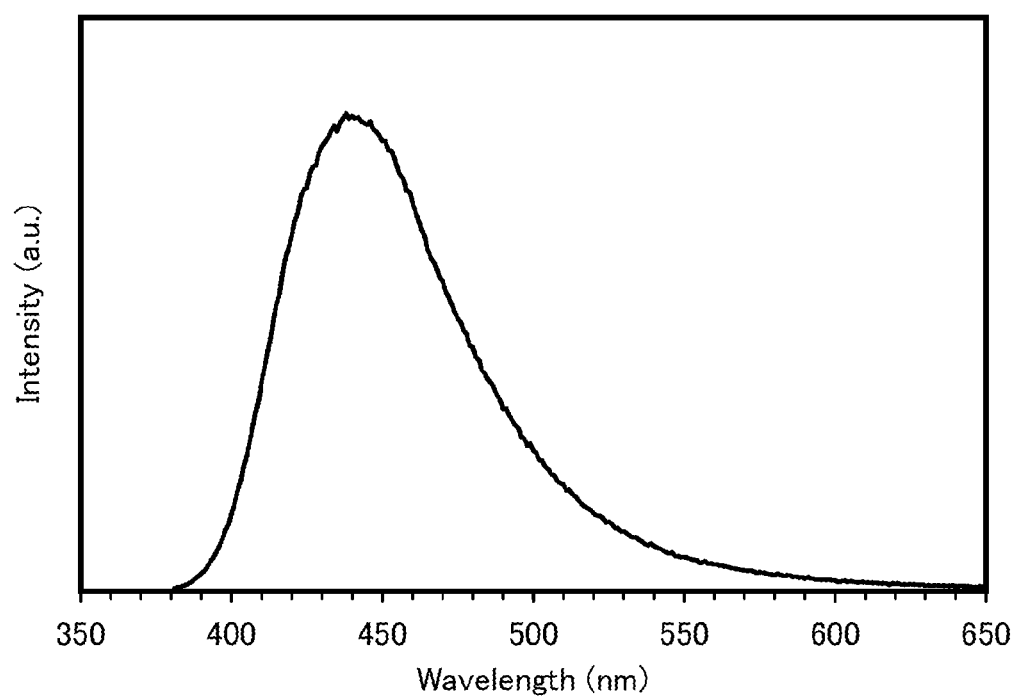

FIG. 11A shows an absorption spectrum of a toluene solution of 6,11mDBTPDBq-II, and FIG. 11B shows an emission spectrum thereof. FIG. 12A shows an absorption spectrum of a thin film of 6,11mDBTPDBq-II, and FIG. 12B shows an emission spectrum thereof. The absorption spectra were measured with an ultraviolet-visible spectrophotometer (V-550, manufactured by JASCO Corporation). The measurements were performed with samples prepared in such a manner that the solution was put in a quartz cell and the thin film was obtained by evaporation onto a quartz substrate. The absorption spectrum of the solution was obtained by subtracting the absorption spectra of quartz and toluene from the spectrum of the solution, and the absorption spectrum of the thin film was obtained by subtracting the absorption spectrum of a quartz substrate from the spectrum of the thin film. In FIGS. 11A and 11B and FIGS. 12A and 12B, the horizontal axis represents wavelength (nm) and the vertical axis represents intensity (arbitrary unit). In the case of the toluene solution, an absorption peak was observed at 364 nm, and an emission wavelength peak was 414 nm (at an excitation wavelength of 364 nm). In the case of the thin film, an absorption peak was observed at 366 nm, and an emission wavelength peak was 440 nm (at an excitation wavelength of 367 nm).

Electrophysical properties of a thin film of 6,11mDBTPDBq-II were evaluated (the measuring instrument was AC-2 produced by Riken Keiki, Co., Ltd.). Note that the measurement of electrophysical properties of the thin film was carried out as follows.

The HOMO level was obtained by conversion of the ionization potential measured with a photoelectron spectrometer (AC-2, manufactured by Riken Keiki Co., Ltd.) in the air into a negative value. The LUMO level was obtained in such a manner that the absorption edge, which was obtained from Tauc plot with an assumption of direct transition using data on the absorption spectrum of the thin film, was regarded as an optical energy gap and was added to the HOMO level.

From the results of the measurement of electrophisical properties of the thin film, the HOMO level, the LUMO level, and the band gap (Bg) were found to be −5.93 eV, −2.83 eV, and 3.10 eV, respectively.

The above results reveal that 6,11mDBTPDBq-II has a relatively deep HOMO level, a relatively shallow LUMO level, and a relatively wide Bg.

Electrochemical characteristics and electrophysical properties of a 6,11mDBTPDBq-II solution were also evaluated.

As a measuring method, cyclic voltammetry (CV) measurement was employed. An electrochemical analyzer (ALS model 600A or 600C, produced by BAS Inc.) was used for the measurement.

The HOMO level was found to be −6.22 eV, indicating that 6,11mDBTPDBq-II can efficiently inject holes into a material having a HOMO level which is close to this value. Further, since the HOMO level is deep (the value thereof is small), it is found that 6,11mDBTPDBq-II can efficiently inject holes into a material having a shallower HOMO level (a larger value) than 6,11mDBTPDBq-II.

The LUMO level was found to be −2.90 eV, indicating that 6,11mDBTPDBq-II can efficiently inject electrons into a material having a LUMO level which is close to this value. Further, since the LUMO level is shallow (the value thereof is large), it is found that 6,11mDBTPDBq-II can efficiently inject electrons into a material having a deeper LUMO level (a smaller value) than 6,11mDBTPDBq-II. In addition, the intensity of the reduction peak was almost constant even after 100 cycles. This indicates that 6,11mDBTPDBq-II has tolerance to the repetition of the reduction and the oxidation between a reduced state and a neutral state.

Note that the above-described cyclic voltammetry (CV) measurement was carried out as follows.

As for a solution used for the CV measurement, dehydrated N,N-dimethylformamide (DMF, product of Sigma-Aldrich Co. LLC., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration of tetra-n-butylammonium perchlorate was 100 mmol/L. The object to be measured was dissolved in the solvent such that the concentration thereof was 2 mmol/L. A platinum electrode (PTE platinum electrode, manufactured by BAS Inc.) was used as a working electrode, a platinum electrode (Pt counter electrode for VC-3 (5 cm), manufactured by BAS Inc.) was used as an auxiliary electrode, and an Ag/Ag$^+$ electrode (RE-7 reference electrode for nonaqueous solvent, manufactured by BAS Inc.) was used as a reference electrode. The CV measurement was performed at room temperature (20° C. to 25° C.). The scan rate at the CV measurement was set to 0.1 V/sec in all the measurement.

(Calculation of Potential Energy of Reference Electrode with respect to Vacuum Level)

First, a potential energy (eV) of the reference electrode (Ag/Ag$^+$ electrode), which was used in this example, with respect to the vacuum level was calculated. In other words, Fermi level of the Ag/Ag$^+$ electrode was calculated. It is known that the oxidation-reduction potential of ferrocene in methanol is +0.610 [V vs. SHE] with respect to the standard hydrogen electrode (Reference: Christian R. Goldsmith et al., J. Am. Chem. Soc., 124 (1) 83-96, 2002).

Using the reference electrode used in this example, the oxidation-reduction potential of ferrocene in methanol was calculated to be +0.11 [V vs. Ag/Ag$^+$]. Therefore, the potential energy of the reference electrode used in this example was found to be lower than that of the standard hydrogen electrode by 0.50 [eV].

Here, it is known that the potential energy of the standard hydrogen electrode with respect to the vacuum level is −4.44 eV (Reference: Toshihiro Ohnishi and Tamami Koyama, *High molecular EL material*, Kyoritsu shuppan, pp. 64-67). Therefore, the potential energy of the reference electrode, which was used in this example, with respect to the vacuum level was calculated as follows: −4.44−0.50=−4.94 [eV].

The oxidation characteristics of the compound of this example were measured in the following manner: the potential of the working electrode with respect to the reference electrode was scanned from 0.2 V to 1.5 V, and then from 1.5 V to 0.2 V.

Subsequently, the calculation of the HOMO level of the objective substance based on CV measurement is described in detail. In the measurement of the oxidation reaction characteristics, an oxidation peak potential $E_{pa}$ [V] and a reduction peak potential $E_{pc}$ [V] were calculated. Accordingly, a half-wave potential (intermediate potential between $E_{pa}$ and $E_{pc}$) can be calculated by $(E_{pa}+E_{pc})/2$ [V]. This means that the compound of this example is oxidized by an electric energy corresponding to the value of the half-wave potential [V vs. Ag/Ag$^+$], and this energy corresponds to the HOMO level.

The reduction characteristics of the compound of this example were measured in the following manner: the potential of the working electrode with respect to the reference electrode was scanned from −1.2 V to −2.2 V, and then from −2.2 V to −1.2 V.

Subsequently, the calculation of the LUMO level of the objective substance based on CV measurement is described in detail. In the measurement of the reduction reaction characteristics, a reduction peak potential $E_{pc}$ [V] and an oxidation peak potential $E_{pa}$ [V] were calculated. Accordingly, a half-wave potential (intermediate potential between $E_{pa}$ and $E_{pc}$) can be calculated by $(E_{pa}+E_{pc})/2$ [V]. This means that the compound of this example is reduced by an electric energy corresponding to the value of the half-wave potential [V vs. Ag/Ag$^+$], and this energy corresponds to the LUMO level.

EXAMPLE 2

Figure 13:
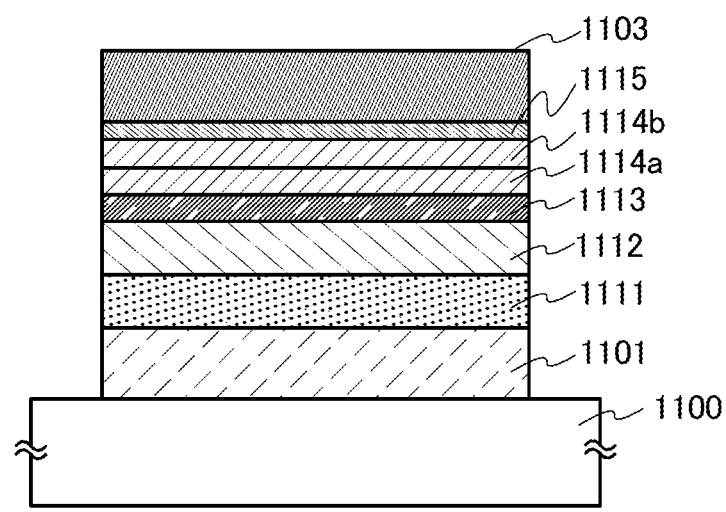
FIG. 13 illustrates a light-emitting element of examples.

In this example, a light-emitting element according to one embodiment of the present invention is described with reference to FIG. 13. Chemical formulae of materials used in this example are shown below. Note that the chemical formulae of the materials which are described above are omitted.

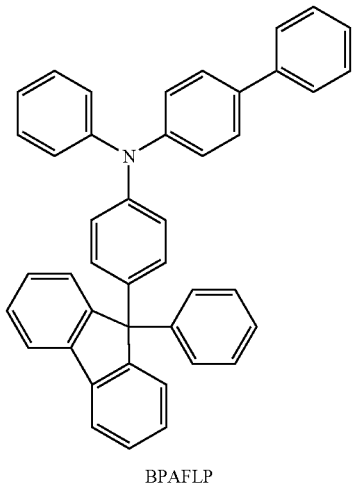

BPAFLP

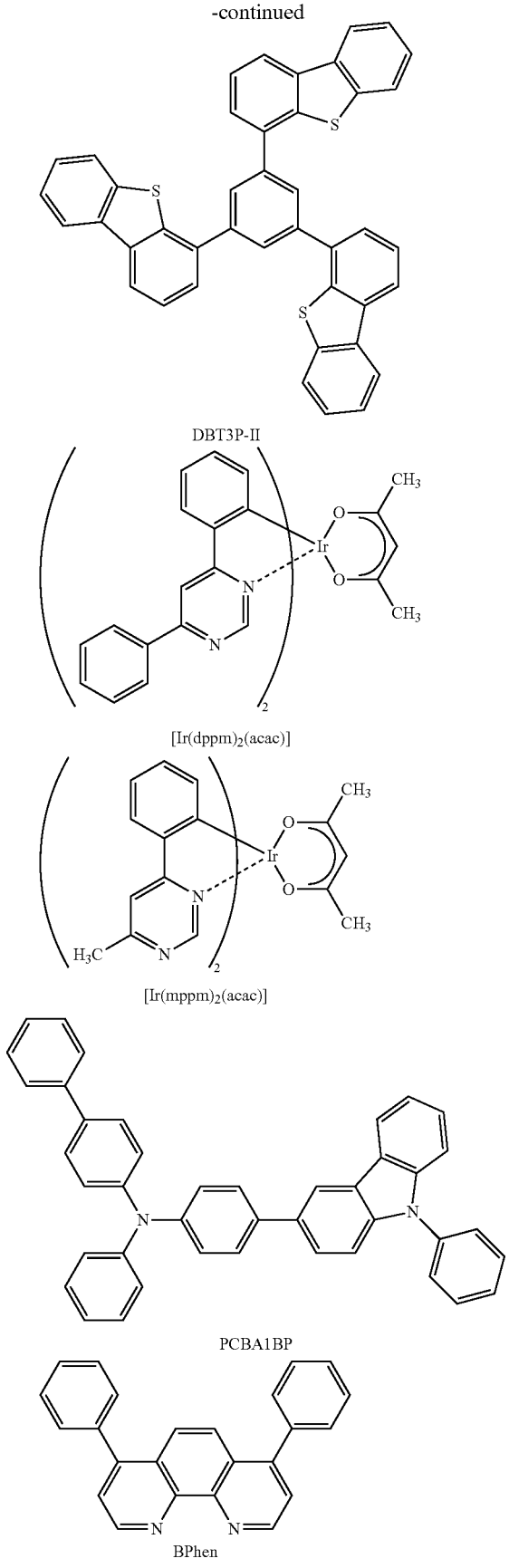

The following shows methods of fabricating light-emitting elements 1 and 2 of this example.

(Light-emitting Element 1)

First, indium tin oxide containing silicon oxide (ITSO) was deposited by a sputtering method on a glass substrate 1100, whereby a first electrode 1101 was formed. The thickness was 110 nm and the electrode area was 2 mm×2 mm. Here, the first electrode 1101 functions as an anode of the light-emitting element.

Next, as pretreatment for forming the light-emitting element over the substrate 1100, the surface of the substrate was washed with water, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Then, the substrate 1100 over which the first electrode 1101 was formed was fixed to a substrate holder provided in the vacuum evaporation apparatus such that the surface on which the first electrode 1101 was formed faced downward. The pressure in the vacuum evaporation apparatus was reduced to about $10^{-4}$ Pa. After that, over the first electrode 1101, 4,4',4''-(1,3,5-benzenetriyl)tri(dibenzothiophene) (abbreviation: DBT3P-II) and molybdenum(VI) oxide were co-evaporated by an evaporation method using resistance heating, so that a hole-injection layer 1111 was formed. The thickness of the hole-injection layer 1111 was set to 40 nm, and the weight ratio of DBT3P-II to molybdenum oxide was adjusted to 4:2 (=DBT3P-II:molybdenum oxide). Note that the co-evaporation method refers to an evaporation method in which evaporation is carried out from a plurality of evaporation sources at the same time in one treatment chamber.

Next, BPAFLP was deposited to a thickness of 20 nm on the hole-injection layer 1111, whereby a hole-transport layer 1112 was formed.

Further, 6,11mDBTPDBq-II synthesized in Example 1, PCBA1BP, and (acetylacetonato)bis(4,6-diphenylpyrimidinato)iridium(III) (abbreviation: [Ir(dppm)$_2$(acac)]) were co-evaporated, whereby a light-emitting layer 1113 was formed over the hole-transport layer 1112. Here, the weight ratio of 6,11mDBTPDBq-II to PCBA1BP and [Ir(dppm)$_2$(acac)] was adjusted to 0.8:0.2:0.05 (=6,11mDBTPDBq-II:PCBA1BP:[Ir(dppm)$_2$(acac)]). The thickness of the light-emitting layer 1113 was set to 40 nm.

Further, a 6,11mDBTPDBq-II film was formed to a thickness of 10 nm over the light-emitting layer 1113, whereby a first electron-transport layer 1114a was formed.

Then, BPhen film was formed to a thickness of 20 nm over the first electron-transport layer 1114a, whereby a second electron-transport layer 1114b was formed.

Further, a lithium fluoride (LiF) film was formed to a thickness of 1 nm over the second electron-transport layer 1114b by evaporation, whereby an electron-injection layer 1115 was formed.

Lastly, an aluminum film was formed to a thickness of 200 nm by evaporation, whereby a second electrode 1103 functioning as a cathode was formed. Thus, the light-emitting element 1 of this example was fabricated.

Note that, in the above evaporation process, evaporation was all performed by a resistance heating method.

(Light-emitting Element 2)

The light-emitting layer 1113 of the light-emitting element 2 was formed by co-evaporation of 6,11mDBTPDBq-II, PCBA1BP, and (acetylacetonato)bis(6-methyl-4-phenylpyrimidinato)iridium(III) (abbreviation: [Ir(mppm)$_2$(acac)]). Here, the weight ratio of 6,11mDBTPDBq-II to PCBA1BP and [Ir(mppm)$_2$(acac)] was adjusted to 0.7:0.3:0.05 (=6,11 mDBTPDBq-II:PCBA1BP: [Ir(mppm)$_2$(acac)]). The thickness of the light-emitting layer 1113 was set to 40 nm. The components other than the light-emitting layer 1113 were formed in the same manner as those of the light-emitting element 1.

Table 1 shows element structures of the light-emitting elements 1 and 2 obtained as described above.

(x, y)=(0.43, 0.56) at a luminance of 1000 cd/m$^2$. The light-emitting element 1 was found to emit light originating from [Ir(dppm)$_2$(acac)], and the light-emitting element 2 was found to emit light originating from [Ir(mppm)$_2$(acac)]. This reveals that 6,11mDBTPDBq-II, which is a heterocyclic compound according to one embodiment of the present invention, has a sufficiently high T1 level which enables a yellow phosphorescent material to emit light. Accordingly, it is found that 6,11mDBTPDBq-II can be used as a host material for yellow to red phosphorescent materials.

TABLE 1

|  | 1$^{st}$ electrode | HIL$^a$ | HTL$^b$ | EmL$^c$ | 1$^{st}$ ETL$^d$ | 2$^{nd}$ ETL$^d$ | EIL$^e$ | 2$^{nd}$ electrode |
|---|---|---|---|---|---|---|---|---|
| Light-emitting element 1 | ITSO 110 nm | DBT3P-II:MoOx (4:2) 40 nm | BPAFLP 20 nm | 6,11mDBTPDBq-II:PCBA1BP:[Ir(dppm)$_2$(acac)] (0.8:0.2:0.05) 40 nm | 6,11mDBTPDBq-II 10 nm | BPhen 20 nm | LiF 1 nm | Al 200 nm |
| Light-emitting element 2 | ITSO 110 nm | DBT3P-II:MoOx (4:2) 40 nm | BPAFLP 20 nm | 6,11mDBTPDBq-II:PCBA1BP:[Ir(mppm)$_2$(acac)] (0.7:0.3:0.05) 40 nm | 6,11mDBTPDBq-II 10 nm | BPhen 20 nm | LiF 1 nm | Al 200 nm |

$^a$Hole-injection layer.
$^b$Hole-transport layer.
$^c$Light-emitting layer.
$^d$Electron-transport layer.
$^e$Electron-injection layer.

In a glove box containing a nitrogen atmosphere, the light-emitting elements 1 and 2 were sealed with a glass substrate so as not to be exposed to the air. Then, operation characteristics of the elements were measured. Note that the measurement was carried out at room temperature (in an atmosphere kept at 25° C.).

Figure 14:
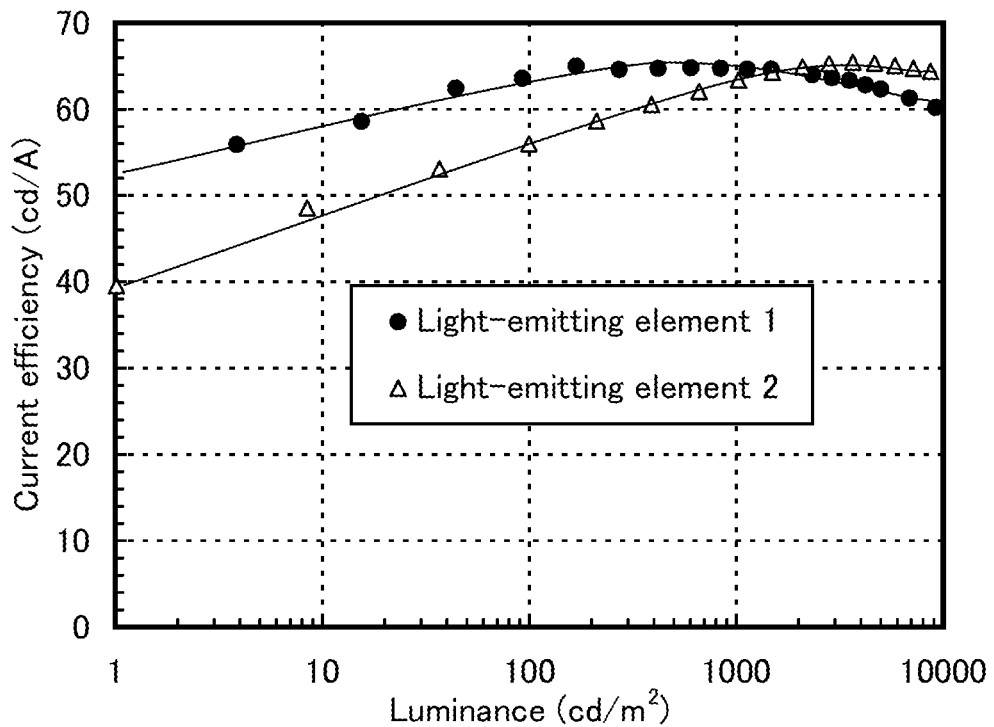
FIG. 14 shows luminance-current efficiency characteristics of light-emitting elements in Example 2.
Figure 15:
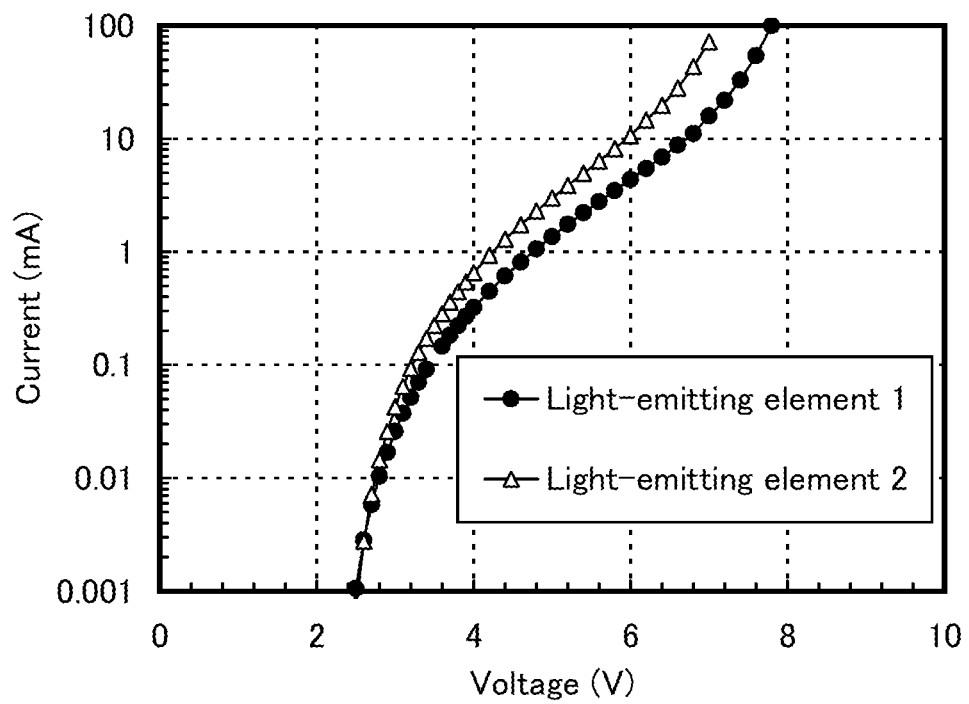
FIG. 15 shows voltage-current characteristics of the light-emitting elements in Example 2.
Figure 16:
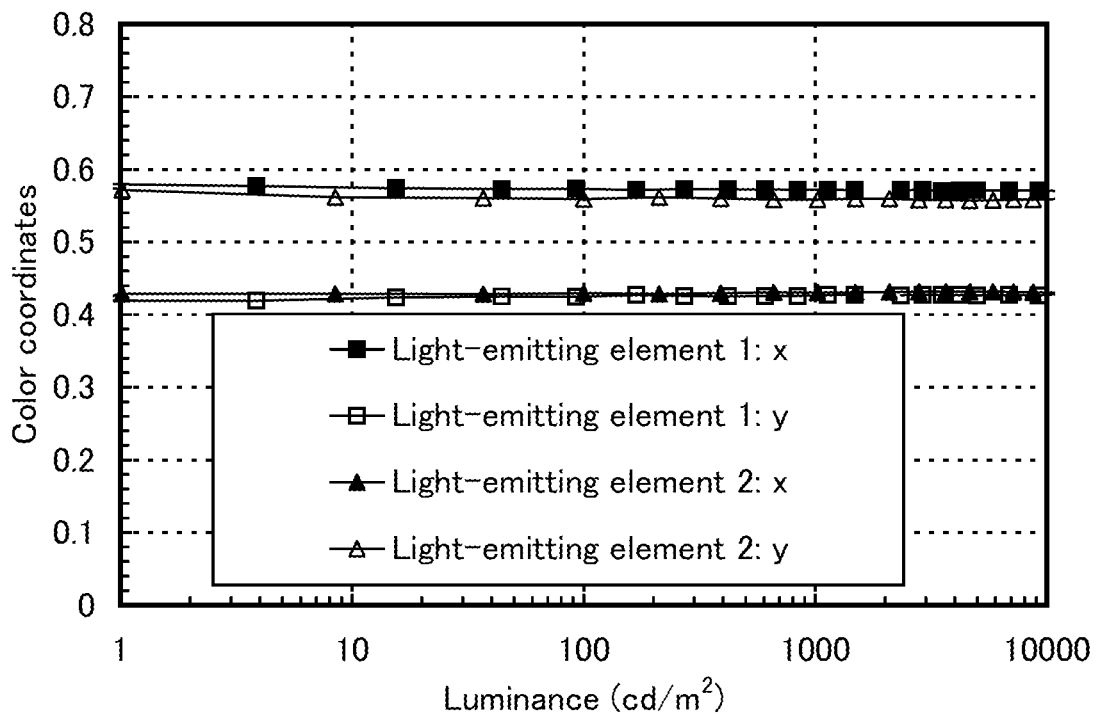
FIG. 16 shows luminance-chromaticity coordinate characteristics of the light-emitting elements in Example 2.
Figure 17:
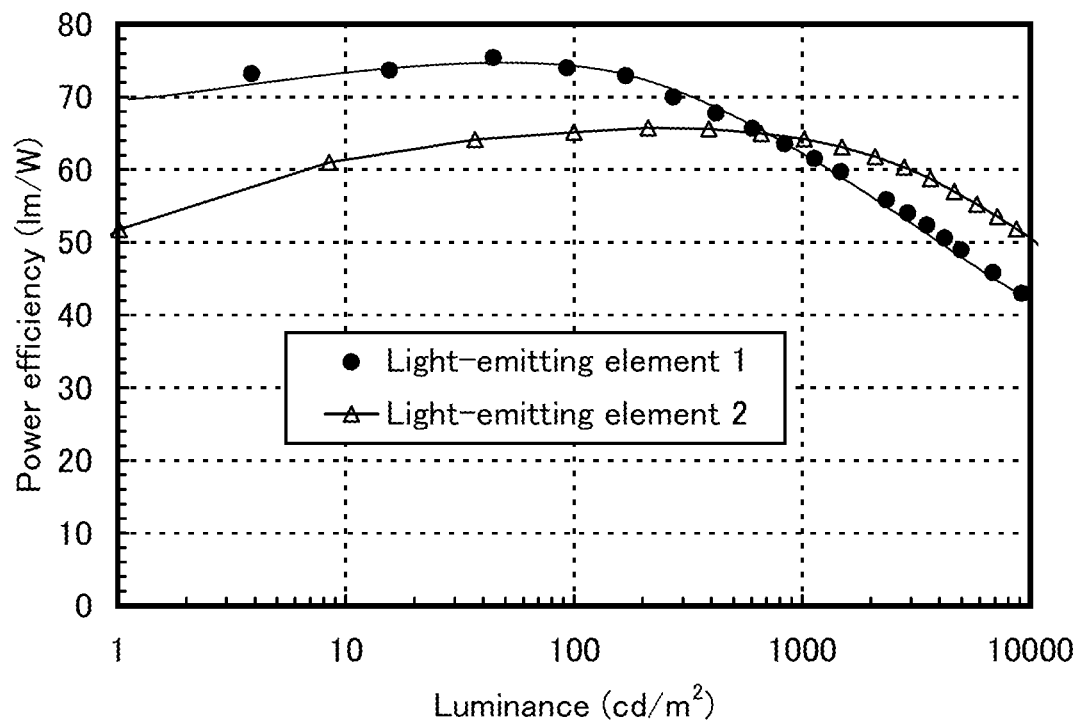
FIG. 17 shows luminance-power efficiency characteristics of the light-emitting elements in Example 2.

FIG. 14 shows luminance-current efficiency characteristics of the light-emitting elements 1 and 2. In FIG. 14, the horizontal axis represents luminance (cd/m$^2$) and the vertical axis represents current efficiency (cd/A). FIG. 15 shows voltage-current characteristics. In FIG. 15, the horizontal axis represents voltage (V) and the vertical axis represents current (mA). FIG. 16 shows the luminance-chromaticity coordinate characteristics. In FIG. 16, the horizontal axis represents luminance (cd/m$^2$) and the vertical axis represents chromaticity coordinate (the x-coordinate or the y-coordinate). FIG. 17 shows luminance-power efficiency characteristics. In FIG. 17, the horizontal axis represents luminance (cd/m$^2$) and the vertical axis represents power efficiency (lm/W). Table 2 shows voltage (V), current density (mA/cm$^2$), CIE chromaticity coordinates (x, y), luminance (cd/m$^2$), current efficiency (cd/A), and external quantum efficiency (%) of each light-emitting element at a luminance of around 1000 cd/m$^2$.

FIG. 15 and Table 2 reveal that both the light-emitting element 1 and the light-emitting element 2 are driven at a low voltage. In the light-emitting element 1 and the light-emitting element 2, 6,11mDBTPDBq-II, which is a heterocyclic compound according to one embodiment of the present invention, is used as a host material in the light-emitting layer and as a material in the first electron-transport layer. Accordingly, the light-emitting elements can be driven at a low voltage.

FIG. 14, FIG. 17, and Table 2 reveal that both the light-emitting element 1 and the light-emitting element 2 have high current efficiency, high external quantum efficiency, and high power efficiency. 6,11mDBTPDBq-II is a heterocyclic compound in which two dibenzothiophene rings are bonded to a dibenzo[f,h]quinoxaline ring through respective meta-phenylene groups. Accordingly, it is possible to provide a light-emitting element having high emission efficiency.

As shown in FIG. 16, the light-emitting elements 1 and 2 show substantially no change in color over a range from low luminance to high luminance. It can be said from this result that the light-emitting elements 1 and 2 are elements having excellent carrier balance.

Next, the light-emitting elements 1 and 2 were subjected to reliability tests. The results of the reliability tests are shown in

TABLE 2

|  | Voltage (V) | Current Density (mA/cm$^2$) | Chromaticity (x, y) | Luminance (cd/m$^2$) | Current efficiency (cd/A) | External quantum efficiency (%) |
|---|---|---|---|---|---|---|
| Light-emitting element 1 | 3.3 | 1.8 | (0.57, 0.43) | 1100 | 65 | 27 |
| Light-emitting element 2 | 3.1 | 1.6 | (0.43, 0.56) | 1000 | 63 | 18 |

Figure 18:
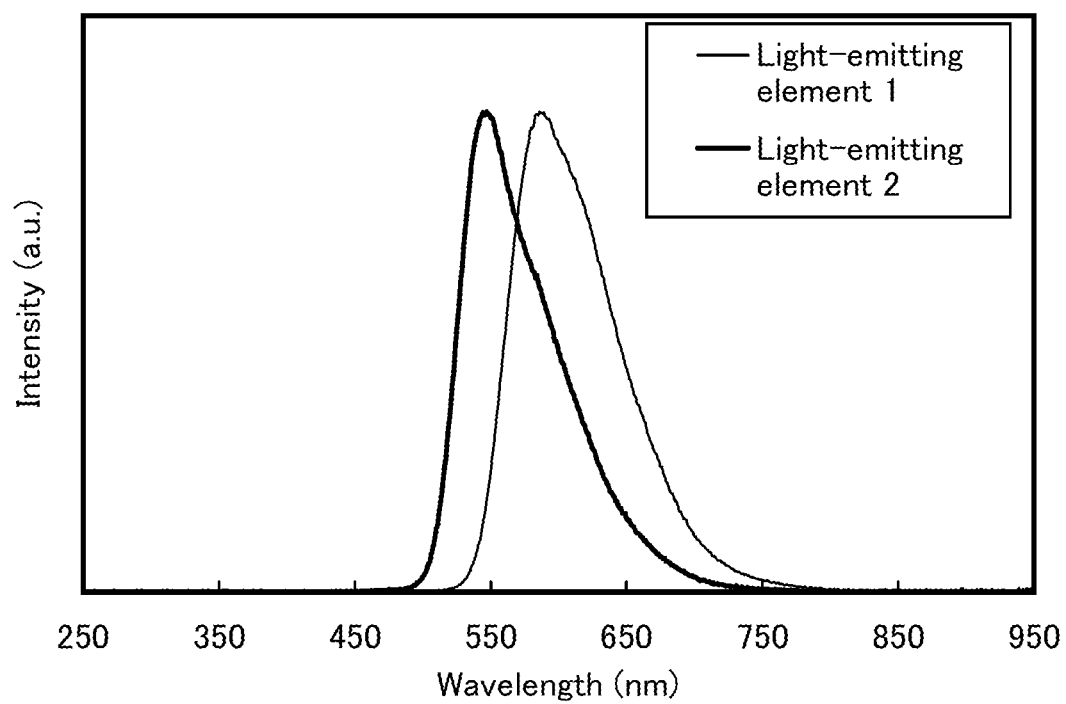
FIG. 18 shows emission spectra of the light-emitting elements in Example 2.
Figure 19:
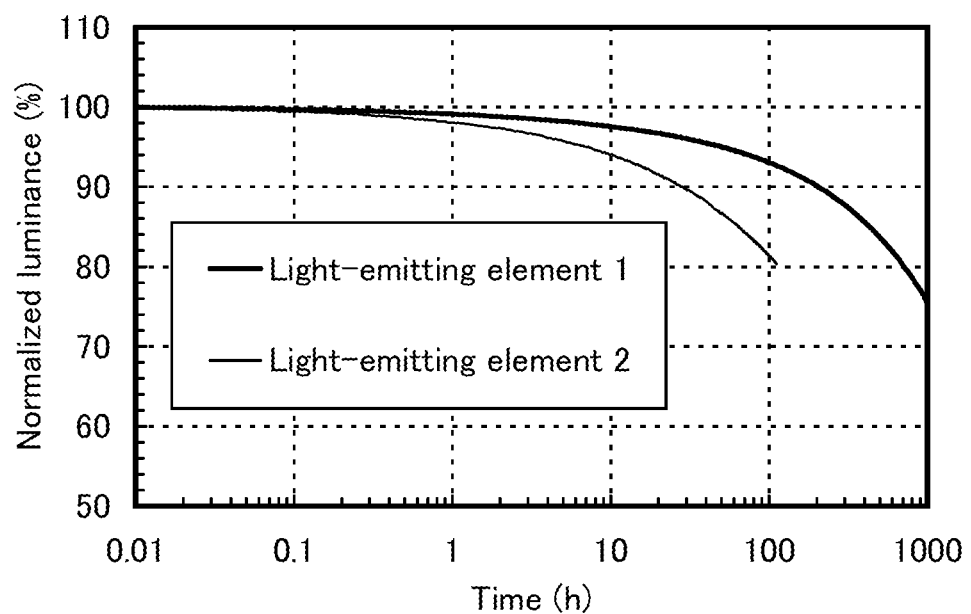
FIG. 19 shows results of reliability tests of the light-emitting elements in Example 2.

FIG. 18 shows emission spectra of the light-emitting elements 1 and 2, which were obtained by applying a current of 0.1 mA. In FIG. 18, the horizontal axis represents wavelength (nm) and the vertical axis represents emission intensity (arbitrary unit). As shown in FIG. 18 and Table 2, the CIE chromaticity coordinates of the light-emitting element 1 were (x, y)=(0.57, 0.43) at a luminance of 1100 cd/m$^2$, and the CIE chromaticity coordinates of the light-emitting element 2 were FIG. 19. In FIG. 19, the vertical axis represents normalized luminance (%) with an initial luminance of 100% and the horizontal axis represents driving time (h) of the elements. In the reliability tests, the light-emitting elements of this example were driven at room temperature under the conditions where the initial luminance was set to 5000 cd/m$^2$ and the current density was constant. FIG. 19 shows that the light-emitting element 1 kept 76% of the initial luminance after driving for 990 hours and the light-emitting element 2 kept 80% of the initial luminance after driving for 110 hours. These results of the reliability tests reveal that the light-emitting elements 1 and 2 each have a long lifetime.

As described above, by use of 6,11mDBTPDBq-II synthesized in Example 1 as the host material in the light-emitting layer and the material in the electron-transport layer, the light-emitting element can have a low driving voltage, high emission efficiency, or a long lifetime.

EXAMPLE 3

Synthesis Example 2

This example shows a method of synthesizing 6,11-bis[3-(9H-carbazol-9-yl)phenyl]dibenzo[f,h]quinoxaline (abbreviation: 6,11mCzP2DBq) represented by the following structural formula (102).

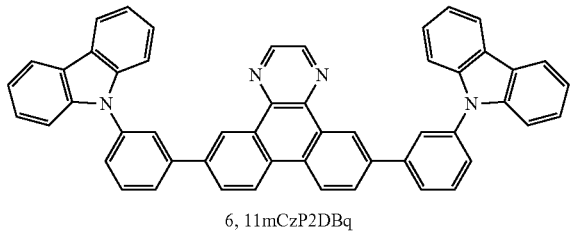

(102)

6,11mCzP2DBq

Synthesis of 6,11mCzP2DBq

A scheme for the synthesis of 6,11mCzP2DBq is illustrated in (D-1).

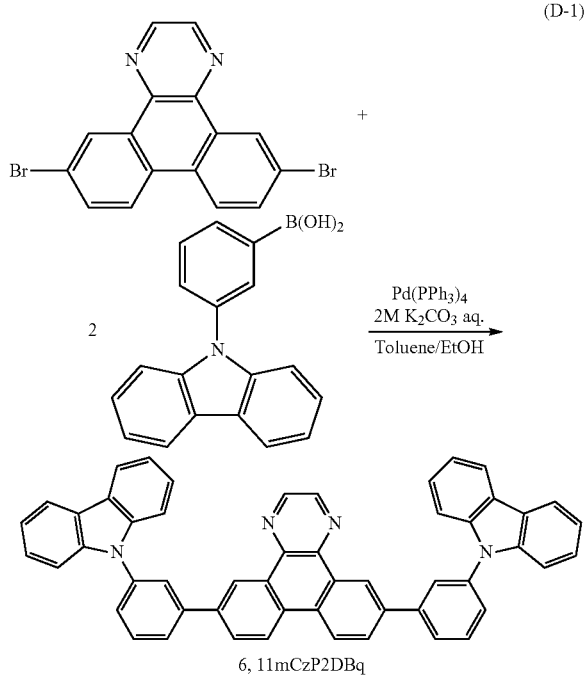

(D-1)

6,11mCzP2DBq

In a 100-mL three-neck flask were put 1.1 g (2.8 mmol) of 6,11-dibromodibenzo[f,h]quinoxaline, 1.7 g (5.9 mmol) of 3-(9H-carbazol-9-yl)phenylboronic acid, 56 mL of toluene, 6 mL of ethanol, and 4 mL of a 2M aqueous solution of potassium carbonate. The mixture was degassed by being stirred under reduced pressure, and the air in the flask was replaced with nitrogen. To this mixture was added 64 mg (0.06 mmol) of tetrakis(triphenylphosphine)palladium(0). The mixture was stirred under a nitrogen stream at 80° C. for 8 hours. After the reaction, the precipitated solid was separated by filtration to give a white solid. A toluene solution of the obtained solid was suction-filtered through alumina and Celite, and the filtrate was concentrated to give a white solid. The obtained solid was recrystallized from toluene to give a white solid. The obtained solid was washed with ethanol under the irradiation with ultrasonic waves. The solid was collected by suction filtration to give 1.1 g of powder in a yield of 55%.

By a train sublimation method, 0.84 g of the obtained powder was purified. In the purification, the powder was heated at 365° C. under a pressure of 4.2 Pa with a flow rate of argon gas of 5.0 mL/min. After the purification, 0.84 g of white powder, which was the objective substance, was obtained in a yield of 76%.

This compound was identified as 6,11mCzP2DBq, which was the objective substance, by nuclear magnetic resonance (NMR) spectroscopy.

$^1$H NMR data of the obtained substance are as follows: $^1$H NMR (CDCl$_3$, 500 MHz): δ (ppm)=7.32 (t, J=6.9 Hz, 4H), 7.45 (t, J=7.2 Hz, 4H), 7.53 (d, J=8.1 Hz, 4H), 7.64 (d, J=8.0 Hz, 2H), 7.78 (t, J=7.8 Hz, 2H), 8.01 (d, J=7.5 Hz, 2H), 8.09 (s, 2H), 8.13 (dd, J=8.6, 2.3 Hz, 2H), 8.19 (d, 7.5 Hz, 4H), 8.76 (d, J=8.6 Hz, 2H), 8.92 (s, 2H), 9.56 (d, 2.3 Hz, 2H).

Figure 20A:
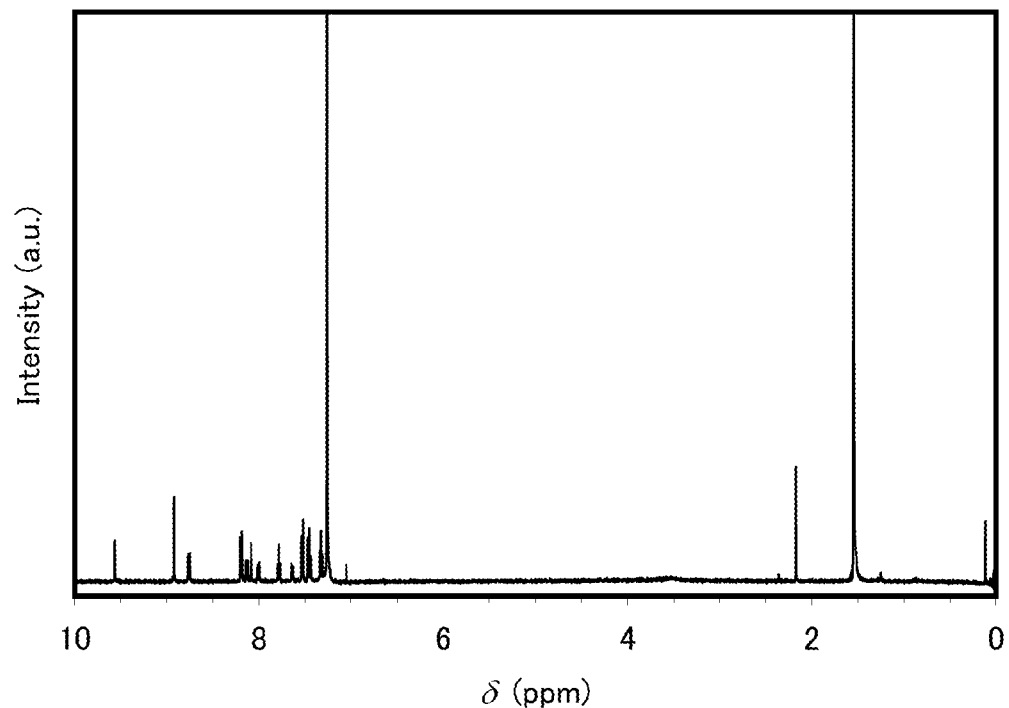
FIGS. 20A and 20B show $^1$H NMR charts of 6,11-bis[3-(9H-carbazol-9-yl)phenyl]dibenzo[f,h]quinoxaline (abbreviation: 6,11 mCzP2DBq).
Figure 20B:
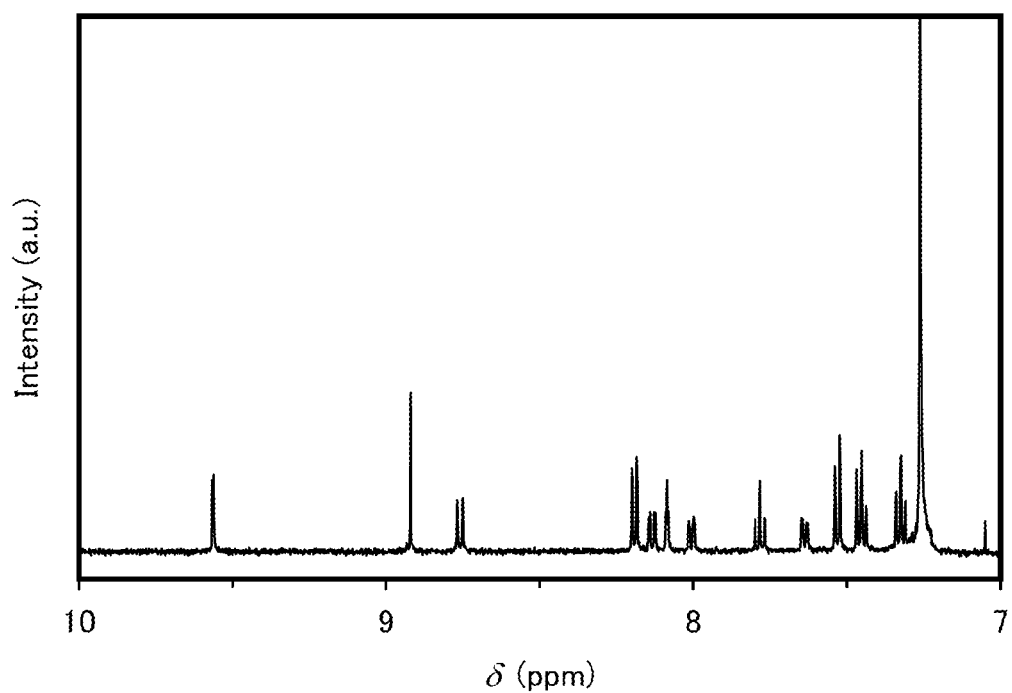

FIGS. 20A and 20B are $^1$H NMR charts. Note that FIG. 20B is a chart showing an enlarged part of FIG. 20A in the range of 7.00 ppm to 10.0 ppm.

Figure 21A:
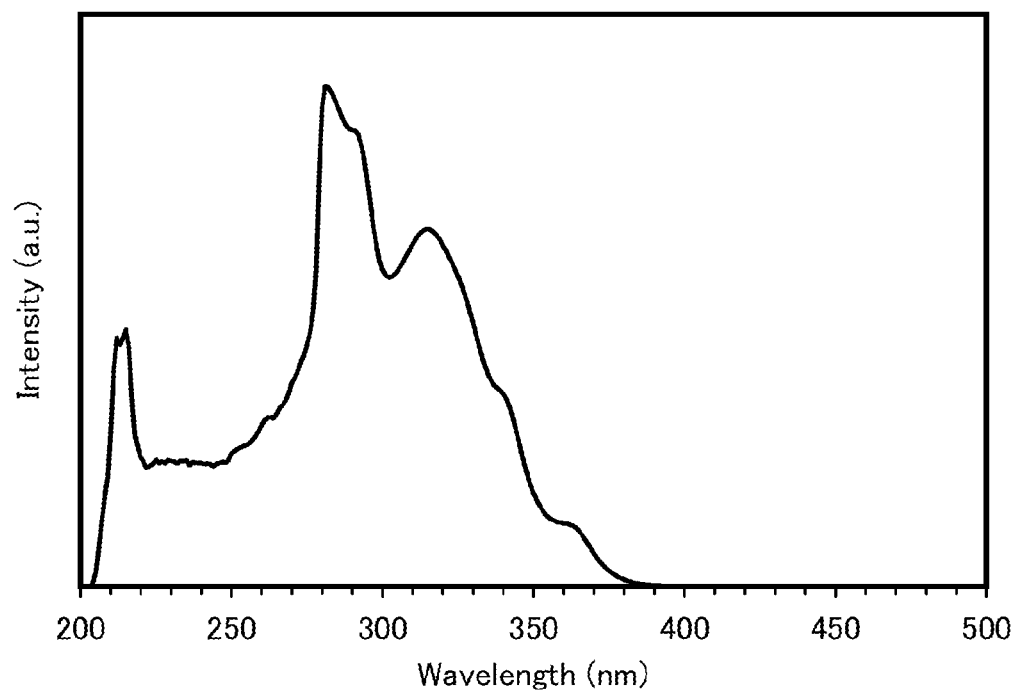
FIGS. 21A and 21B show an absorption spectrum and an emission spectrum of a toluene solution of 6,11mCzP2DBq.
Figure 21B:
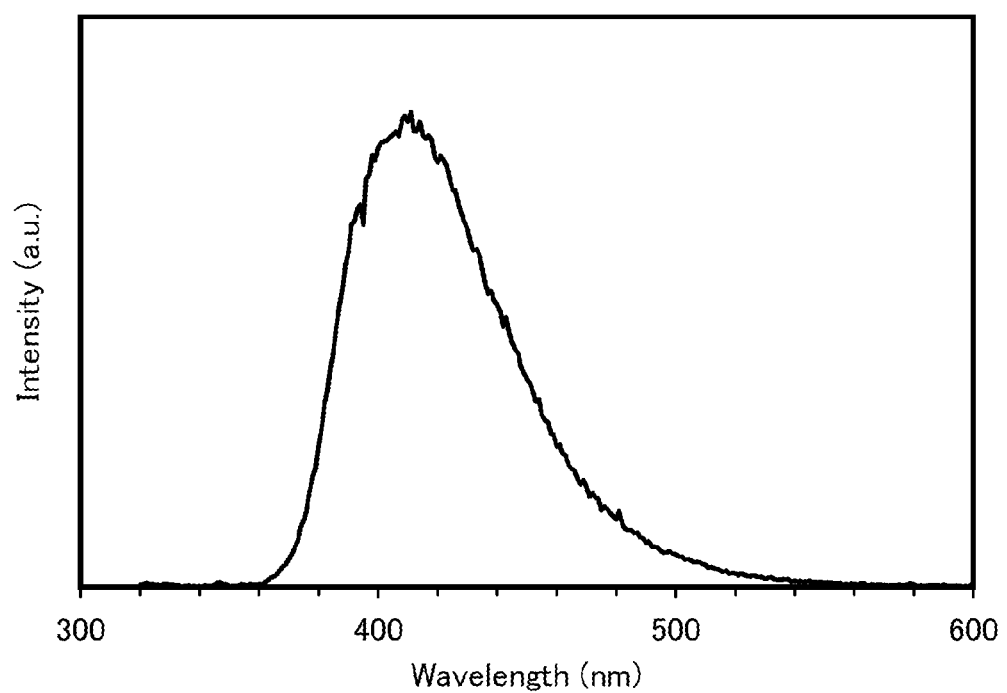
Figure 22A:
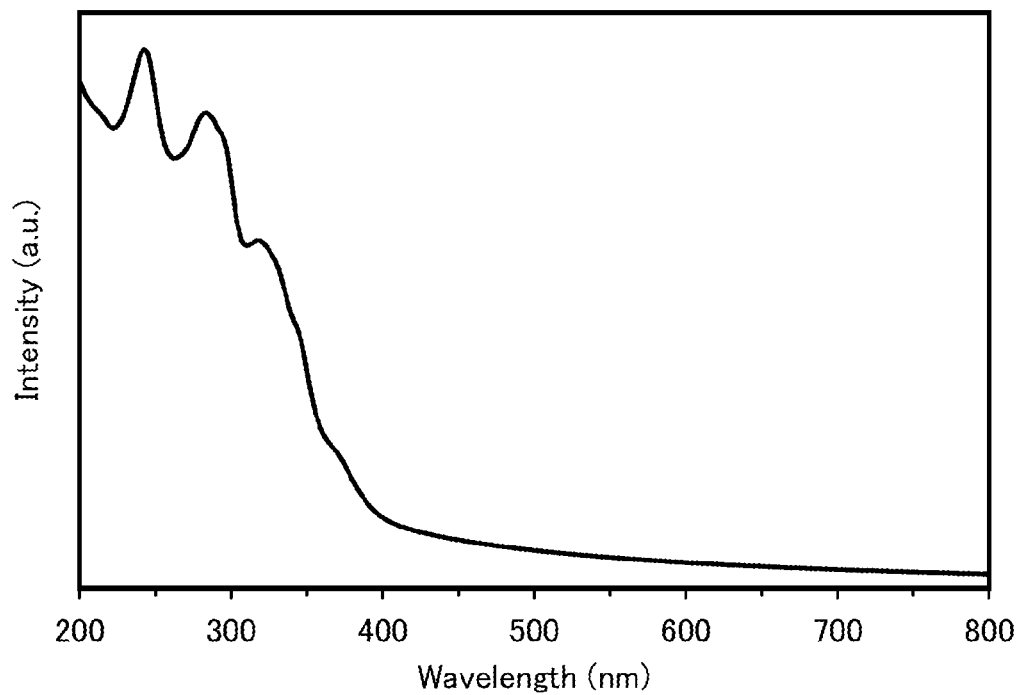
FIGS. 22A and 22B show an absorption spectrum and an emission spectrum of a thin film of 6,11mCzP2DBq.
Figure 22B:
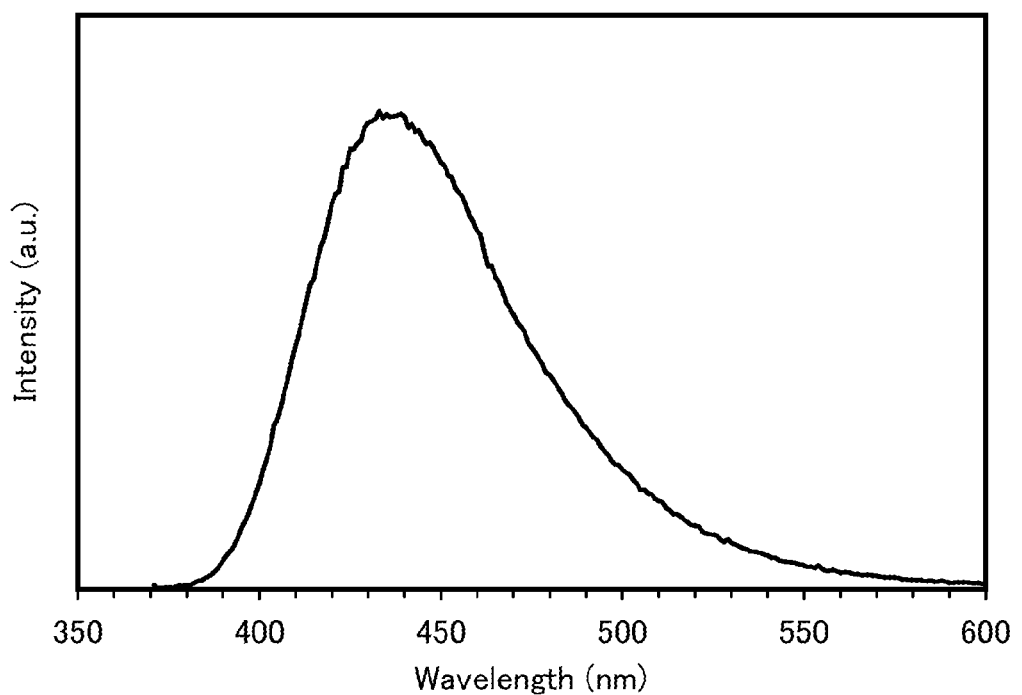

FIG. 21A shows an absorption spectrum of a toluene solution of 6,11mCzP2DBq, and FIG. 21B shows an emission spectrum thereof. FIG. 22A shows an absorption spectrum of a thin film of 6,11mCzP2DBq, and FIG. 22B shows an emission spectrum thereof. The absorption spectra were obtained in the same manner as Example 1. In FIGS. 21A and 21B and FIGS. 22A and 22B, the horizontal axis represents wavelength (nm) and the vertical axis represents intensity (arbitrary unit). In the case of the toluene solution, an absorption peak was observed at 315 nm, and an emission wavelength peak was 411 nm (at an excitation wavelength of 315 nm). In the case of the thin film, an absorption peak was observed at 367 nm, and an emission wavelength peak was 434 nm (at an excitation wavelength of 369 nm).

Further, electrophysical properties of a thin film of 6,11mCzP2DBq were evaluated (the measuring instrument was AC-2 produced by Riken Keiki, Co., Ltd.). Note that the measurement of electrophysical properties of the thin film was carried out in the same manner as Example 1.

From the results of the evaluation of electrophysical properties of the thin film, the HOMO level, the LUMO level, and the band gap (Bg) were found to be −5.93 eV, −2.80 eV, and 3.13 eV, respectively.

The above results reveal that 6,11mCzP2DBq has a relatively deep HOMO level, a relatively shallow LUMO level, and a relatively wide Bg.

Electrochemical characteristics and electrophysical properties of a 6,11mCzP2DBq solution were also evaluated.

As a measuring method, cyclic voltammetry (CV) measurement was employed. An electrochemical analyzer (ALS model 600A or 600C, produced by BAS Inc.) was used for the measurement.

The HOMO level was found to be −5.88 eV, indicating that 6,11mCzP2DBq can efficiently inject holes into a material having a HOMO level which is close to this value. Further, since the HOMO level is deep (the value thereof is small), it is found that 6,11mCzP2DBq can efficiently inject holes into a material having a shallower HOMO level (a larger value) than 6,11mCzP2DBq.

The LUMO level was found to be −2.91 eV, indicating that 6,11mCzP2DBq can efficiently inject electrons into a material having a LUMO level which is close to this value. Further, since the LUMO level is shallow (the value thereof is large), it is found that 6,11mCzP2DBq can efficiently inject electrons into a material having a deeper LUMO level (a smaller value) than 6,11mCzP2DBq. In addition, the intensity of the reduction peak was almost constant even after 100 cycles. This indicates that 6,11mCzP2DBq has tolerance to the repetition of the reduction and the oxidation between a reduced state and a neutral state.

The above cyclic voltammetry (CV) measurement was performed in a manner similar to that in Example 1. For the measurement of the oxidation characteristics of the compound of this example, the potential of a working electrode with respect to a reference electrode was scanned from 0.05 V to 1.05 V, and then from 1.05 V to 0.05 V. For the measurement of the reduction characteristics of the compound of this example, the potential of the working electrode with respect to the reference electrode was scanned from −1.4 V to −2.2 V, and then from −2.2 V to −1.4 V.

The above results suggest that 6,11mCzP2DBq, which is a heterocyclic compound according to one embodiment of the present invention, is a bipolar compound which transports both holes and electrons.

Next, 6,11mCzP2DBq obtained in this example was subjected to mass (MS) analysis by liquid chromatography mass spectrometry (LC/MS).

Figure 31A:
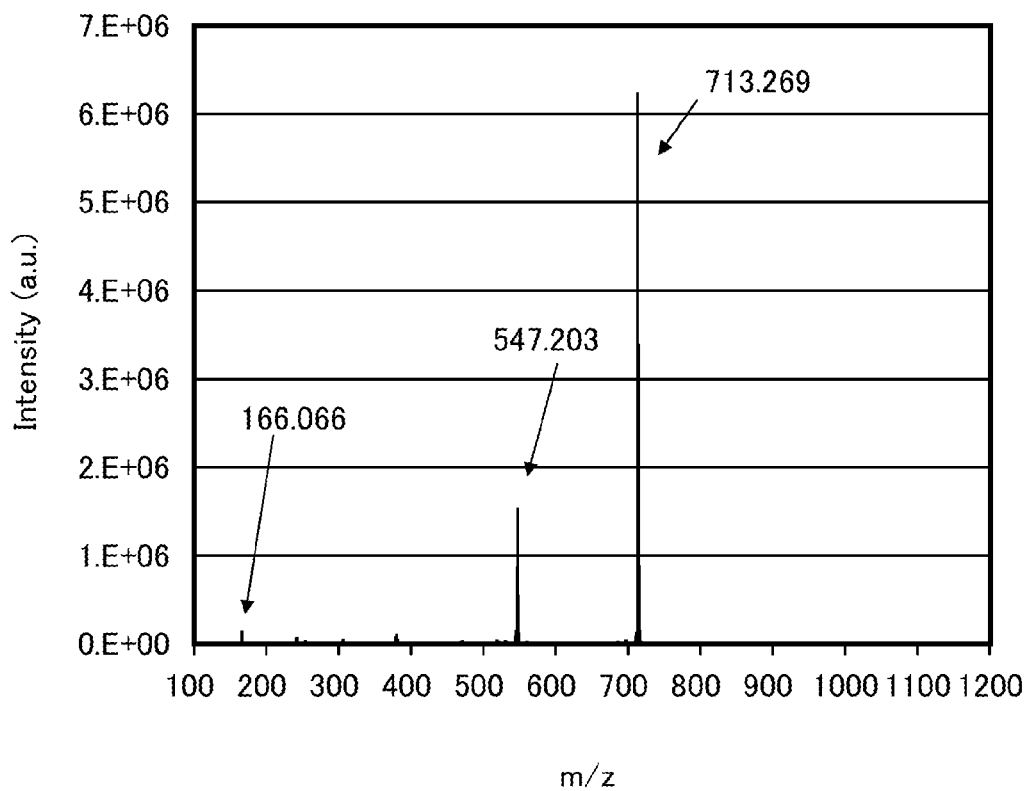
FIGS. 31A and 31B show results of LC/MS analysis of 6,11mCzP2DBq.
Figure 31B:
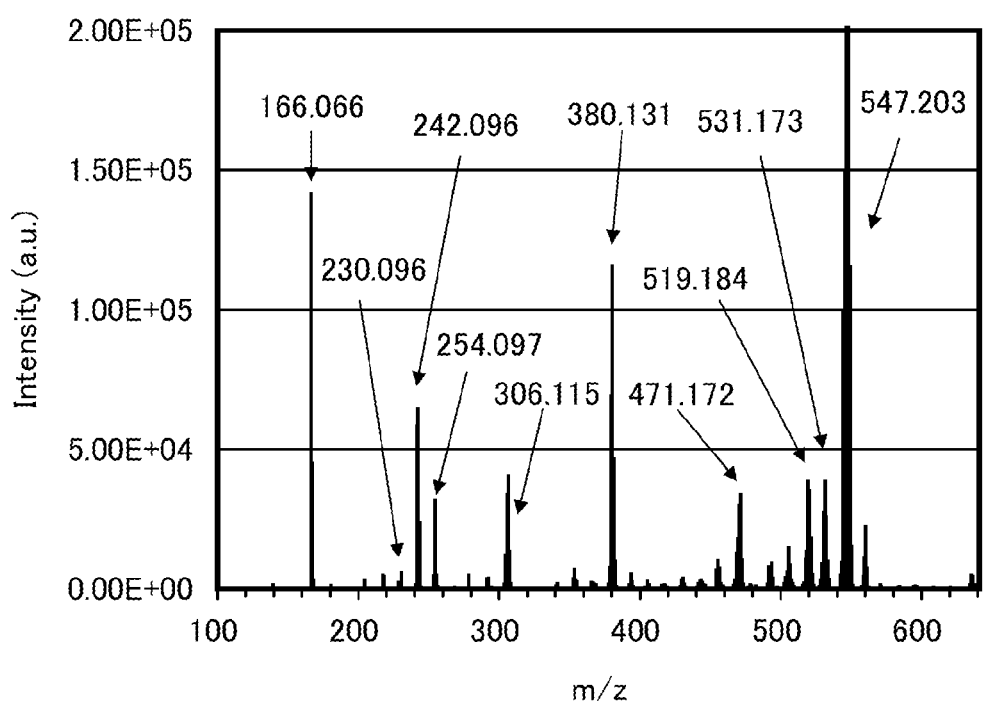

The analysis by LC/MS was carried out with Acquity UPLC (manufactured by Waters Corporation), and Xevo G2 T of MS (manufactured by Waters Corporation). In the MS analysis, ionization was carried out by an electrospray ionization (ESI) method. Capillary voltage and sample cone voltage were set to 3.0 kV and 30 V, respectively. Detection was performed in a positive mode. A component which underwent the ionization under the above conditions was collided with an argon gas in a collision cell to dissociate into product ions. Energy (collision energy) for the collision with argon was 70 eV. The mass range for the analysis was m/z=100 to 1200. FIGS. 31A and 31B show the results of the analysis.

The results in FIGS. 31A and 31B show that, owing to the presence and absence of hydrogen ions and isotopes, a plurality of product ions of 6,11mCzP2DBq are detected mainly around m/z 547, m/z 531, m/z 519, m/z 471, m/z 380, m/z 306, m/z 254, m/z 242, m/z 230, and m/z 166. The results in FIGS. 31A and 31B are characteristically derived from 6,11mCzP2DBq and thus can be regarded as important data in identification of 6,11mCzP2DBq contained in a mixture.

The product ions around m/z 166 are presumed to be carbazolyl groups, and the product ions around m/z 242 are presumed to be ions in a state where a phenylene group and a carbazolyl group are bonded, each of which matches one of features of the heterocyclic compound according to one embodiment of the present invention that includes a carbazolyl group. The product ions around m/z 547 and the product ions around m/z 380 are presumed, respectively, to be ions in a state where one carbazolyl group is removed from 6,11mCzP2DBq and ions in a state where two carbazolyl groups are removed from 6,11mCzP2DBq; accordingly, it can be confirmed that 6,11mCzP2DBq has two carbazolyl groups. The product ions around m/z 471 are presumed to be ions in a state where one phenyl group and one carbazolyl group are removed from 6,11mCzP2DBq, and the product ions around m/z 306 are presumed to be ions in a state where another carbazolyl group is further removed therefrom.

The product ions around m/z 230 are presumed to be derived from a diazatriphenylenyl group such as a dibenzo[f,h]quinoxaline ring, which proves that 6,11 mCzP2DBq, which is a heterocyclic compound according to one embodiment of the present invention, includes a dibenzo[f,h]quinoxaline ring.

EXAMPLE 4

Synthesis Example 3

This example shows a method of synthesizing 7,10-bis[3-(9H-carbazol-9-yl)phenyl]dibenzo[f,h]quinoxaline (abbreviation: 7,10mCzP2DBq) represented by the following structural formula (132).

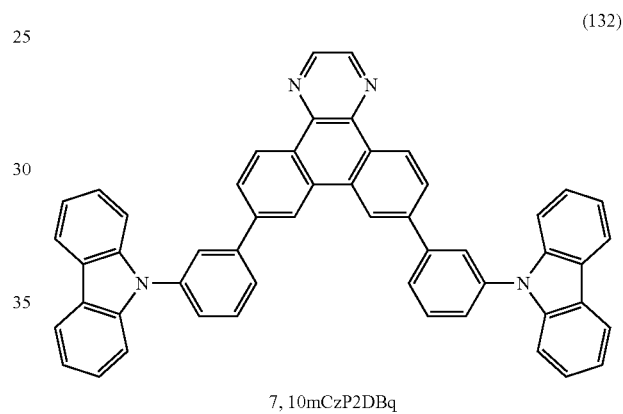

7,10mCzP2DBq (132)

Synthesis of 7,10mCzP2DBq

A scheme for the synthesis of 7,10mCzP2DBq is illustrated in (E-1).

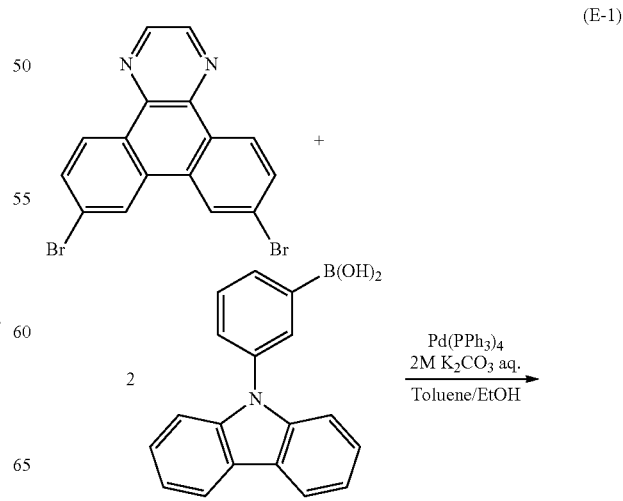

(E-1)

-continued

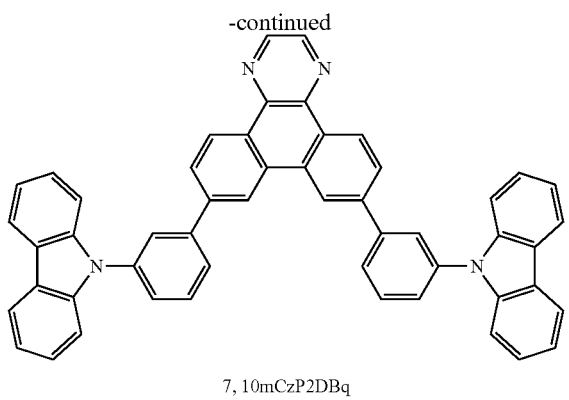

7,10mCzP2DBq

In a 100-mL three-neck flask were put 0.94 g (2.4 mmol) of 7,10-dibromodibenzo[f,h]quinoxaline, 1.5 g (5.2 mmol) of 3-(9H-carbazol-9-yl)phenylboronic acid, 56 mL of toluene, 6 mL of ethanol, and 4 mL of a 2M aqueous solution of potassium carbonate. The mixture was degassed by being stirred under reduced pressure, and the air in the flask was replaced with nitrogen. To this mixture was added 64 mg (0.06 mmol) of tetrakis(triphenylphosphine)palladium(0). The mixture was stirred under a nitrogen stream at 80° C. for 8 hours. After the reaction, the precipitated solid was separated by filtration to give a white solid. The solid was dissolved in toluene, and the toluene solution was suction-filtered through alumina and Celite, and the filtrate was concentrated to give a white solid. The obtained solid was recrystallized from toluene to give a white solid. The obtained solid was washed with ethanol under the irradiation with ultrasonic waves. The solid was collected by suction filtration to give 0.75 g of powder in a yield of 44%.

By a train sublimation method, 0.75 g of the obtained powder was purified. In the purification, the powder was heated at 330° C. under a pressure of 4.2 Pa with a flow rate of argon gas of 5.0 mL/min. After the purification, 0.54 g of white powder, which was the objective substance, was obtained in a yield of 72%.

This compound was identified as 7,10mCzP2DBq, which was the objective substance, by nuclear magnetic resonance (NMR) spectroscopy.

$^1$H NMR data of the obtained substance are as follows: $^1$H NMR (CDCl$_3$, 500 MHz): δ (ppm)=7.23-7.29 (m, 4H), 7.42 (t, J=7.5 Hz, 4H), 7.54 (d, J=8.0 Hz, 4H), 7.66 (d, J=8.6 Hz, 2H), 7.79 (t, J=8.1 Hz, 2H), 7.93 (d, J=7.5 Hz, 2H), 8.03-8.07 (m, 4H), 8.18 (d, J=7.5 Hz, 4H), 8.94-8.95 (m, 4H), 9.35 (d, J=8.1 Hz, 2H).

Figure 23A:
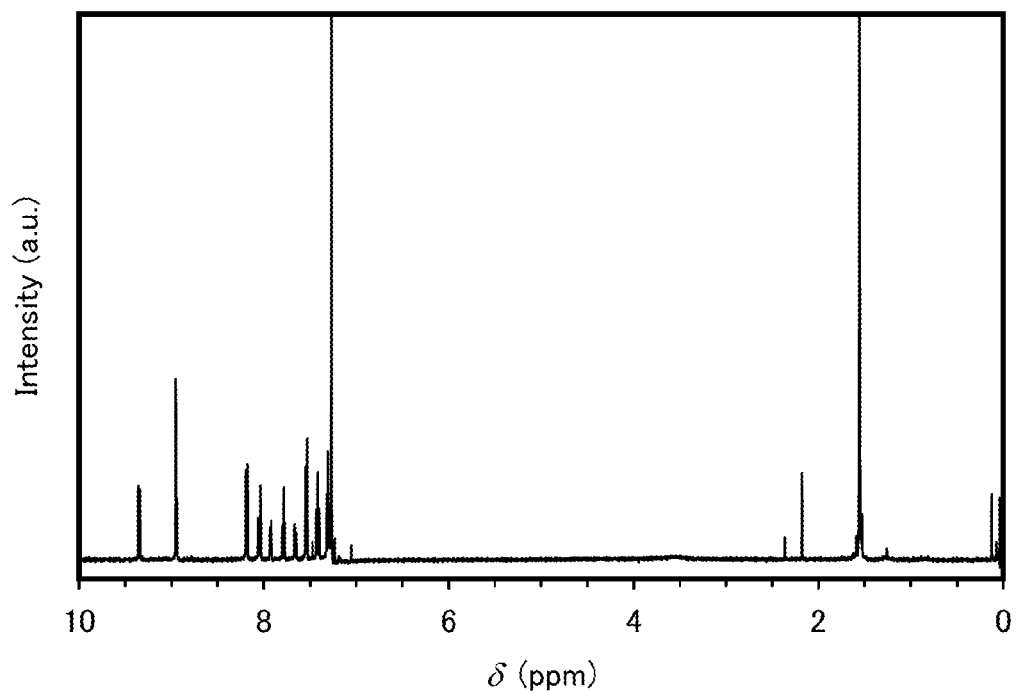
FIGS. 23A and 23B show $^1$H NMR charts of 7,10-bis[3-(9H-carbazol-9-yl)phenyl]dibenzo[f,h]quinoxaline (abbreviation: 7,10mCzP2DBq).
Figure 23B:
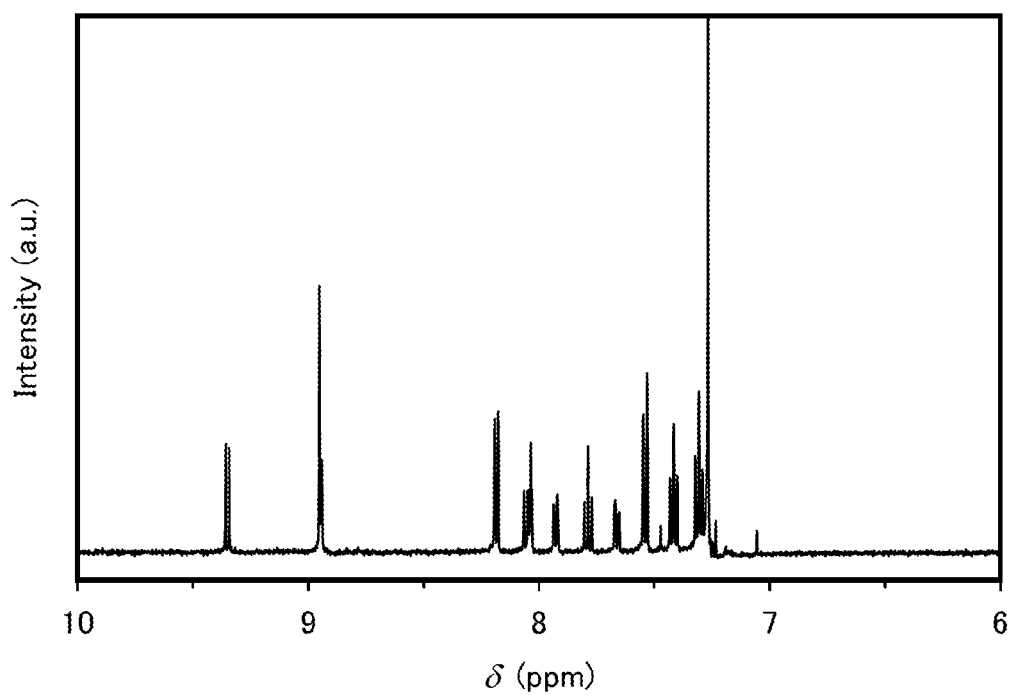

FIGS. 23A and 23B are $^1$H NMR charts. Note that FIG. 23B is a chart showing an enlarged part of FIG. 23A in the range of 6.00 ppm to 10.0 ppm.

Figure 24A:
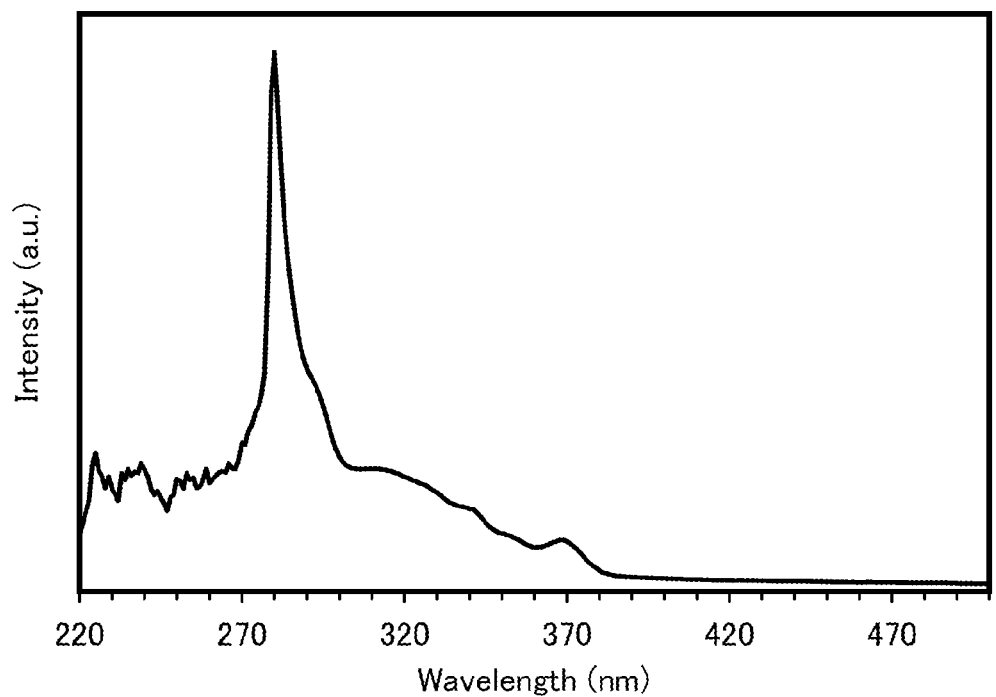
FIGS. 24A and 24B show an absorption spectrum and an emission spectrum of a toluene solution of 7,10mCzP2DBq.
Figure 24B:
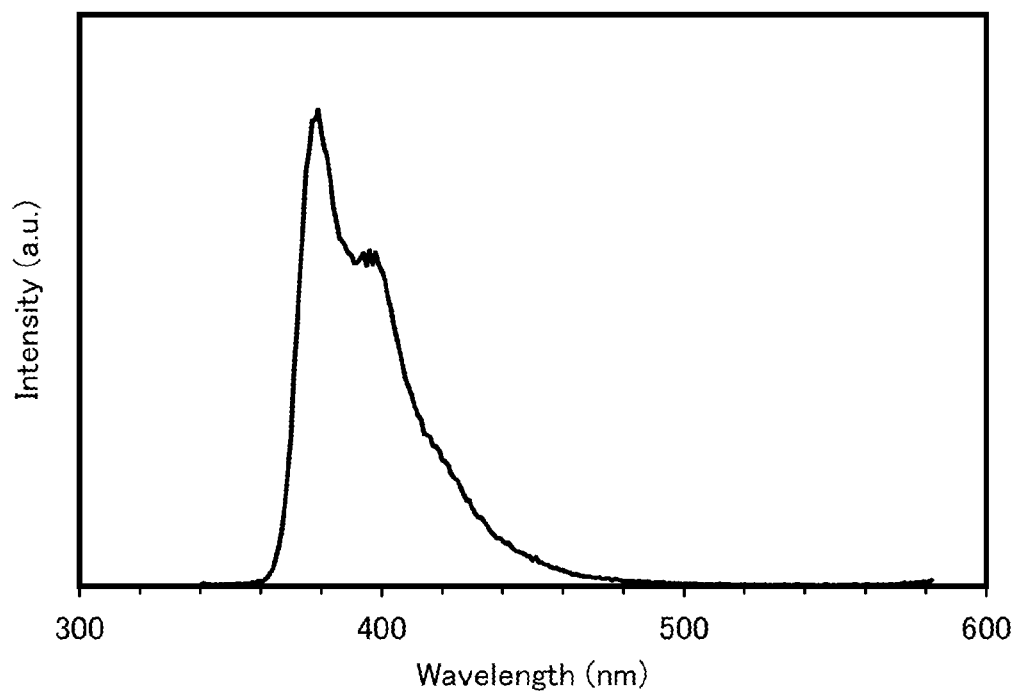
Figure 25A:
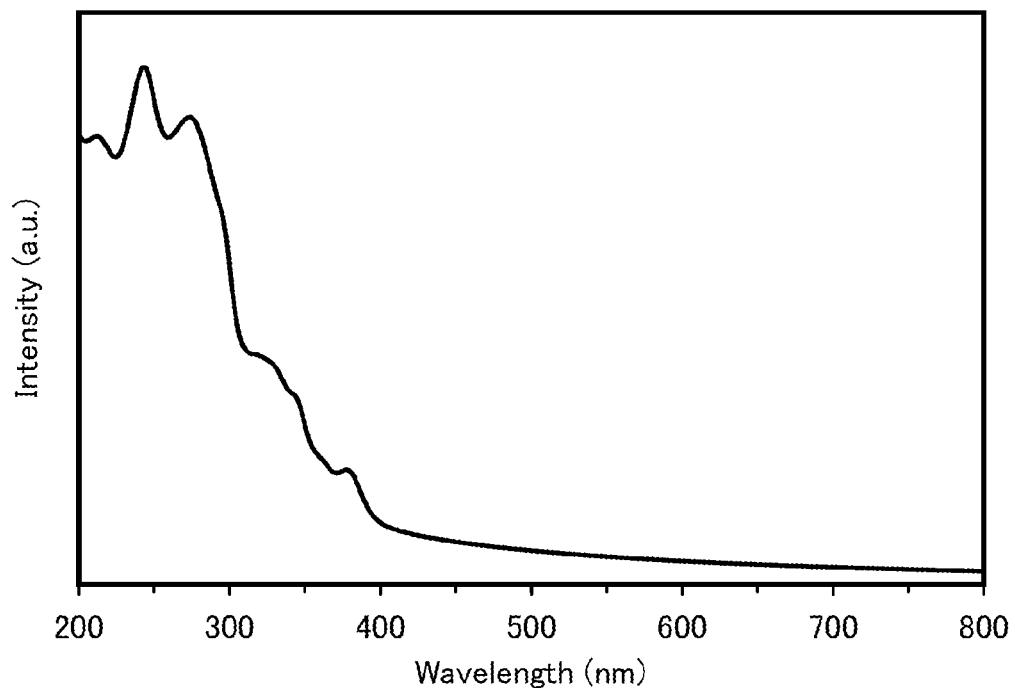
FIGS. 25A and 25B show an absorption spectrum and an emission spectrum of a thin film of 7,10mCzP2DBq.
Figure 25B:
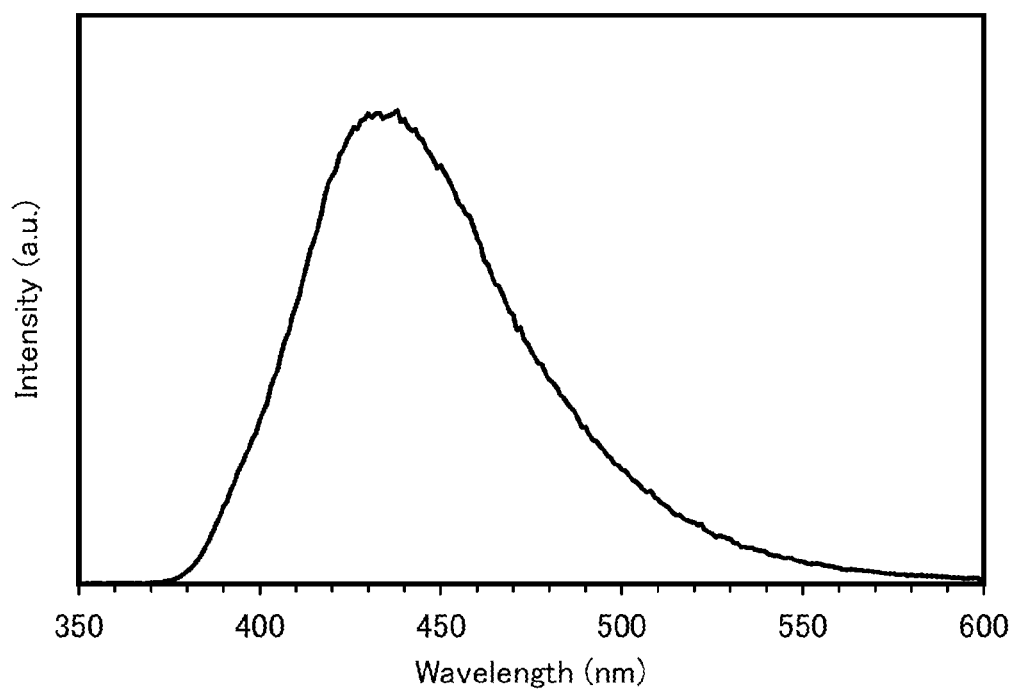

FIG. 24A shows an absorption spectrum of a toluene solution of 7,10mCzP2DBq, and FIG. 24B shows an emission spectrum thereof. FIG. 25A shows an absorption spectrum of a thin film of 7,10mCzP2DBq, and FIG. 25B shows an emission spectrum thereof. The absorption spectra were obtained in the same manner as Example 1. In FIGS. 24A and 24B and FIGS. 25A and 25B, the horizontal axis represents wavelength (nm) and the vertical axis represents intensity (arbitrary unit). In the case of the toluene solution, an absorption peak was observed at 369 nm, and an emission wavelength peak was 379 nm (at an excitation wavelength of 369 nm). In the case of the thin film, an absorption peak was observed at 378 nm, and an emission wavelength peak was 432 nm (at an excitation wavelength of 342 nm).

Further, electrophysical properties of a thin film of 7,10mCzP2DBq were evaluated (the measuring instrument was AC-2 produced by Riken Keiki, Co., Ltd.). Note that the measurement of electrophysical properties of the thin film was carried out in the same manner as Example 1.

From the results of the measurement of electrophysical properties of the thin film, the HOMO level, the LUMO level, and the band gap (Bg) were found to be −5.93 eV, −2.82 eV, and 3.11 eV, respectively.

The above results reveal that 7,10mCzP2DBq has a relatively deep HOMO level, a relatively shallow LUMO level, and a relatively wide Bg.

Electrochemical characteristics and electrophysical properties of a 7,10mCzP2DBq solution were also evaluated.

As a measuring method, cyclic voltammetry (CV) measurement was employed. An electrochemical analyzer (ALS model 600A or 600C, produced by BAS Inc.) was used for the measurement.

The HOMO level was found to be −5.86 eV, indicating that 7,10mCzP2DBq can efficiently inject holes into a material having a HOMO level which is close to this value. Further, since the HOMO level is deep (the value thereof is small), it is found that 7,10mCzP2DBq can efficiently inject holes into a material having a shallower HOMO level (a larger value) than 7,10mCzP2DBq.

The LUMO level was found to be −2.91 eV, indicating that 7,10mCzP2DBq can efficiently inject electrons into a material having a LUMO level which is close to this value. Further, since the LUMO level is shallow (the value thereof is large), it is found that 7,10mCzP2DBq can efficiently inject electrons into a material having a deeper LUMO level (a smaller value) than 7,10mCzP2DBq. In addition, the intensity of the reduction peak was almost constant even after 100 cycles. This indicates that 7,10mCzP2DBq has tolerance to the repetition of the reduction and the oxidation between a reduced state and a neutral state.

The above cyclic voltammetry (CV) measurement was performed in a manner similar to that in Example 1. For the measurement of the oxidation characteristics of the compound of this example, the potential of a working electrode with respect to a reference electrode was scanned from −0.12 V to 1.05 V, and then from 1.05 V to −0.12 V. For the measurement of the reduction characteristics of the compound of this example, the potential of the working electrode with respect to the reference electrode was scanned from −1.3 V to −2.1 V, and then from −2.1 V to −1.3 V.

The above results suggest that 7,10mCzP2DBq, which is a heterocyclic compound according to one embodiment of the present invention, is a bipolar compound which transports both holes and electrons.

Figure 32A:
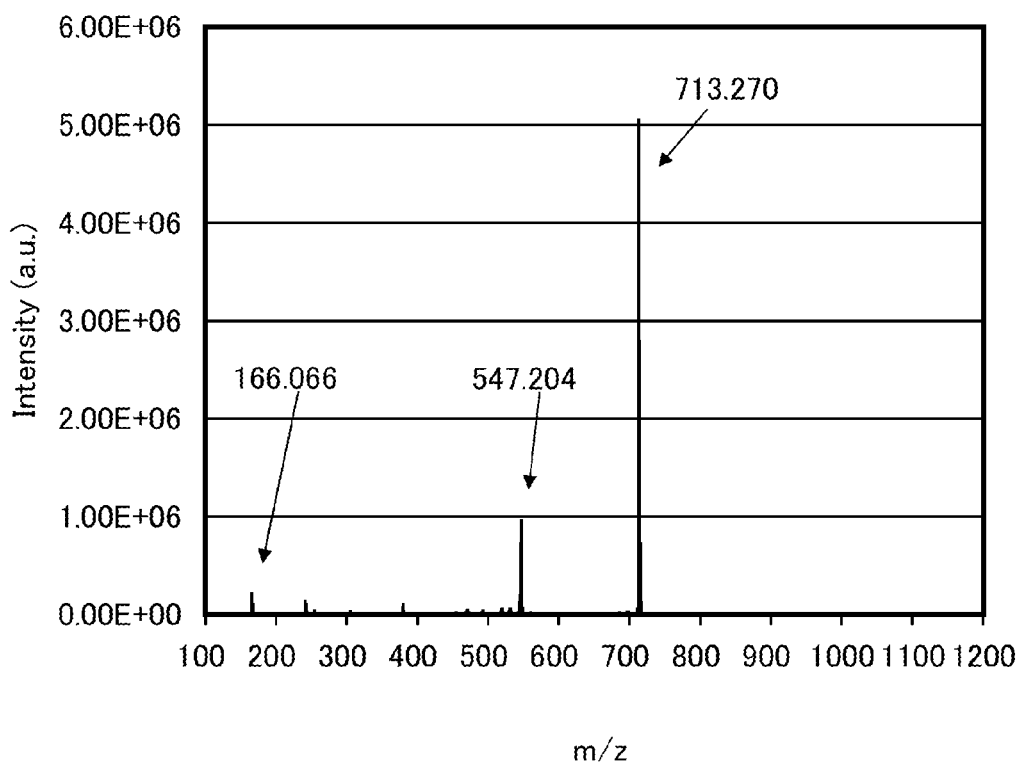
FIGS. 32A and 32B show results of LC/MS analysis of 7,10mCzP2DBq.
Figure 32B:
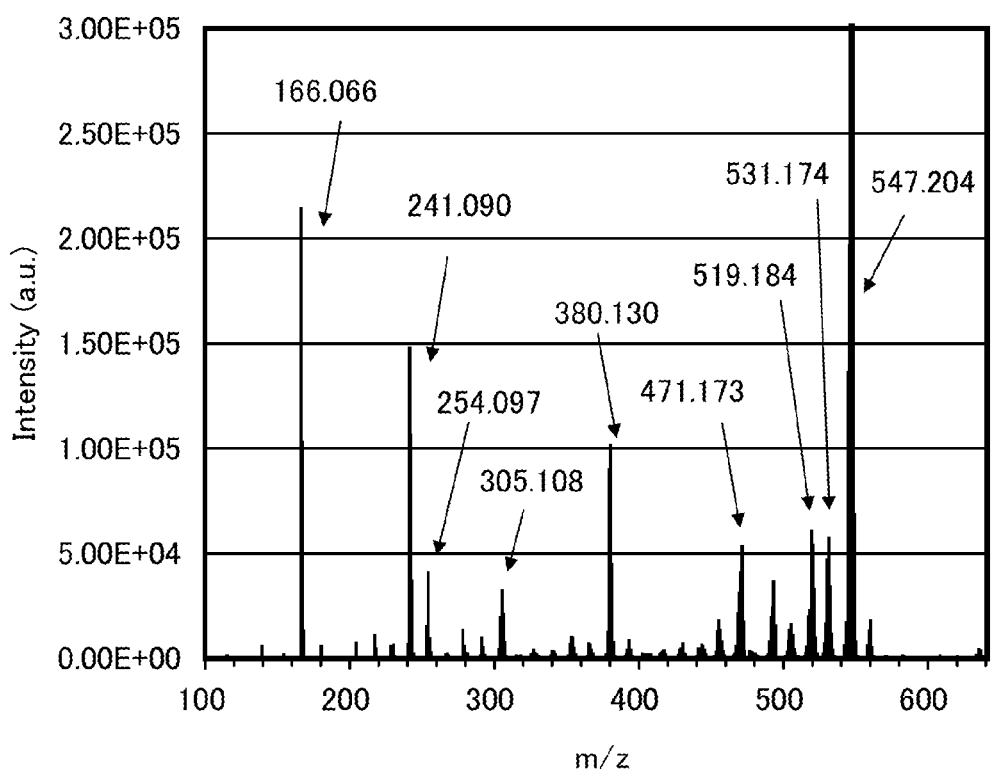

Next, 7,10mCzP2DBq obtained in this example was subjected to mass (MS) analysis by LC/MS. Methods, conditions, and the like for the analysis by LC/MS were the same as those in Example 3. FIGS. 32A and 32B show the results of the measurement.

The results in FIGS. 32A and 32B show that, owing to the presence and absence of hydrogen ions and isotopes, a plurality of product ions of 7,10mCzP2DBq are detected mainly around m/z 547, m/z 531, m/z 519, m/z 471, m/z 380, m/z 305, m/z 254, m/z 241, and m/z 166. The results in FIGS. 32A and 32B are characteristically derived from 7,10mCzP2DBq and thus can be regarded as important data in identification of 7,10mCzP2DBq contained in a mixture.

The product ions around m/z 166 are presumed to be carbazolyl groups, and the product ions around m/z 241 are presumed to be cations in a state where a phenylene group and a carbazolyl group are bonded, each of which matches one of features of the heterocyclic compound according to one embodiment of the present invention that includes a carbazolyl group. The product ions around m/z 547 and the product ions around m/z 380 are presumed, respectively, to be ions in a state where one carbazolyl group is removed from 7,10mCzP2DBq and ions in a state where two carbazolyl groups are removed from 7,10mCzP2DBq; accordingly, it can be confirmed that 7,10mCzP2DBq has two carbazolyl groups. The product ions around m/z 471 are presumed to be ions in a state where one phenyl group and one carbazolyl group are removed from 7,10mCzP2DBq, and the product ions around m/z 305 are presumed to be ions in a state where another carbazolyl group is further removed therefrom.

EXAMPLE 5

In this example, a light-emitting element according to one embodiment of the present invention is described with reference to FIG. 13. Chemical formulae of materials used in this example are shown below. Note that the chemical formulae of the materials which are described above are omitted.

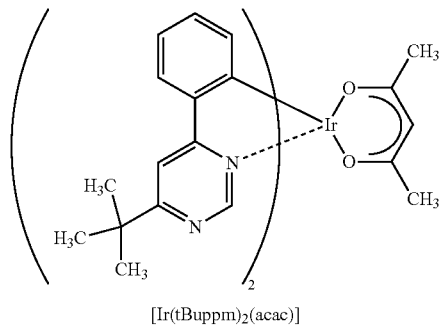

[Ir(tBuppm)$_2$(acac)]

The following shows a method of fabricating light-emitting elements 3 to 6 of this example.

(Light-Emitting Element 3)

The light-emitting layer 1113 of the light-emitting element 3 was formed by co-evaporation of 6,11mCzP2DBq which was synthesized in Example 3, PCBA1BP, and (acetylacetonato)bis(6-tert-butyl-4-phenylpyrimidinato)iridium(III) (abbreviation: [Ir(tBuppm)$_2$(acac)]). Here, a 15-nm-thick layer formed with the weight ratio of 6,11mCzP2DBq to PCBA1BP and [Ir(tBuppm)$_2$(acac)] adjusted to 0.7:0.3:0.05 (=6,11mCzP2DBq:PCBA1BP:[Ir(tBuppm)$_2$(acac)]) and a 25-nm-thick layer formed with the weight ratio of 6,11mCzP2DBq to PCBA1BP and [Ir(tBuppm)$_2$(acac)] adjusted to 0.8:0.2:0:05 (=6,11mCzP2DBq:PCBA1BP:[Ir(tBuppm)$_2$(acac)]) were stacked.

A 6,11mCzP2DBq film was formed to a thickness of 10 nm, whereby the first electron-transport layer 1114a was formed. The components other than the light-emitting layer 1113 and the first electron-transport layer 1114a were formed in the same manner as those of the light-emitting element 1.

(Light-Emitting Element 4)

The light-emitting layer 1113 of the light-emitting element 4 was formed by co-evaporation of 7,10mCzP2DBq which was synthesized in Example 4, PCBA1BP, and [Ir(tBuppm)$_2$(acac)]. Here, a 15-nm-thick layer formed with the weight ratio of 7,10mCzP2DBq to PCBA1BP and [Ir(tBuppm)$_2$(acac)] adjusted to 0.7:0.3:0.05 (=7,10mCzP2DBq:PCBA1BP:[Ir(tBuppm)$_2$(acac)]) and a 25-nm-thick layer formed with the weight ratio of 7,10mCzP2DBq to PCBA1BP and [Ir(tBuppm)$_2$(acac)] adjusted to 0.8:0.2:0:05 (=7,10mCzP2DBq:PCBA1BP:[Ir(tBuppm)$_2$(acac)]) were stacked.

A 7,10mCzP2DBq film was formed to a thickness of 10 nm, whereby the first electron-transport layer 1114a of the light-emitting element 4 was formed. The components other than the light-emitting layer 1113 and the first electron-transport layer 1114a were formed in the same manner as those of the light-emitting element 1.

(Light-emitting Element 5)

The light-emitting layer 1113 of the light-emitting element 5 was formed by co-evaporation of 6,11mCzP2DBq and [Ir(tBuppm)$_2$(acac)]. Here, the weight ratio of 6,11mCzP2DBq to [Ir(tBuppm)$_2$(acac)] was adjusted to 1:0.05 (=6,11mCzP2DBq:[Ir(tBuppm)$_2$(acac)]). The thickness of the light-emitting layer 1113 was set to 40 nm.

A 6,11mCzP2DBq film was formed to a thickness of 10 nm, whereby the first electron-transport layer 1114a of the light-emitting element 5 was formed. The components other than the light-emitting layer 1113 and the first electron-transport layer 1114a were formed in the same manner as those of the light-emitting element 1.

(Light-Emitting Element 6)

The light-emitting layer 1113 of the light-emitting element 6 was formed by co-evaporation of 7,10mCzP2DBq and [Ir(tBuppm)$_2$(acac)]. Here, the weight ratio of 7,10mCzP2DBq to [Ir(tBuppm)$_2$(acac)] was adjusted to 1:0.05 (=7,10mCzP2DBq:[Ir(tBuppm)$_2$(acac)]). The thickness of the light-emitting layer 1113 was set to 40 nm.

A 7,10mCzP2DBq film was formed to a thickness of 10 nm, whereby the first electron-transport layer 1114a of the light-emitting element 6 was formed. The components other than the light-emitting layer 1113 and the first electron-transport layer 1114a were formed in the same manner as those of the light-emitting element 1.

Table 3 shows element structures of the light-emitting elements 3 to 6 obtained as described above.

TABLE 3

| | $1^{st}$ electrode | HIL$^a$ | HTL$^b$ | EmL$^c$ | | $1^{st}$ ETL$^d$ | $2^{nd}$ ETL$^d$ | EIL$^e$ | $2^{nd}$ electrode |
|---|---|---|---|---|---|---|---|---|---|
| | | | | $1^{st}$ EmL$^c$ | $2^{nd}$ EmL$^c$ | | | | |
| | | | | 6,11mCzP2DBq:PCBA1BP:[Ir(tBuppm)$_2$(acac)] | | | | | |
| Light-emitting element 3 | ITSO 110 nm | DBT3P-II:MoOx (4:2) 40 nm | BPAFLP 20 nm | (0.7:0.3:0.05) 15 nm | (0.8:0.2:0.05) 25 nm | 6,11mCzP2DBq 10 nm | BPhen 20 nm | LiF 1 nm | Al 200 nm |
| | | | | 7,10mCzP2DBq:PCBA1BP:[Ir(tBuppm)$_2$(acac)] | | | | | |
| Light-emitting element 4 | ITSO 110 nm | DBT3P-II:MoOx (4:2) 40 nm | BPAFLP 20 nm | (0.7:0.3:0.05) 15 nm | (0.8:0.2:0.05) 25 nm | 7,10mCzP2DBq 10 nm | BPhen 20 nm | LiF 1 nm | Al 200 nm |

TABLE 3-continued

| | 1st electrode | HIL[a] | HTL[b] | EmL[c] 1st EmL[c] | EmL[c] 2nd EmL[c] | 1st ETL[d] | 2nd ETL[d] | EIL[e] | 2nd electrode |
|---|---|---|---|---|---|---|---|---|---|
| Light-emitting element 5 | ITSO 110 nm | DBT3P-II:MoOx (4:2) 40 nm | BPAFLP 20 nm | 6,11mCzP2DBq:[Ir(tBuppm)$_2$(acac)] (1:0.05) 40 nm | | 6,11mCzP2DBq 10 nm | BPhen 20 nm | LiF 1 nm | Al 200 nm |
| Light-emitting element 6 | ITSO 110 nm | DBT3P-II:MoOx (4:2) 40 nm | BPAFLP 20 nm | | 7,10mCzP2DBq:[Ir(tBuppm)$_2$(acac)] (1:0.05) 40 nm | 7,10mCzP2DBq 10 nm | BPhen 20 nm | LiF 1 nm | Al 200 nm |

[a] Hole-injection layer.
[b] Hole-transport layer.
[c] Light-emitting layer.
[d] Electron-transport layer.
[e] Electron-injection layer.

In a glove box containing a nitrogen atmosphere, the light-emitting elements 3 to 6 were sealed with a glass substrate so as not to be exposed to the air. Then, operation characteristics of the elements were measured. Note that the measurement was carried out at room temperature (in an atmosphere kept at 25° C.).

Figure 26:
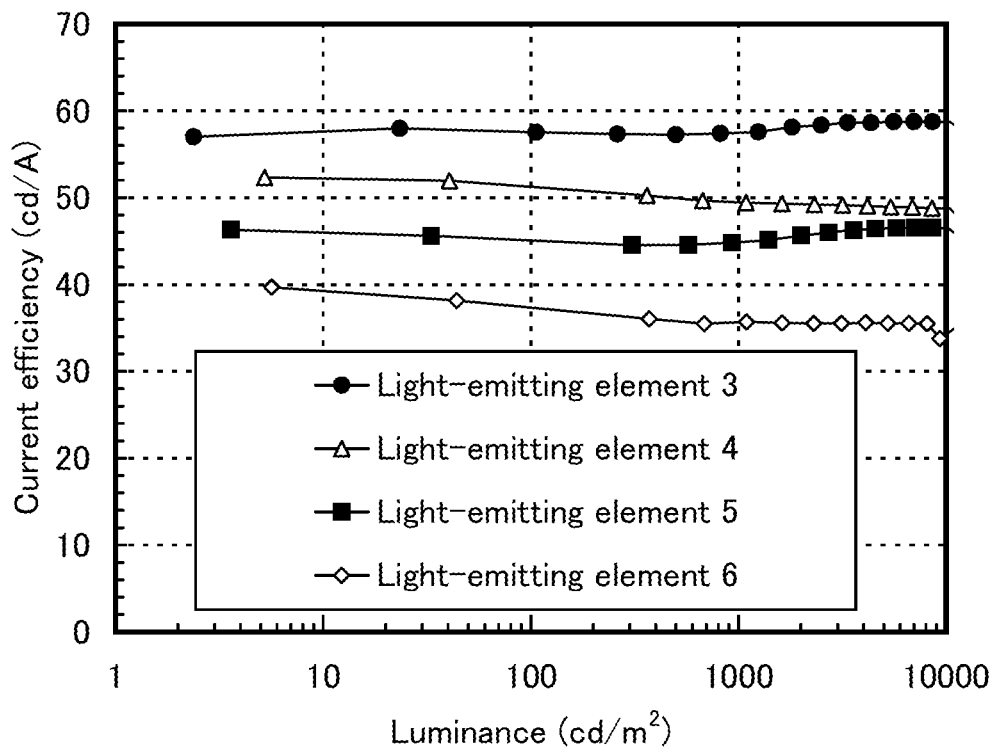
FIG. 26 shows luminance-current efficiency characteristics of light-emitting elements in Example 5.
Figure 27:
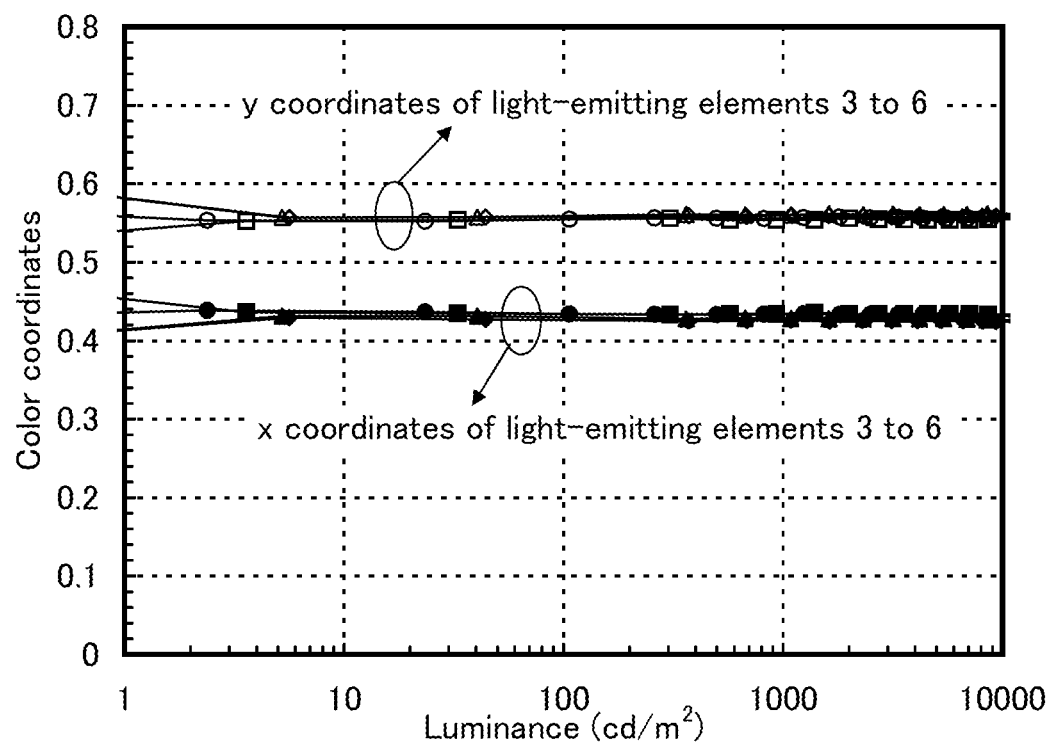
FIG. 27 shows luminance-chromaticity coordinate characteristics of the light-emitting elements in Example 5.

FIG. 26 shows luminance-current efficiency characteristics of the light-emitting elements 3 to 6. In FIG. 26, the horizontal axis represents luminance (cd/m$^2$) and the vertical axis represents current efficiency (cd/A). FIG. 27 shows the luminance-chromaticity coordinate characteristics. In FIG. 27, the horizontal axis represents luminance (cd/m$^2$) and the vertical axis represents chromaticity coordinate (the x-coordinate or the y-coordinate). Table 4 shows voltage (V), current density (mA/cm$^2$), CIE chromaticity coordinates (x, y), luminance (cd/m$^2$), current efficiency (cd/A), and external quantum efficiency (%) of each light-emitting element at a luminance of around 1000 cd/m$^2$.

TABLE 4

| | Voltage (V) | Current density (mA/cm$^2$) | Chromaticity (x, y) | Luminance (cd/m$^2$) | Current efficiency (cd/A) | External Quantum efficiency (%) |
|---|---|---|---|---|---|---|
| Light-emitting element 3 | 3.1 | 1.4 | (0.43, 0.56) | 820 | 57 | 16 |
| Light-emitting element 4 | 3.1 | 2.2 | (0.43, 0.56) | 1100 | 49 | 14 |
| Light-emitting element 5 | 3.1 | 2.1 | (0.43, 0.55) | 900 | 45 | 12 |
| Light-emitting element 6 | 3.1 | 3.1 | (0.43, 0.56) | 1100 | 36 | 10 |

Figure 28:
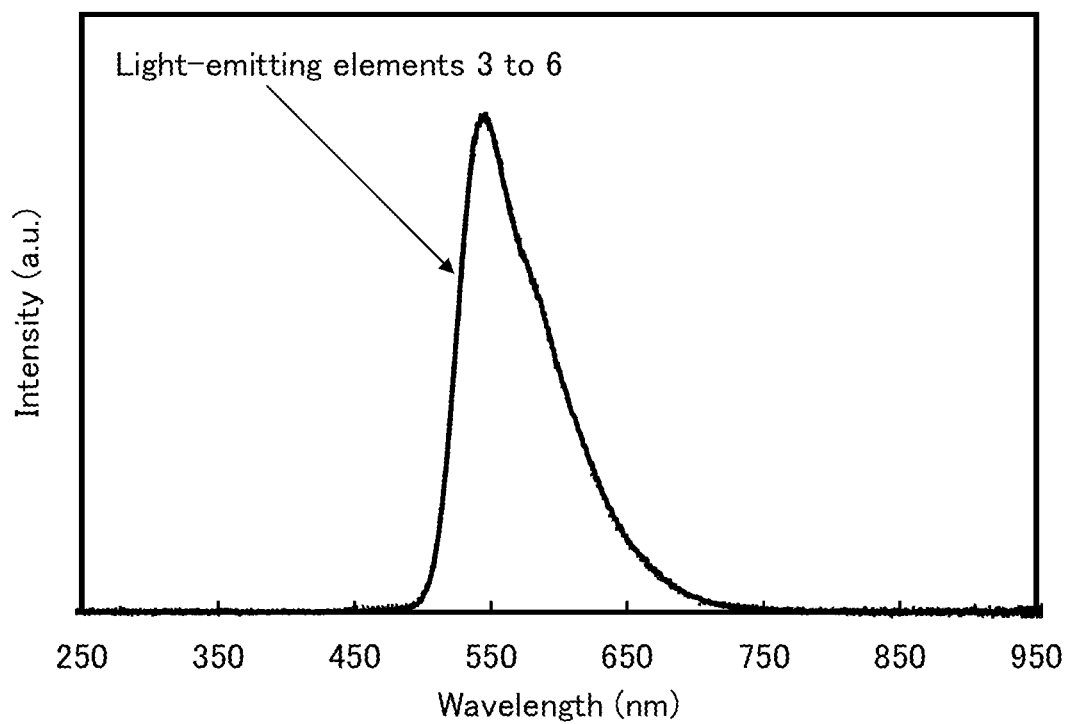
FIG. 28 shows emission spectra of the light-emitting elements in Example 5.

FIG. 28 shows emission spectra of the light-emitting elements 3 to 6, which were obtained by applying a current of 0.1 mA. In FIG. 28, the horizontal axis represents wavelength (nm) and the vertical axis represents emission intensity (arbitrary unit). As shown in FIG. 28 and Table 4, the CIE chromaticity coordinates of the light-emitting element 3 were (x, y)=(0.43, 0.56) at a luminance of 820 cd/m$^2$. The CIE chromaticity coordinates of the light-emitting element 4 were (x, y)=(0.43, 0.56) at a luminance of 1100 cd/m$^2$. The CIE chromaticity coordinates of the light-emitting element 5 were (x, y)=(0.43, 0.55) at a luminance of 900 cd/m$^2$. The CIE chromaticity coordinates of the light-emitting element 6 were (x, y)=(0.43, 0.56) at a luminance of 1100 cd/m$^2$. The light-emitting elements 3 to 6 were found to emit light originating from [Ir(tBuppm)$_2$(acac)]. This reveals that 6,11mCzP2DBq and 7,10mCzP2DBq, which are heterocyclic compounds according to embodiments of the present invention, each have a sufficiently high T1 level which enables a green phosphorescent material to emit light. Accordingly, it is found that 6,11mCzP2DBq and 7,10mCzP2DBq can each be used as a host material for green to red phosphorescent materials.

FIG. 26 and Table 4 show that the light-emitting elements 3 to 6 have high current efficiency and high external quantum efficiency and that, in particular, the light-emitting elements 3 and 4 have higher current efficiency and higher external quantum efficiency than the light-emitting elements 5 and 6. 6,11mCzP2DBq and 7,10mCzP2DBq are heterocyclic compounds in each of which two carbazole rings are bonded to a dibenzo[f,h]quinoxaline ring through respective meta-phenylene groups. Therefore, it is possible to provide a light-emitting element having high emission efficiency. The light-emitting elements 3 and 4 each contain PCBA1BP in the light-emitting layer. PCBA1BP is a material having an amine skeleton and having a high hole mobility. Therefore, carrier transfer is more efficiently performed in the light-emitting layer of the light-emitting elements 3 and 4, which leads to their higher emission efficiency than the light-emitting elements 5 and 6.

As shown in FIG. 27, the light-emitting elements 3 to 6 show substantially no change in color over a range from low luminance to high luminance. It can be said from this result that the light-emitting elements 3 to 6 are elements having excellent carrier balance.

As described above, light-emitting elements having high emission efficiency were able to be fabricated by the use of 6,11mCzP2DBq and 7,10mCzP2DBq manufactured in Examples 3 and 4 as a host material of a light-emitting layer and a material of an electron-transport layer.

EXAMPLE 6

In this example, a light-emitting element according to one embodiment of the present invention is described with reference to FIG. 13. Materials used in this example are the same as those used in the above Examples, and their chemical formulae are omitted here.

The following shows a method of fabricating light-emitting elements 7 and 8 of this example.

(Light-emitting Element 7)

The light-emitting layer 1113 of the light-emitting element 7 was formed by co-evaporation of 6,11mCzP2DBq which was synthesized in Example 3, PCBA1BP, and [Ir(dppm)$_2$(acac)]. Here, the weight ratio of 6,11mCzP2DBq to PCBA1BP and [Ir(dppm)$_2$(acac)] was adjusted to 0.8:0.2:0.05 (=6,11mCzP2DBq:PCBA1BP:[Ir(dppm)$_2$(acac)]). The thickness of the light-emitting layer 1113 was set to 40 nm.

A 6,11mCzP2DBq film was formed to a thickness of 10 nm, whereby the first electron-transport layer 1114a of the light-emitting element 7 was formed. The components other than the light-emitting layer 1113 and the first electron-transport layer 1114a were formed in the same manner as those of the light-emitting element 1.

(Light-emitting Element 8)

The light-emitting layer 1113 of the light-emitting element 8 was formed by co-evaporation of 7,10mCzP2DBq which was synthesized in Example 4, PCBA1BP, and [Ir(dppm)$_2$(acac)]. Here, the weight ratio of 7,10mCzP2DBq to PCBA1BP and [Ir(dppm)$_2$(acac)] was adjusted to 0.8:0.2:0.05 (=7,10mCzP2DBq:PCBA1BP:[Ir(dppm)$_2$(acac)]). The thickness of the light-emitting layer 1113 was set to 40 nm.

A 7,10mCzP2DBq film was formed to a thickness of 10 nm, whereby the first electron-transport layer 1114a of the light-emitting element 8 was formed. The components other than the light-emitting layer 1113 and the first electron-transport layer 1114a were formed in the same manner as those of the light-emitting element 1.

Table 5 shows element structures of the light-emitting elements 7 and 8 obtained as described above.

istics of the elements were measured. Note that the measurement was carried out at room temperature (in an atmosphere kept at 25° C.).

Figure 29:
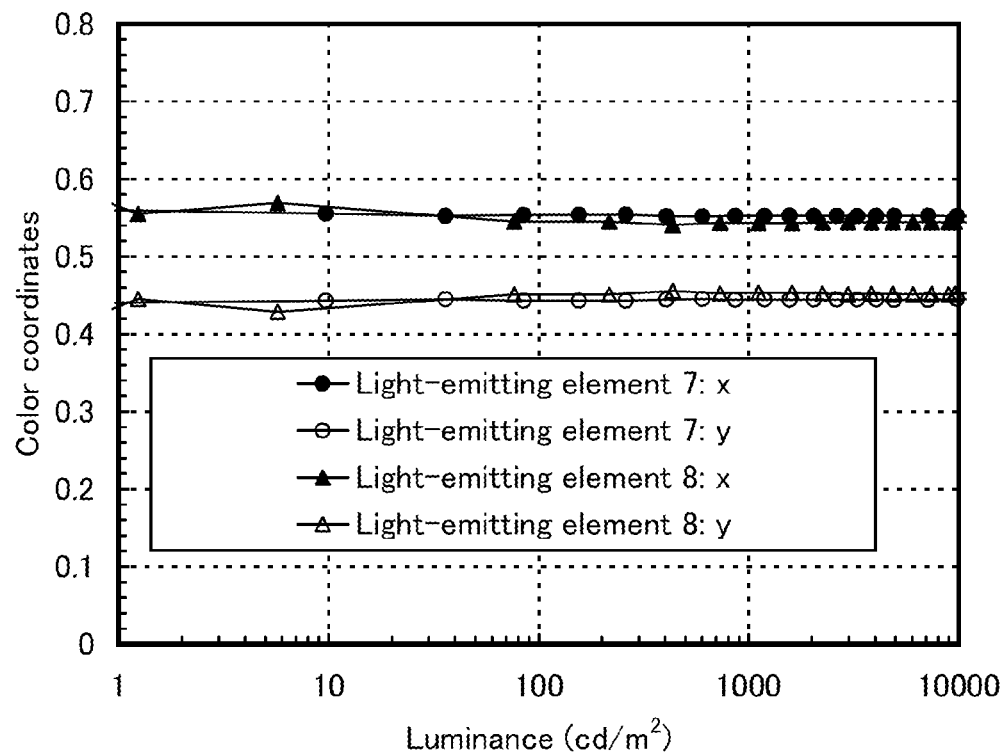
FIG. 29 shows luminance-chromaticity coordinate characteristics of light-emitting elements in Example 6.

FIG. 29 shows luminance-chromaticity coordinate characteristics of the light-emitting elements 7 and 8. In FIG. 29, the horizontal axis represents luminance (cd/m$^2$) and the vertical axis represents chromaticity coordinate (the x-coordinate or the y-coordinate). Table 6 shows voltage (V), current density (mA/cm$^2$), CIE chromaticity coordinates (x, y), luminance (cd/m$^2$), current efficiency (cd/A), and external quantum efficiency (%) of each light-emitting element at a luminance of around 1000 cd/m$^2$.

TABLE 6

|  | Voltage (V) | Current density (mA/cm$^2$) | Chromaticity (x, y) | Luminance (cd/m$^2$) | Current efficiency (cd/A) | External quantum efficiency (%) |
|---|---|---|---|---|---|---|
| Light-emitting element 7 | 3.3 | 1.9 | (0.56, 0.44) | 900 | 46 | 19 |
| Light-emitting element 8 | 3.1 | 3.1 | (0.54, 0.45) | 1100 | 36 | 14 |

Figure 30:
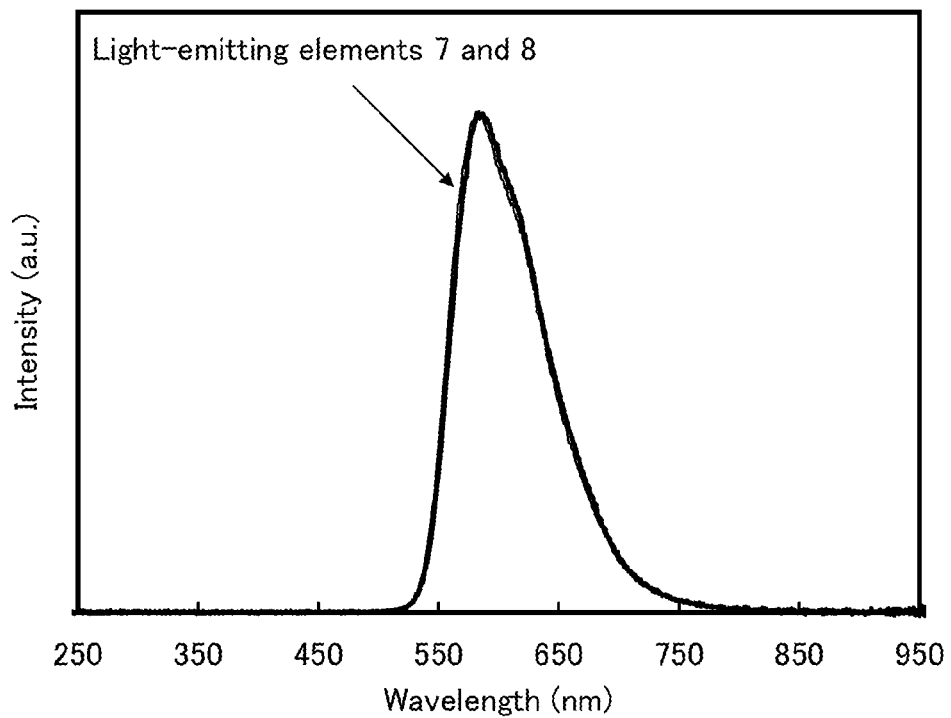
FIG. 30 shows emission spectra of the light-emitting elements in Example 6.

FIG. 30 shows emission spectra of the light-emitting elements 7 and 8, which were obtained by applying a current of 0.1 mA. In FIG. 30, the horizontal axis represents wavelength (nm) and the vertical axis represents emission intensity (arbitrary unit). As shown in FIG. 30 and Table 6, the CIE chromaticity coordinates of the light-emitting element 7 were (x, y)=(0.56, 0.44) at a luminance of 900 cd/m$^2$. The CIE chromaticity coordinates of the light-emitting element 8 were (x, y)=(0.54, 0.45) at a luminance of 1100 cd/m$^2$. The light-emitting elements 7 and 8 were found to emit light originating from [Ir(dppm)$_2$(acac)].

Table 6 shows that the light-emitting elements 7 and 8 have low driving voltage, high current efficiency, and high external quantum efficiency. Further, according to FIG. 29, the light-emitting elements 7 and 8 show substantially no change in color over a range from low luminance to high luminance. It can be said from these results that the light-emitting elements 7 and 8 each have excellent carrier balance.

As described above, light-emitting elements having low driving voltage and high emission efficiency were able to be fabricated by the use of 6,11mCzP2DBq and

TABLE 5

|  | 1$^{st}$ electrode | HIL$^a$ | HTL$^b$ | EmL$^c$ | 1$^{st}$ ETL$^d$ | 2$^{nd}$ ETL$^d$ | EIL$^e$ | 2$^{nd}$ electrode |
|---|---|---|---|---|---|---|---|---|
| Light-emitting element 7 | ITSO 110 nm | DBT3P-II:MoOx (4:2) 40 nm | BPAFLP 20 nm | 6,11mCzP2DBq:PCBA1BP:[Ir(dppm)2(acac)] (0.8:0.2:0.05) 40 nm | 6,11mCzP2DBq 10 nm | Bphen 20 nm | LiF 1 nm | Al 200 nm |
| Light-emitting element 8 | ITSO 110 nm | DBT3P-II:MoOx (4:2) 40 nm | BPAFLP 20 nm | 7,10mCzP2DBq:PCBA1BP:[Ir(dppm)2(acac)] (0.8:0.2:0.05) 40 nm | 7,10mCzP2DBq 10 nm | BPhen 20 nm | LiF 1 nm | Al 200 nm |

$^a$Hole-injection layer.
$^b$Hole-transport layer.
$^c$Light-emitting layer.
$^d$Electron-transport layer.
$^e$Electron-injection layer.

In a glove box containing a nitrogen atmosphere, the light-emitting elements 7 and 8 were sealed with a glass substrate so as not to be exposed to the air. Then, operation character- 7,10mCzP2DBq manufactured in Examples 3 and 4 as a host material of a light-emitting layer and a material of an electron-transport layer.

Reference Example 1

This example specifically shows a method of synthesizing [Ir(dppm)$_2$(acac)] used in Example 2 and the like. The structure of [Ir(dppm)$_2$(acac)] is shown below.

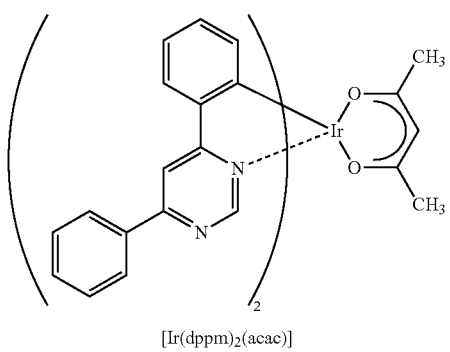

[Ir(dppm)$_2$(acac)]

Step 1: Synthesis of 4,6-diphenylpyrimidine (Abbreviation: Hdppm)

First, into a recovery flask equipped with a reflux pipe, 5.02 g of 4,6-dichloropyrimidine, 8.29 g of phenylboronic acid, 7.19 g of sodium carbonate, 0.29 g of bis(triphenylphosphine)palladium(II)dichloride (abbreviation: Pd(PPh$_3$)$_2$Cl$_2$), 20 mL of water, and 20 mL of acetonitrile were put, and the air in the flask was replaced with argon. This reaction container was subjected to irradiation with microwaves (2.45 GHz, 100 W) for one hour to be heated. Here, into the flask, 2.08 g of phenylboronic acid, 1.79 g of sodium carbonate, 0.070 g of Pd(PPh$_3$)$_2$Cl$_2$, 5 mL of water, and 5 mL of acetonitrile were further put, and the reaction container was heated again by irradiation with microwaves (2.45 GHz, 100 W) for one hour. Then, water was added to this solution and an organic layer was extracted with dichloromethane. The obtained extract was washed with water, dried with magnesium sulfate, and then filtered. The solvent of the filtrate was distilled off, and then the obtained residue was purified by silica gel column chromatography using dichloromethane as a developing solvent. As a result, a pyrimidine derivative Hdppm (yellow white powder, yield of 38%) was obtained. Note that the irradiation with microwaves was performed using a microwave synthesis system (Discover, produced by CEM Corporation). A synthesis scheme (a-1) of Step 1 is shown below.

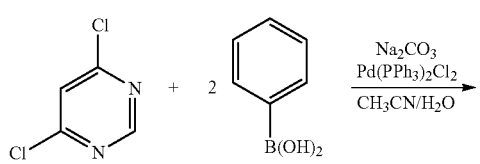

(a-1)

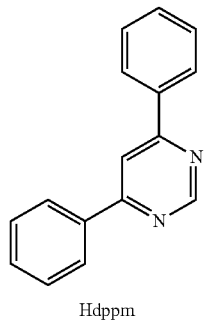

Hdppm

Step 2: Synthesis of di-μ-chloro-bis[bis(4,6-diphenylpyrimidinato)iridium(III)] (Abbreviation: [Ir(dppm)$_2$Cl]$_2$)

Next, into a recovery flask equipped with a reflux pipe, 15 mL of 2-ethoxyethanol, 5 mL of water, 1.10 g of Hdppm obtained in the above Step 1, and 0.69 g of iridium chloride hydrate (IrCl$_3$.H$_2$O) were put, and the air in the flask was replaced with argon. After that, irradiation with microwaves (2.45 GHz, 100 W) was performed for one hour. After the solvent was distilled off, the obtained residue was washed with ethanol to give a dinuclear complex [Ir(dppm)$_2$Cl]$_2$ (reddish brown powder, yield of 88%). A synthesis scheme (a-2) of Step 2 is shown below.

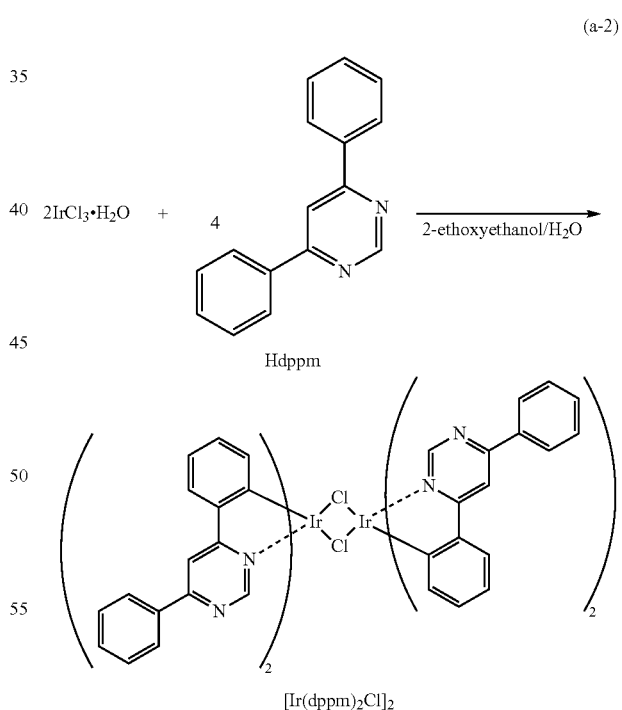

(a-2)

[Ir(dppm)$_2$Cl]$_2$

Step 3: Synthesis of: [Ir(dppm)$_2$(acac)]

Into a recovery flask equipped with a reflux pipe, 40 mL of 2-ethoxyethanol, 1.44 g of [Ir(dppm)$_2$Cl]$_2$ obtained in the above Step 2, 0.30 g of acetylacetone, and 1.07 g of sodium carbonate were put, and the air in the flask was replaced with argon, and irradiation with microwaves (2.45 GHz, 120 W) was then performed for one hour. The solvent was distilled off, the obtained residue was dissolved in dichloromethane, and filtration was performed to remove insoluble part. The obtained filtrate was washed with water and then with saturated saline, dried with magnesium sulfate, and filtered. The solvent of the filtrate was distilled off, and then the obtained residue was purified by silica gel column chromatography using dichloromethane and ethyl acetate as a developing solvent in a volume ratio of 50:1. After that, recrystallization was carried out with a mixed solvent of dichloromethane and hexane to give orange powder that was the objective substance (yield of 32%). A synthesis scheme (a-3) of Step 3 is shown below.

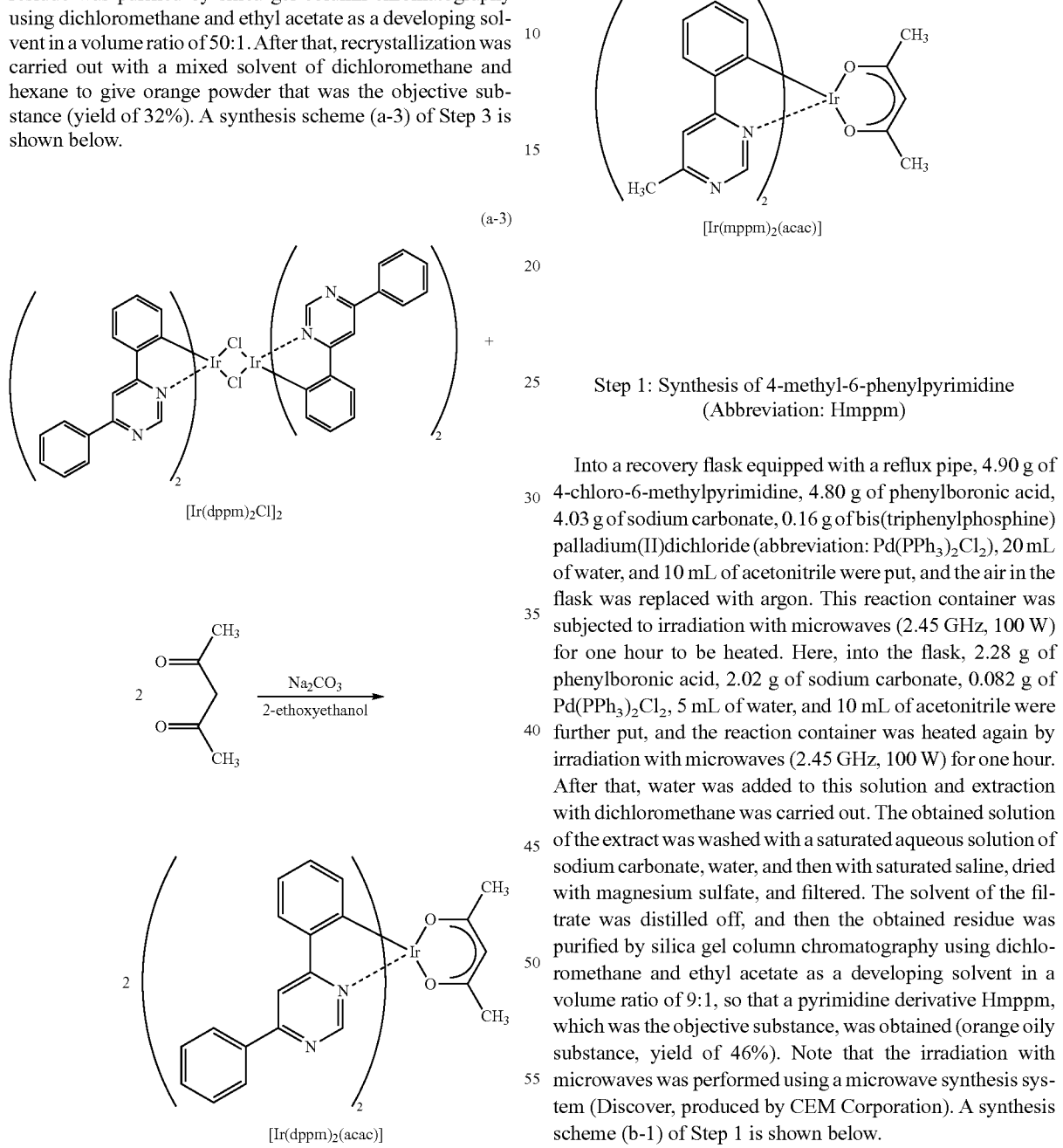

Analysis results of the orange powder obtained in the above Step 3 by nuclear magnetic resonance spectrometry ($^1$H NMR) are shown below. The results show that [Ir(dppm)$_2$(acac)] was obtained in this synthesis example.

$^1$H NMR. δ (CDCl$_3$): 1.83 (s, 6H), 5.29 (s, 1H), 6.48 (d, 2H), 6.80 (t, 2H), 6.90 (t, 2H), 7.55-7.63 (m, 6H), 7.77 (d, 2H), 8.17 (s, 2H), 8.24 (d, 4H), 9.17 (s, 2H).

Reference Example 2

This example specifically shows a method of synthesizing [Ir(mppm)$_2$(acac)] used in Example 2. The structure of [Ir(mppm)$_2$(acac)] is shown below.

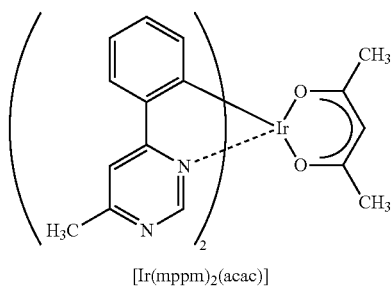

Step 1: Synthesis of 4-methyl-6-phenylpyrimidine (Abbreviation: Hmppm)

Into a recovery flask equipped with a reflux pipe, 4.90 g of 4-chloro-6-methylpyrimidine, 4.80 g of phenylboronic acid, 4.03 g of sodium carbonate, 0.16 g of bis(triphenylphosphine)palladium(II)dichloride (abbreviation: Pd(PPh$_3$)$_2$Cl$_2$), 20 mL of water, and 10 mL of acetonitrile were put, and the air in the flask was replaced with argon. This reaction container was subjected to irradiation with microwaves (2.45 GHz, 100 W) for one hour to be heated. Here, into the flask, 2.28 g of phenylboronic acid, 2.02 g of sodium carbonate, 0.082 g of Pd(PPh$_3$)$_2$Cl$_2$, 5 mL of water, and 10 mL of acetonitrile were further put, and the reaction container was heated again by irradiation with microwaves (2.45 GHz, 100 W) for one hour. After that, water was added to this solution and extraction with dichloromethane was carried out. The obtained solution of the extract was washed with a saturated aqueous solution of sodium carbonate, water, and then with saturated saline, dried with magnesium sulfate, and filtered. The solvent of the filtrate was distilled off, and then the obtained residue was purified by silica gel column chromatography using dichloromethane and ethyl acetate as a developing solvent in a volume ratio of 9:1, so that a pyrimidine derivative Hmppm, which was the objective substance, was obtained (orange oily substance, yield of 46%). Note that the irradiation with microwaves was performed using a microwave synthesis system (Discover, produced by CEM Corporation). A synthesis scheme (b-1) of Step 1 is shown below.

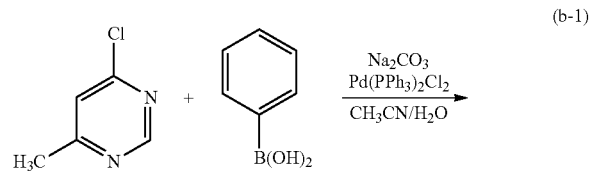

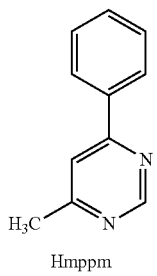

Hmppm

Step 2: Synthesis of di-μ-chloro-bis[bis(6-methyl-4-phenylpyrimidinato)iridium(III)] (Abbreviation: [Ir(mppm)$_2$Cl]$_2$)

Into a recovery flask equipped with a reflux pipe, 15 mL of 2-ethoxyethanol, 5 mL of water, 1.51 g of Hmppm obtained in Step 1, and 1.26 g of iridium chloride hydrate (IrCl$_3$.H$_2$O) were put, and the air in the flask was replaced with argon. After that, irradiation with microwaves (2.45 GHz, 100 W) was performed for one hour. The solvent was distilled off, and then the obtained residue was washed with ethanol and filtered to give a dinuclear complex [Ir(mppm)$_2$Cl]$_2$ (dark green powder, yield of 77%). A synthesis scheme (b-2) of Step 2 is shown below.

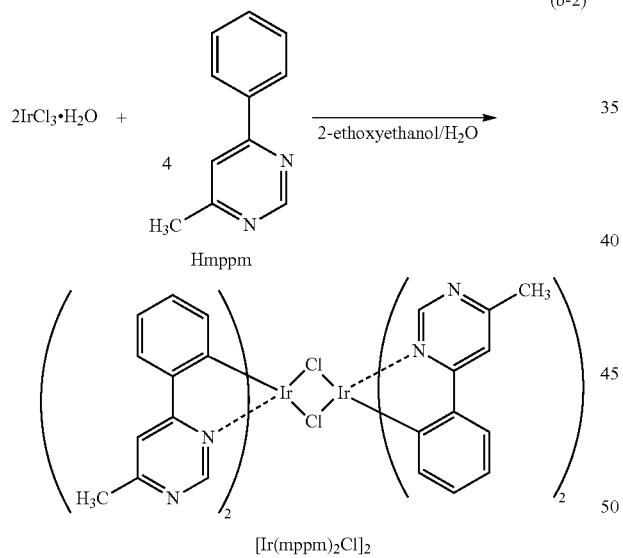

Step 3: Synthesis of [Ir(mppm)$_2$(acac)]

Into a recovery flask equipped with a reflux pipe, 40 mL of 2-ethoxyethanol, 1.84 g of the dinuclear complex [Ir(mppm)$_2$Cl]$_2$ obtained in the above Step 2, 0.48 g of acetylacetone, and 1.73 g of sodium carbonate were put, and the air in the flask was replaced with argon. After that, irradiation with microwaves (2.45 GHz, 120 W) was performed for one hour. The solvent was distilled off, the obtained residue was dissolved in dichloromethane, and filtration was performed to remove insoluble part. The obtained filtrate was washed with water and then with saturated saline, dried with magnesium sulfate, and filtered. The solvent of the filtrate was distilled off, and then the obtained residue was purified by silica gel column chromatography using dichloromethane and ethyl acetate as a developing solvent in a volume ratio of 4:1. After that, recrystallization was carried out with a mixed solvent of dichloromethane and hexane to give the objective substance as yellow powder (yield of 22%). A synthesis scheme (b-3) of Step 3 is shown below.

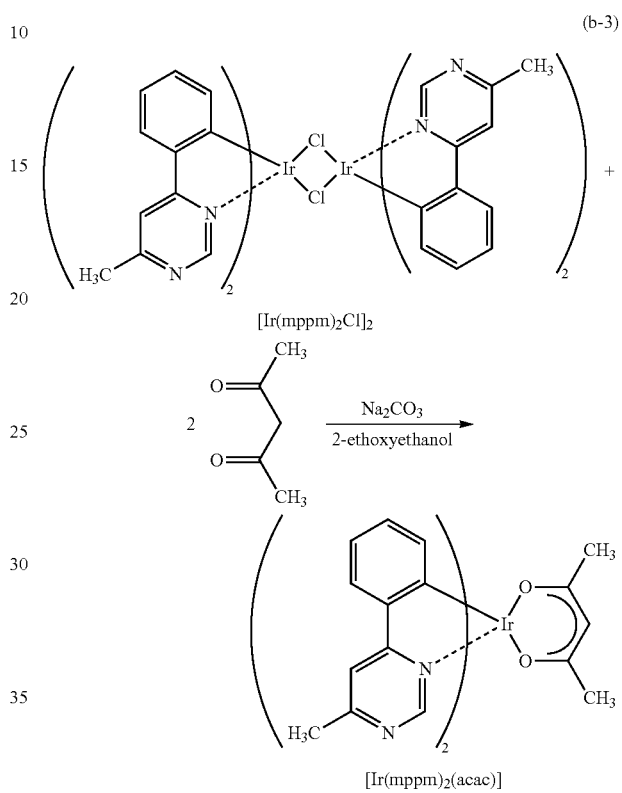

Analysis results of the yellow powder obtained in the above Step 3 by nuclear magnetic resonance spectrometry ('H NMR) are shown below. The results show that [Ir(mppm)$_2$(acac)] was obtained in this synthesis example.

$^1$H NMR. δ(CDCl$_3$): 1.78 (s, 6H), 2.81 (s, 6H), 5.24 (s, 1H), 6.37 (d, 2H), 6.77 (t, 2H), 6.85 (t, 2H), 7.61-7.63 (m, 4H), 8.97 (s, 2H).

Reference Example 3

This example specifically shows a method of synthesizing [Ir(tBuppm)$_2$(acac)] used in Example 5. The structure of [Ir(tBuppm)$_2$(acac)] is shown below.

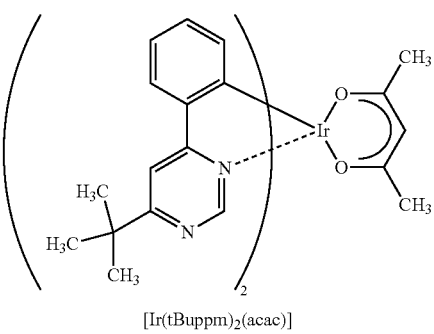

Step 1: Synthesis of 4-tert-butyl-6-phenylpyrimidine (Abbreviation: HtBuppm)

Into a recovery flask equipped with a reflux pipe, 22.5 g of 4,4-dimethyl-1-phenylpentane-1,3-dione and 50 g of formamide were put, and the air in the flask was replaced with nitrogen. This reaction container was heated under reflux for five hours. After that, the solution was poured into an aqueous solution of sodium hydroxide, and an organic layer was extracted with dichloromethane. The obtained organic layer was washed with water and saturated saline, dried with magnesium sulfate, and filtered. The filtrate was concentrated, and then the obtained residue was purified by silica gel column chromatography using hexane and ethyl acetate as a developing solvent in a volume ratio of 10:1, so that a pyrimidine derivative HtBuppm (colorless oily substance, yield of 14%) was obtained. A synthesis scheme of Step 1 is shown in the following (c-1).

(c-1)

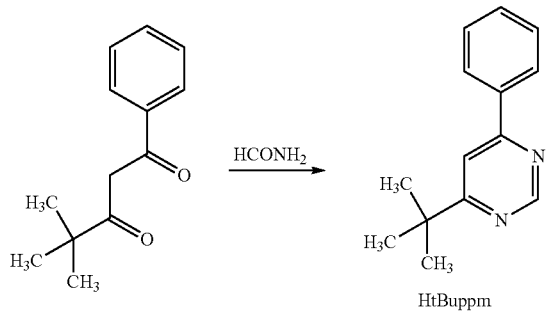

Step 2: Synthesis of di-μ-chloro-bis[bis(6-tert-butyl-4-phenylpyrimidinato)iridium(III)] (Abbreviation: [Ir(tBuppm)$_2$Cl]$_2$)

Into a recovery flask equipped with a reflux pipe, 15 mL of 2-ethoxyethanol, 5 mL of water, 1.49 g of HtBuppm obtained in the above Step 1, and 1.04 g of iridium chloride hydrate (IrCl$_3$.H$_2$O) were put, and the air in the flask was replaced with argon. After that, irradiation with microwaves (2.45 GHz, 100 W) was performed for one hour. The solvent was distilled off, and then the obtained residue was suction-filtered and washed with ethanol to give a dinuclear complex [Ir(tBuppm)$_2$Cl]$_2$ (yellow green powder, yield of 73%). A synthesis scheme of Step 2 is shown in the following (c-2).

(c-2)

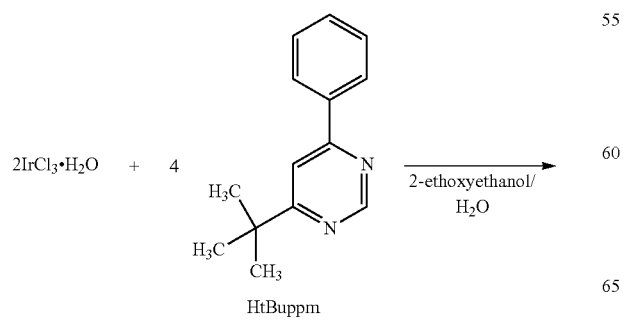

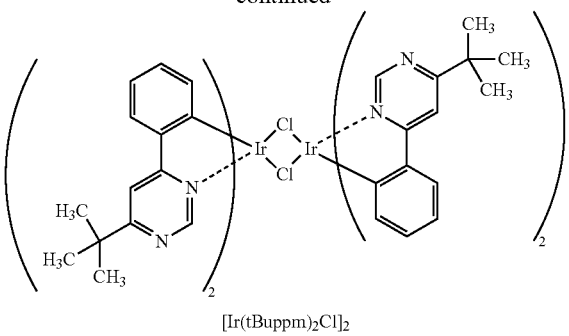

[Ir(tBuppm)$_2$Cl]$_2$

Step 3: Synthesis of [Ir(tBuppm)$_2$(acac)]

Into a recovery flask equipped with a reflux pipe, 40 mL of 2-ethoxyethanol, 1.61 g of the dinuclear complex [Ir(tBuppm)$_2$Cl]$_2$ obtained in the above Step 2, 0.36 g of acetylacetone, and 1.27 g of sodium carbonate were put, and the air in the flask was replaced with argon. After that, irradiation with microwaves (2.45 GHz, 120 W) was performed for one hour. The solvent was distilled off, and the obtained residue was suction-filtered with ethanol and washed with water and ethanol. This solid was dissolved in dichloromethane, and the mixture was filtered through a filter aid in which Celite (produced by Wako Pure Chemical Industries, Ltd., Catalog No. 531-16855), alumina, and Celite were stacked in this order. The solvent was distilled off, and the obtained solid was recrystallized from a mixed solvent of dichloromethane and hexane, so that the objective substance was obtained as yellow powder (yield of 68%). A synthesis scheme of Step 3 is shown in the following (c-3).

(c-3)

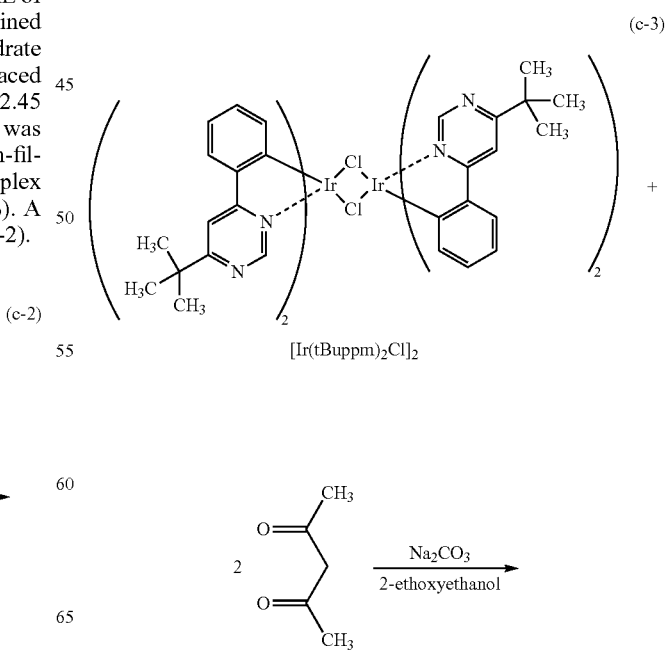

-continued

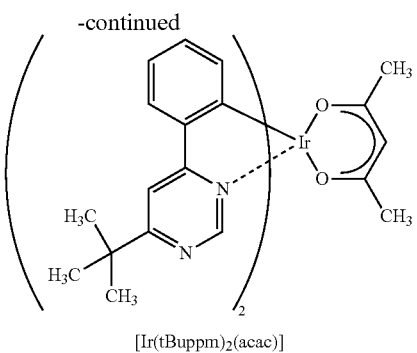

[Ir(tBuppm)₂(acac)]

Analysis results of the yellow powder obtained in the above Step 3 by nuclear magnetic resonance spectrometry ('H NMR) are shown below. The results show that [Ir(tBuppm)₂(acac)] was obtained in this synthesis example.

$^1$H NMR. δ (CDCl₃): 1.50 (s, 18H), 1.79 (s, 6H), 5.26 (s, 1H), 6.33 (d, 2H), 6.77 (t, 2H), 6.85 (t, 2H), 7.70 (d, 2H), 7.76 (s, 2H), 9.02 (s, 2H).

This application is based on Japanese Patent Application serial no. 2011-189089 filed with Japan Patent Office on Aug. 31, 2011, the entire contents of which are hereby incorporated by reference.

What is claimed is:

1. An organic compound represented by a formula (G1):

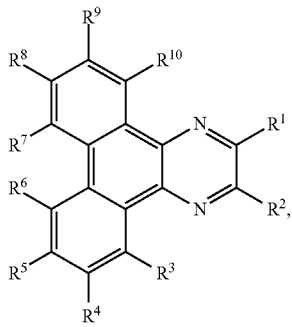

(G1)

wherein any one of $R^1$ to $R^{10}$ represents a substituent represented by a formula (G1-1), another one of $R^1$ to $R^{10}$ represents a substituent represented by a formula (G1-2), and the others separately represent hydrogen, an alkyl group having 1 to 6 carbon atoms, a substituted or unsubstituted phenyl group, or a substituted or unsubstituted biphenyl group:

—α¹—A¹ (G1-1)

—α²—A², (G1-2)

wherein α¹ and α² separately represent a substituted or unsubstituted phenylene group or a substituted or unsubstituted biphenyldiyl group, and wherein A¹ and A² separately represent a substituted or unsubstituted dibenzothiophenyl group or a substituted or unsubstituted dibenzofuranyl group.

2. The organic compound according to claim 1,
wherein the organic compound is represented by a formula (G2-1):

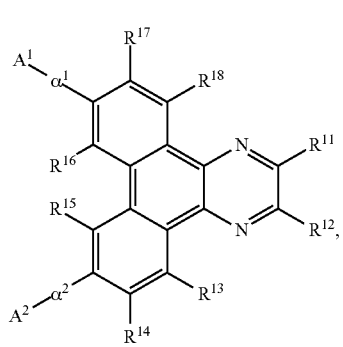

(G2-1)

and
wherein $R^{11}$ to $R^{18}$ separately represent hydrogen, an alkyl group having 1 to 6 carbon atoms, a substituted or unsubstituted phenyl group, or a substituted or unsubstituted biphenyl group.

3. The organic compound according to claim 1,
wherein the organic compound is represented by a formula (G2-2):

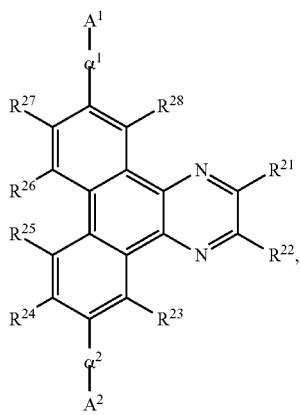

(G2-2)

and
wherein $R^{21}$ to $R^{28}$ separately represent hydrogen, an alkyl group having 1 to 6 carbon atoms, a substituted or unsubstituted phenyl group, or a substituted or unsubstituted biphenyl group.

4. The organic compound according to claim 1,
wherein α¹ and the α² are separately represented by a formula (α-1) or a formula (α-2):

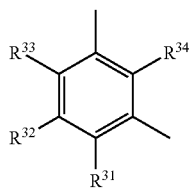

(α-1)

-continued (α-2)

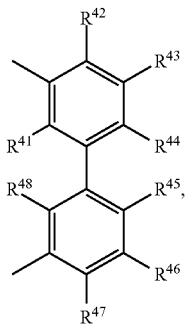

and wherein $R^{31}$ to $R^{34}$ and $R^{41}$ to $R^{48}$ separately represent hydrogen, an alkyl group having 1 to 6 carbon atoms, a substituted or unsubstituted phenyl group, a substituted or unsubstituted biphenyl group, a substituted or unsubstituted carbazolyl group, a substituted or unsubstituted dibenzothiophenyl group, or a substituted or unsubstituted dibenzofuranyl group.

5. The organic compound according to claim 1, wherein $A^1$ and $A^2$ are separately represented by any one of formulae (1-1) and (1-2):

(1-1)

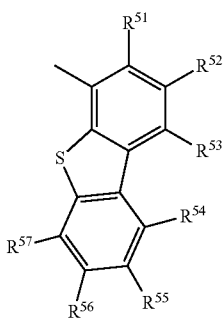

(1-2)

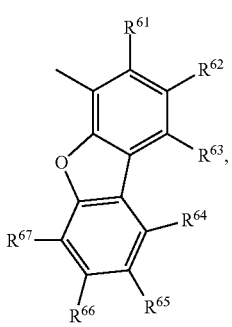

and wherein $R^{51}$ to $R^{57}$ and $R^{61}$ to $R^{67}$ separately represent hydrogen, an alkyl group having 1 to 6 carbon atoms, a substituted or unsubstituted phenyl group, or a substituted or unsubstituted biphenyl group.

6. The organic compound according to claim 1, wherein $A^1$ and $A^2$ are each represented by a formula (1-1):

(1-1)

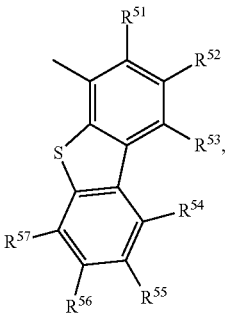

wherein $R^{51}$ to $R^{57}$ separately represent hydrogen, an alkyl group having 1 to 6 carbon atoms, a substituted or unsubstituted phenyl group, or a substituted or unsubstituted biphenyl group.

7. The organic compound according to claim 1, wherein $A^1$ the $A^2$ are each represented by a formula (1-2):

(1-2)

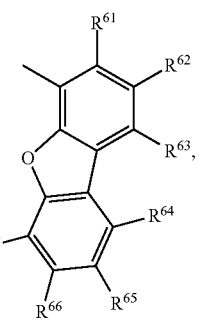

and wherein $R^{61}$ to $R^{67}$ separately represent hydrogen, an alkyl group having 1 to 6 carbon atoms, a substituted or unsubstituted phenyl group, or a substituted or unsubstituted biphenyl group.

8. A light-emitting device comprising:
a pair of electrodes; and
a light-emitting layer containing an organic compound between the pair of electrodes,
wherein the organic compound is represented by a formula (G1):

(G1)

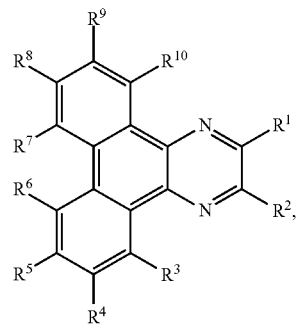

wherein any one of $R^1$ to $R^{10}$ represents a substituent represented by a formula (G1-1), another one of $R^1$ to $R^{10}$ represents a substituent represented by a formula (G1-2), and the others separately represent hydrogen, an alkyl group having 1 to 6 carbon atoms, a substituted or unsubstituted phenyl group, or a substituted or unsubstituted biphenyl group:

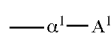 (G1-1)

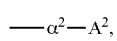 (G1-2)

wherein $\alpha^1$ and $\alpha^2$ separately represent a substituted or unsubstituted phenylene group or a substituted or unsubstituted biphenyldiyl group, and wherein $A^1$ and $A^2$ separately represent a substituted or unsubstituted dibenzothiophenyl group or a substituted or unsubstituted dibenzofuranyl group.

9. The light-emitting device according to claim 8, wherein the light-emitting layer further comprises a light-emitting substance.

10. The light-emitting device according to claim 9, wherein the light-emitting substance is a phosphorescent compound.

11. The light-emitting device according to claim 8, further comprising an electron-transport layer between the light-emitting layer and one of the pair of electrodes, wherein the electron-transport layer comprises the organic compound.

12. The light-emitting device according to claim 11, wherein the electron-transport layer is in contact with the light-emitting layer.

13. The light-emitting device according to claim 11, further comprising a second electron-transport layer between the electron-transport layer and the one of the pair of electrodes.

14. An electronic device comprising the light-emitting device according to claim 8.

15. A lighting device comprising the light-emitting device according to claim 8.

16. The light-emitting device according to claim 8,
wherein the organic compound is represented by a formula (G2-1):

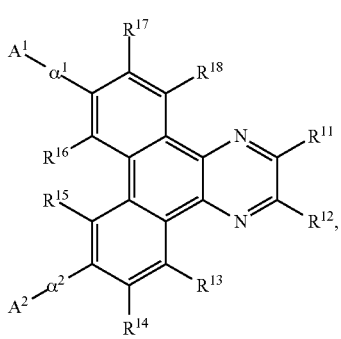

(G2-1)

and
wherein $R^{11}$ to $R^{18}$ separately represent hydrogen, an alkyl group having 1 to 6 carbon atoms, a substituted or unsubstituted phenyl group, or a substituted or unsubstituted biphenyl group.

17. The light-emitting device according to claim 8,
wherein the organic compound is represented by a formula (G2-2):

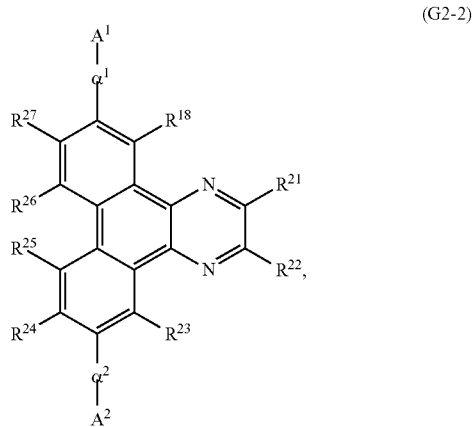

(G2-2)

and
wherein $R^{21}$ to $R^{28}$ separately represent hydrogen, an alkyl group having 1 to 6 carbon atoms, a substituted or unsubstituted phenyl group, or a substituted or unsubstituted biphenyl group.

18. The light-emitting device according to claim 8,
wherein $\alpha^1$ and the $\alpha^2$ are separately represented by a formula ($\alpha$-1) or a formula ($\alpha$-2):

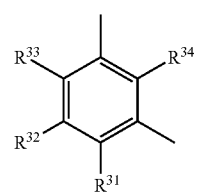

($\alpha$-1)

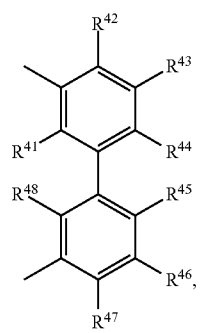

($\alpha$-2)

and
wherein $R^{31}$ to $R^{34}$ and $R^{41}$ to $R^{48}$ separately represent hydrogen, an alkyl group having 1 to 6 carbon atoms, a substituted or unsubstituted phenyl group, a substituted or unsubstituted biphenyl group, a substituted or unsubstituted carbazolyl group, a substituted or unsubstituted dibenzothiophenyl group, or a substituted or unsubstituted dibenzofuranyl group.

19. The light-emitting device according to claim 8, wherein $A^1$ and $A^2$ are separately represented by any one of formulae (1-1) and (1-2):
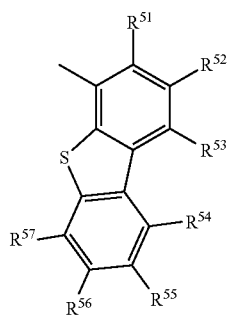
(1-1)
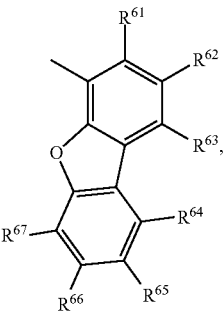
(1-2)
and
wherein $R^{51}$ to $R^{57}$ and $R^{61}$ to $R^{67}$ separately represent hydrogen, an alkyl group having 1 to 6 carbon atoms, a substituted or unsubstituted phenyl group, or a substituted or unsubstituted biphenyl group.
\* \* \* \* \*